(12) United States Patent
Newkirk et al.

(10) Patent No.: US 8,572,778 B2
(45) Date of Patent: Nov. 5, 2013

(54) USER INTERFACE FOR HOSPITAL BED

(75) Inventors: David C. Newkirk, Lawrenceburg, IN (US); John B. Wilker, Jr., Dillsboro, IN (US); James M. Allen, Batesville, IN (US); Robert M. Zerhusen, Cincinnati, OH (US); Douglas A. Seim, Okeana, OH (US); Irvin J. Vanderpohl, III, Greensburg, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 1578 days.

(21) Appl. No.: 11/960,287

(22) Filed: Dec. 19, 2007

(65) Prior Publication Data

US 2008/0235872 A1 Oct. 2, 2008

Related U.S. Application Data

(60) Provisional application No. 60/982,300, filed on Oct. 24, 2007, provisional application No. 60/921,192, filed on Mar. 30, 2007.

(51) Int. Cl.
*A47C 27/10* (2006.01)

(52) U.S. Cl.
USPC .......................................................... 5/600

(58) Field of Classification Search
USPC .......................................................... 5/600
See application file for complete search history.

(56) References Cited

U.S. PATENT DOCUMENTS

| | | | |
|---|---|---|---|
| 5,181,288 A | 1/1993 | Heaton et al. | |
| 5,403,251 A | 4/1995 | Belsito et al. | |
| 5,542,138 A | 8/1996 | Williams et al. | |
| 5,559,301 A * | 9/1996 | Bryan et al. | 84/653 |
| 5,611,096 A | 3/1997 | Bartlett et al. | |
| 5,664,270 A | 9/1997 | Bell et al. | |
| 5,713,856 A | 2/1998 | Eggers et al. | |
| 5,833,623 A | 11/1998 | Mann et al. | |
| 5,861,582 A | 1/1999 | Flanagan et al. | |
| 6,014,784 A | 1/2000 | Taylor et al. | |
| 6,119,291 A * | 9/2000 | Osborne et al. | 5/600 |
| 6,146,523 A | 11/2000 | Kenley et al. | |
| 6,279,183 B1 | 8/2001 | Kummer et al. | |
| 6,339,410 B1 | 1/2002 | Milner et al. | |

(Continued)

FOREIGN PATENT DOCUMENTS

| | | |
|---|---|---|
| EP | 1 623 666 A2 | 2/2006 |
| WO | 01/75405 A1 | 10/2001 |

(Continued)

OTHER PUBLICATIONS

Partial European search report from EP 08 25 1066 dated.

(Continued)

*Primary Examiner* — William Kelleher

(74) *Attorney, Agent, or Firm* — Barnes & Thornburg LLP

(57) ABSTRACT

A user module for a patient support apparatus is provided. The user module has a user interface operably coupled thereto. The user interface includes an input device and an output device. The output device includes a visual display including textual and non-textual elements. The non-textual elements include enhanced, graphical, and animated portions relating to one or more operational features of the patient support or to a person positionable on the patient support. The input device includes one or more touch sensors corresponding to defined regions of the visual display.

25 Claims, 36 Drawing Sheets

(56) References Cited

U.S. PATENT DOCUMENTS

| | | | |
|---|---|---|---|
| 6,351,678 B1 * | 2/2002 | Borders | 700/83 |
| 6,353,950 B1 | 3/2002 | Bartlett et al. | |
| 6,371,123 B1 | 4/2002 | Stark et al. | |
| 6,384,728 B1 | 5/2002 | Kanor et al. | |
| 6,487,735 B1 | 12/2002 | Jacques, II et al. | |
| 6,493,568 B1 | 12/2002 | Bell et al. | |
| 6,536,056 B1 | 3/2003 | Vrzalik et al. | |
| 6,566,833 B2 * | 5/2003 | Bartlett | 318/564 |
| 6,771,181 B1 | 8/2004 | Hughen, Jr. | |
| 6,829,796 B2 | 12/2004 | Salvatini et al. | |
| 7,033,539 B2 | 4/2006 | Kensky et al. | |
| 7,038,588 B2 | 5/2006 | Boone et al. | |
| 7,076,818 B2 | 7/2006 | Kummer et al. | |
| 7,237,287 B2 | 7/2007 | Weismiller et al. | |
| 2002/0059679 A1 | 5/2002 | Weismiller et al. | |
| 2002/0111701 A1 | 8/2002 | Borders | |
| 2004/0193449 A1 | 9/2004 | Wildman et al. | |
| 2004/0227737 A1 | 11/2004 | Novak et al. | |
| 2005/0128184 A1 | 6/2005 | McGreevy | |
| 2005/0166324 A1 | 8/2005 | Dixon et al. | |
| 2005/0172405 A1 | 8/2005 | Menkedick et al. | |
| 2005/0273940 A1 | 12/2005 | Petrosenko et al. | |
| 2005/0288571 A1 | 12/2005 | Perkins et al. | |
| 2006/0101581 A1 * | 5/2006 | Blanchard et al. | 5/713 |
| 2006/0103636 A1 | 5/2006 | Parsons | |
| 2006/0117482 A1 * | 6/2006 | Branson | 5/600 |
| 2006/0150332 A1 | 7/2006 | Weismiller et al. | |
| 2006/0229557 A1 | 10/2006 | Fathallah et al. | |
| 2007/0066866 A1 | 3/2007 | Noguchi et al. | |
| 2007/0163045 A1 | 7/2007 | Becker et al. | |
| 2007/0164871 A1 | 7/2007 | Dionne et al. | |
| 2007/0174964 A1 | 8/2007 | Lemire et al. | |

FOREIGN PATENT DOCUMENTS

| | | |
|---|---|---|
| WO | 2004/021952 A2 | 3/2004 |
| WO | 2007/008830 A2 | 1/2007 |
| WO | 2007/008831 A2 | 1/2007 |
| WO | WO 2007/008831 A2 | 1/2007 |

OTHER PUBLICATIONS

European Search Report from EP11 18 4511 dated Feb. 27, 2012, 6 pages.

Partial European search report dated Feb. 16, 2009 from EP 08 25 1066.

"Efica CC Dynamic Air Therapy Unit Service Manual," Hill-Rom Company, Inc., 2000, Third Edition, 531 pages.

"V-CUE Dynamic Air Therapy," Hill-Rom, 1998, 6 pages.

"V-CUE Dynamic Air Therapy Unit Service Manual," Hill-Rom Services, Inc., 2000, Third Edition, 223 pages.

"V-CUE Dynamic Air Therapy Unit for Household Use," Hill-Rom, Jul. 2001, 36 pages.

"V-CUE Dynamic Air Therapy Unit," Hill-Rom Services, Inc., Sep. 2000, 64 pages.

"EFICA CC Dynamic Air Therapy Unit," Hill-Rom, Jul. 1994, 35 pages.

* cited by examiner

Scale

Touch the setting you want to adjust

Last recorded weight: 70.4 kg / 150.8 lbs

24 hrs ⇩ Lost: 1.5 kg / 3.3 lbs (0.3%)

Last weight: Tue. 1/16/06 @ 12:45 PM

Last zeroed: Tue. 1/16/06 @ 5:33 PM

- Tools
- Help ?
- Weigh Patient
- 76 kg
- 68 kg
- Jan 9 — Today
- View History
- kg / lbs
- Zero Scale
- Adjust Weight
- Main Menu
- Scale
- Alarms
- Surface
- Therapy

FIG. 5

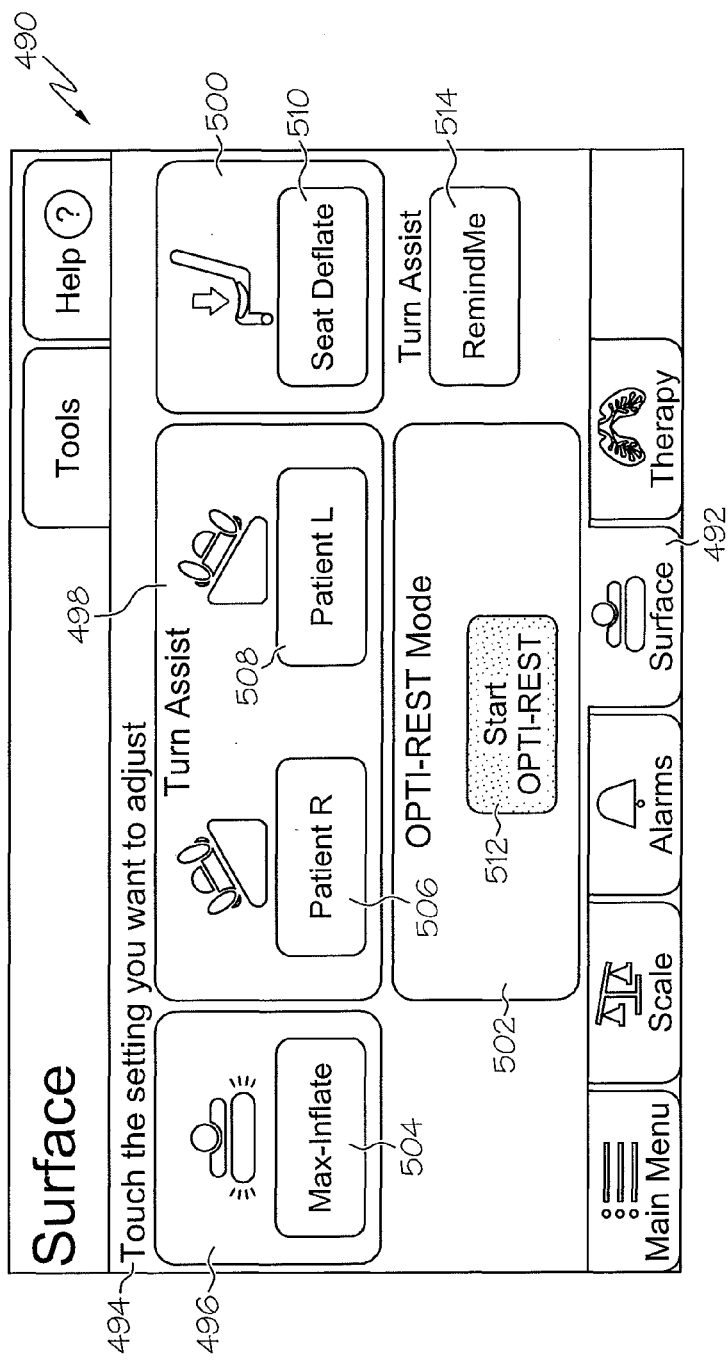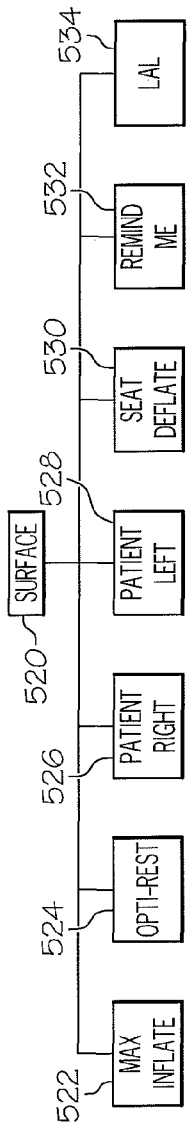
FIG. 11
FIG. 12

USER INTERFACE FOR HOSPITAL BED

RELATED APPLICATIONS

This application claims the benefit of U.S. Provisional Patent Application Ser. No. 60/982,300, filed Oct. 24, 2007, and claims the benefit of U.S. Provisional Patent Application Ser. No. 60/921,192, filed Mar. 30, 2007, both of which are incorporated herein by this reference.

This application is related to U.S. Utility patent application Ser. No. 11/672,274, filed Feb. 7, 2007, entitled USER MODULE FOR A PATIENT SUPPORT, to Newkirk, et al., and PCT Patent Application Serial No. PCT/US06/61795, filed Feb. 7, 2007 entitled USER MODULE FOR A PATIENT SUPPORT, to Newkirk et al., both of which are incorporated herein by this reference.

BACKGROUND

Patient supports, such as hospital beds, mattresses, stretchers, operating room tables, and the like, are commonly used in a variety of care environments to facilitate patient care and transport.

User modules are often provided to enable a user to perform a variety of automated functions relating to a patient support. Examples of such automated functions include raising or lowering one or more sections of the patient support, adjusting the configuration of a bed frame or support surface or a portion thereof, and activating or deactivating selected therapies, alarms, communications, and other automated features of the patient support. As such, user modules may be operably coupled to a bed and/or support surface controller or control system, a remote computer, an air supply or other like service supply or supplies.

Many conventional user modules are either fixed in or coupled to a siderail or footboard of a patient support, or are provided as pendants or removable modules that may be stored in the siderail or footboard and removed for use.

Healthcare professionals often have many demanding responsibilities and need to work as efficiently as possible. However, many conventional patient support user modules are cumbersome for a caregiver or technician to use due to a non-intuitive design, inefficient feedback from the module or other reasons. Such shortcomings can result in reduced efficiency of caregivers and other healthcare professionals.

Clear, succinct, easy to understand instructions for using the module are often desirable. Non-textual indicators that can quickly be understood without requiring fluency in any particular language may also be desirable. Particularly with graphic displays, lack of user-friendly feedback can leave users in doubt as to whether their input selections have been accepted by the user module. Additionally, with larger amounts of informational content being provided on compact displays available to caregivers in patient care environments, verification of a single changed parameter on such displays can become exceedingly difficult. Further, the lack of a clear, easy to understand or current depiction of information such as the patient's weight, therapeutic settings, status of the patient support, and historical data can result in not only inefficiencies but also user frustration if the caregiver's time must be spent figuring out how to use the module rather than on providing patient care.

Some patient supports are configured to provide therapeutic functions or features to the patient, for example, pressure redistribution, turning assistance, rotation, percussion and vibration, low air loss, and the like. Pressure redistribution generally refers to efforts to reduce or redistribute pressure away from parts of the patient's body that are in frequent contact with the patient support, in an effort to reduce the risk of the patient developing pressure ulcers or bed sores. Turning assistance refers to a feature in which either longitudinal side of the bed or mattress is automatically raised to assist a caregiver in turning the patient onto his or her side. In general, rotation therapy provides periodic rotational motion for the patient in order to avoid physiological issues related to prolonged confinement to a patient support apparatus. In patients that have pulmonary infections or conditions, rotation may also be used to help mobilize the secretions of the lungs by angling the chest so that secretions can move away from the affected lobe. Percussion and vibration are also therapies directed to pulmonary infections such as pneumonia and other lung complications. In general, percussion helps mobilize secretions from the lung, while vibration helps columnize the secretions to help create a productive cough. Low air loss generally refers to a process whereby air is circulated underneath the patient to provide a cooling effect.

Patient supports that provide one or more of such automated therapy functions and features also have a user interface for a caregiver to control the operation of such features. Because such features often involve movement of the patient, appropriate configuring, operation, and duration of the automated therapy function is important. Therefore, it is particularly desirable to address all of the shortcomings of known user modules in this environment.

SUMMARY

In this disclosure, a user module for a patient support is described. The user module includes a communication interface configured to communicate signals from the user module to a patient support having at least one automated function and being configured to support a patient in at least a substantially horizontal position and to communicate signals from the patient support to the user module. The user module includes an input device configured to receive a signal indicative of a selection made by a user relating to an automated function of the patient support, and an output device including a visual display configured to display a first graphical depiction of a person positioned on a patient support in response to a selection made by a user relating to a first function and to display a second graphical depiction of a person positioned on a patient support in response to a selection made by a user relating to a second function of the patient support. The first graphical depiction includes a first animated element indicative of movement associated with operation of the first function and the second graphical depiction includes a second animated element indicative of movement associated with operation of the second function.

The output device may be configured to display the first graphical depiction and the second graphical depiction at the same time. The first animated element may include an arrow and a portion of the graphical depiction of a person positioned on a patient support. The second animated element may include concentric circles and a portion of the graphical depiction of a person positioned on a patient support.

The output device may be configured to substantially simultaneously display current data relating to at least one alarm feature of the patient support, current data relating to at least one therapy function of the patient support, and a graphical representation of a patient support including an animated portion indicative of a status of an automated function of the patient support.

The output device may be configured to display a first region including a first selectable option and a second region spaced from the first region, where the second region includes a second selectable option, the first selectable option is displayed in a first color and the second selectable option is displayed in a second color contrasting with the first color. The second selectable option may be displayed in the second color prior to selection by a user of the second selectable option and the second selectable option may be displayed in a third color contrasting with the second color after selection by a user of the second selectable option. The second color may be green and the third color may be red.

The output device may be configured to display in a data region current data relating to a function of the patient support or a characteristic of a patient positionable on the patient support, where the data region is defined relative to the rest of the display by yellow highlighting.

The user module may include a user control to configure a setting of the patient support, the user control including a touch sensor associated with a graphical depiction of the user control displayed on the visual display, wherein the depiction of the user control includes a first numerical value representative of the current configuration of the setting, the user control is configured to enable a user to select a new configuration for the setting with one touch, and the depiction of the user control automatically changes to replace the first numerical value with a second numerical value on the user control when the second numerical value is selected by the user.

A patient support apparatus is also described, including a frame having first and second longitudinally spaced ends and first and second laterally spaced sides, a housing positionable adjacent one of the sides or ends of the frame, a user interface supported by the housing, the user interface including a dynamic display and at least one touchscreen control associated with a region of the dynamic display, and at least one electromechanical switch supported by the housing, wherein activation of at least one of the switches activates a display of the user interface.

The housing may have a front panel, where the user interface is supported by the front panel, and an electromechanical switch, which is spaced from the user interface on the front panel and electrically coupled to the user interface. Activation of the electromechanical switch may cause a pop-up window to appear on the dynamic display. The user interface and an electromechanical switch may be coupled to a siderail of the patient support. The user interface and an electromechanical switch may alternatively or in addition be coupled to a footboard of the patient support.

Also described is a patient support apparatus including a bed having first and second longitudinally spaced ends, first and second laterally spaced sides and at least one computer-controllable function, a controller operably coupled to the bed to control at least one bed function, a plurality of user modules operably coupled to the controller, each user module being configured to display output relating to a bed function and receive input from a user relating to a bed function, and a memory including instructions executable to process a first input received by a first user module and second input received by a second user module and update the displays of the user modules.

At least one of the user modules may include a user interface including a graphical element and a touchscreen control. The touchscreen control may be activatable by a user to configure a setting for a bed therapy function for which a single value is selectable from a plurality of values, the plurality of values are displayed on the user interface, and the touchscreen control is configured to enable the user to select a value from the plurality of values by contacting the touchscreen control only one time. The executable instructions may include instructions to display the same output on all of the user modules at the same time. The second user module display may be updated in response to the first input and the first user module display is updated in response to the second input.

Also described is a patient support apparatus including a patient support including a computer-controllable weigh system, a user module operably coupled to the bed to control the weigh system, and a memory operably coupled to the user module, where the memory includes executable instructions configured to determine a weight of a patient positioned on the patient support, including instructions to prompt a user to identify one or more items added or removed from the patient support, weigh the patient, and automatically account for weight changes due to the identified items such that the weight change due to the identified items is included in the determination of the patient's weight.

The executable instructions may include waiting a period of time before weighing the patient to allow the user time to add or remove items from the patient support. The executable instructions may include waiting a period of time before weighing the patient to allow the user time to let go of the patient support.

A patient support apparatus is also described, in which a patient support includes at least one computer-controllable bed function. The apparatus also includes a user module operably coupled to the patient support to control the at least one function of the patient support, and a memory operably coupled to the user module, where the memory includes executable instructions configured to enable a user to set a reminder relating to at least one patient support function, including instructions to prompt the user to set a predetermined amount of time after which the user module will generate an alert relating to a patient support function, and cause the user module to generate the alert if the predetermined amount of time has elapsed. The instructions may include permitting a user to set a first reminder relating to a turning assistance function, a second reminder relating to a rotation therapy function, and a third reminder relating to a percussion and vibration function.

A patient support apparatus including a patient support, a communications port and a user module is also described. The patient support includes a frame having first and second laterally spaced sides and first and second longitudinally spaced ends, and a plurality of automated functions. The communications port includes a connector to connect with a remote device having a memory and programming information stored in the memory of the remote device. The user module is operably coupled to the communications port and to the patient support. The user module is usable to control operation of at least one of the automated functions of the patient support. The user module includes an input mechanism, a display, a memory, programming information stored in the memory, a processor, and electrical circuitry. The programming information of the user module includes instructions executable to cause the user module to automatically detect connection of a remote device to the communications port.

The programming information of the user module may include executable instructions to receive programming information from the remote device via the communications port. The programming information of the user module may include executable instructions to update the display of the user module when programming information is received from the remote device. The patient support may include a network and a plurality of function modules coupled to the network, and the programming information of the user module may include executable instructions to provide programming information received from the remote device to a function module over the network.

Patentable subject matter may include one or more features or combinations of features shown or described anywhere in this disclosure including the written description, drawings, and claims.

BRIEF DESCRIPTION OF THE DRAWINGS

The detailed description of the drawings refers to the following figures in which:

FIG. 5 is a screen shot of a user interface for weigh scale features of a patient support, including instructional information, text data, graphical data, selective highlighting, and user controls;

FIG. 11 is a screen shot of a user interface for surfaces features of a patient support, including text, graphical icons, user controls, selective highlighting and selective coloration;

FIG. 12 is a diagram illustrating surface feature options of a patient support;

DETAILED DESCRIPTION OF THE DRAWINGS

This disclosure refers to illustrative embodiments shown in the accompanying drawings and described herein.

Figure 1:
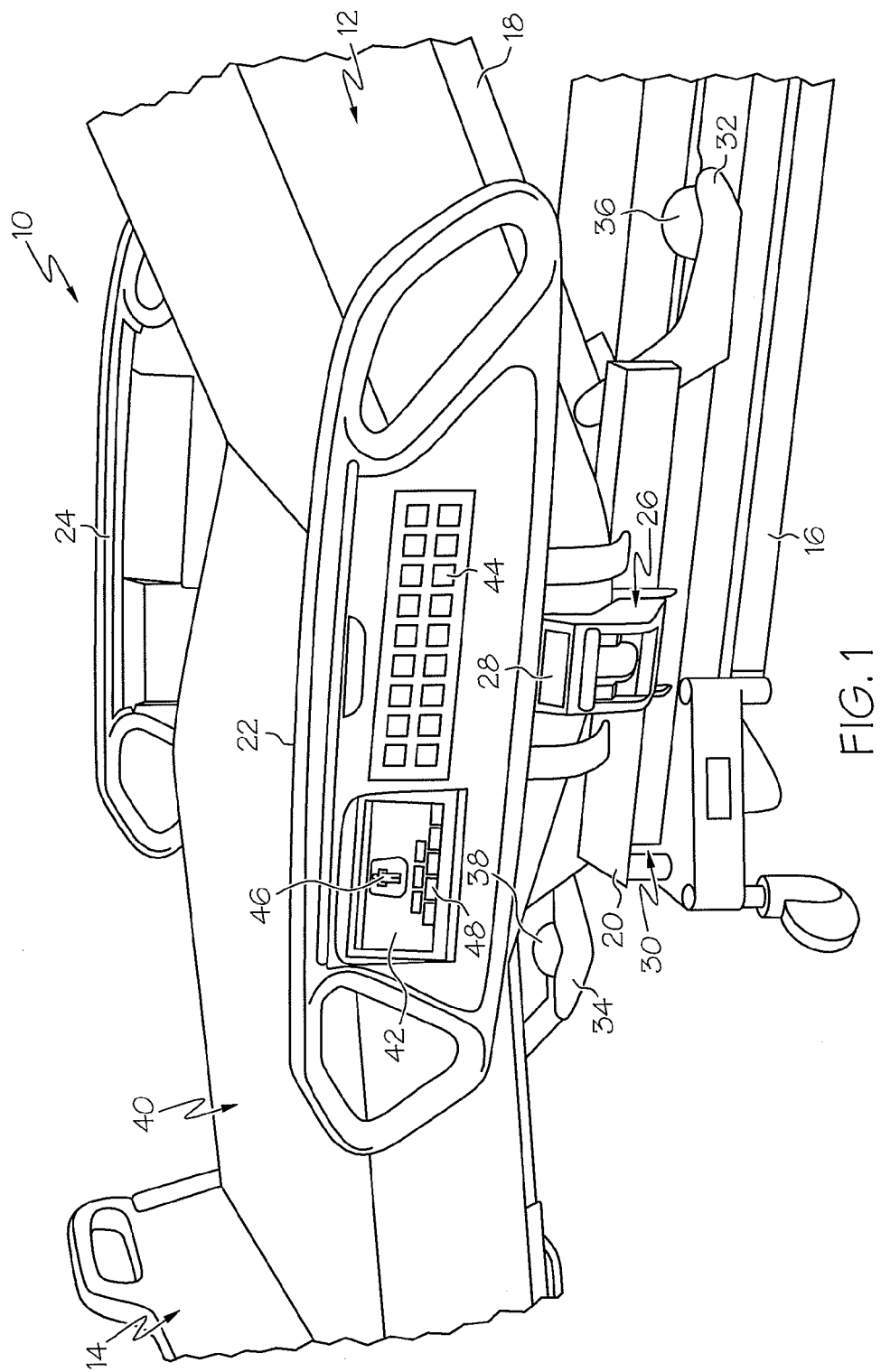
FIG. 1 is a simplified perspective view of an embodiment of a patient support, with portions cut away, including a siderail-mounted user module including a dynamic display and touch-sensitive controls, and a plurality of hardpanel controls.

An embodiment of a patient support 10 including a head end 12 and a foot end 14 is depicted in FIG. 1, with portions of the head and foot ends 12, 14 not shown. In general, patient support 10 includes a bed frame having a base 16, a deck 18, an upper or intermediate frame 20, a lift mechanism 30 configured to raise and lower frame 20 relative to base 16, head articulation mechanism 32 configured to raise and lower a head and/or upper torso section of deck 18, foot articulation mechanism 34 configured to raise and lower a foot, leg, and/or lower torso section of deck 18. As such, patient support 10 may be configurable to assume a variety of positions including a horizontal position, a chair-like position, Trendelenburg, reverse Trendelenburg and/or other positions.

In this disclosure, unless specifically stated otherwise, the term "patient support" may be used to refer to a bed, a patient support surface, mattress, or a bed and surface or mattress combination, "bed" may be used to refer to a hospital bed, stretcher, or other similar device for supporting a person in at least a horizontal position, and a "surface" or "mattress" may include powered or nonpowered surfaces with or without built-in therapeutic features. The TotalCare® bed, sold by the Hill-Rom Company, Inc. of Batesville, Ind., U.S.A., is an example of a patient support.

Barriers such as endboards and/or siderails may be provided adjacent the perimeter of patient support 10. In FIG. 1, an exemplary footboard 14 and siderails 22, 24 are illustrated. Footboard 14 is mounted to frame 20 adjacent the foot end 14. A headboard (not shown) may additionally be mounted to frame 20 adjacent the head end 12. Siderails 22, 24 are pivotably mounted to frame 20 via couplers 26. Wheels or casters also may be provided to provide mobility of the bed.

One or more sensors 28, 36, 38 may be provided to enable automatic detection of a change in position of patient support 10 or a portion thereof. One or more siderail sensors 28 may be coupled to each siderail 22, 24 to transmit a signal to a control system (described below) to indicate that a siderail is being raised or lowered or is in an "up" or "down" position. Sensors 28 may include reed switches, proximity sensors, or the like.

A head of bed angle sensor 36 transmits a signal to a control system to indicate that the head section of the patient support is being raised or lowered, or is in an "up" or "down" position, or is at a particular angle relative to the bed frame 20 or other horizontal axis, or is within or outside a particular range of angles. Similarly, a foot of bed angle sensor 38 transmits a signal to a control system to indicate that the foot section of the patient support is being raised or lowered, or is in an "up" or "down" position, or is at a particular angle relative to a horizontal axis or frame 20, or is within or outside a particular range of angles. In general, angle sensors 36, 38 may include potentiometers, ball switches, accelerometers, inclinometers, or any other type of device that is usable to measure or determine an angle or relative position and produce an output relating to the angle or position.

A patient support surface 40 is supportable by deck 18. In general, patient support surface 40 includes a cover defining an interior region in which a variety of support components such as air bladders, foam, three-dimensional thermoplastic fibers, and/or other support elements may be arranged. In the illustrated embodiment, air bladders are configured to provide one or more therapeutic services to a person positioned on the surface 40.

A user module 42 and one or more hardpanel controls 44 are operably coupled to patient support 10 to enable a person to electronically control one or more features of the patient support, including positioning of the bed or mattress, and activation or deactivation of therapy functions and other features of the bed or mattress. User module 42 has a display configured to show graphics 46 and touchscreen controls 48. In general, user module 42 includes a "dynamic" interface, meaning that the display including graphics 46 and controls 48 can change substantially in real time, as bed functions and features are activated, in progress, or deactivated, or as a patient's position or physiological status changes, for example. In general, hardpanel controls 44 are electromechanical switches such as membrane buttons or keys that may be depressed, turned or otherwise physically displaced to some degree, to activate or deactivate a bed function or feature.

In FIG. 1, user module 42 and hardpanel controls 44 are shown mounted to siderail 22. Alternatively or in addition, one or more user modules 42 and/or hardpanel controls 44 may be coupled to other barriers, such as siderail 24 or footboard 14, or may be coupled to patient support 10 by a mounting bracket, beam, or support, or may be positionable adjacent or alongside of patient support 10, such as on a service cart, support column, overbed table, or the like. One or more of controls 42, 44 may be wirelessly connected to patient support 10 and thereby movable remotely from patient support 10. For example, controls 42, 44 may be embodied in a portable housing that may be removably attachable to a caregiver such as by clipping to a labcoat, pocket, belt or waistband.

Figure 2:
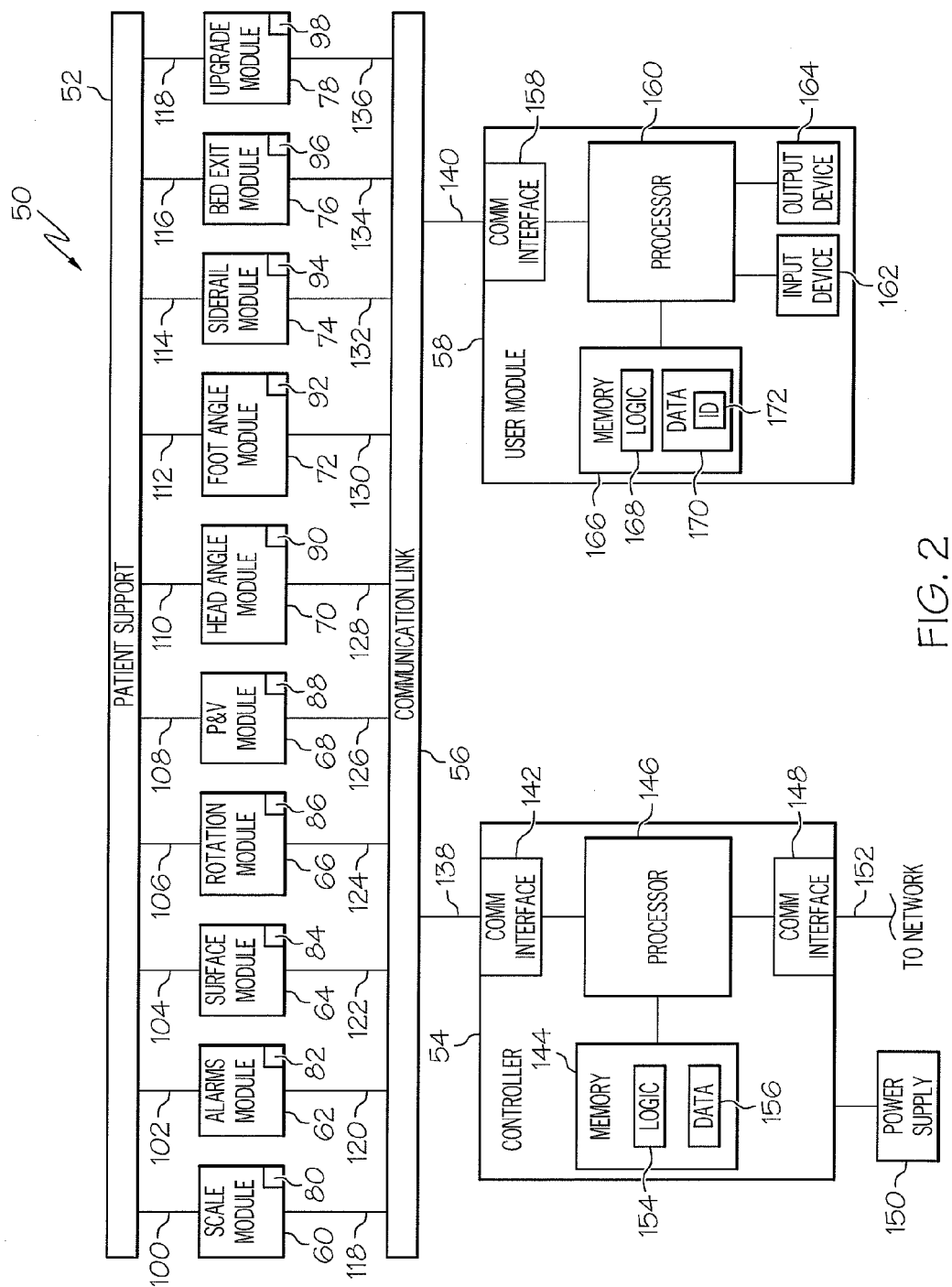
FIG. 2 is a block diagram of an architecture of a patient support apparatus including a patient support, a plurality of function modules, a controller and a user module.

FIG. 2 diagrammatically illustrates a control system 50 for a patient support 52 including many of the aspects of patient support 10 described above. The system 50 includes one or more function or feature modules 60, 62, 64, 66, 68, 70, 72, 74, 76, 78 operably coupled to patient support 52 and a main controller 54 via one or more communication links 56, and at least one user module 58.

The system 50 is configurable to add additional feature or function modules or remove existing feature or function modules as may be required according to a particular use of the patient support, usage setting (i.e. hospital, clinical or home environment), patient type (i.e., immobile, bariatric, ICU, maternity, etc.), or other parameters. In general, the term "module" describes programming logic embodying commands, data, and/or instructions relating to a feature or function of the bed or mattress. The programming logic is stored in a memory such as volatile or non-volatile computer memory. The memory may be included in an integrated circuit mounted on a circuit board or substrate, which may be coupled to or embedded in a physical component of the bed or mattress, such as a frame member, lift or articulating mechanism, barrier, mattress ticking, mattress interior component, or the like.

In general, memory as disclosed here and elsewhere herein may take the form of a permanent, temporary or portable storage device, recordable media or other components configured to retain information in digital form for some interval of time, and may include semiconductor-based integrated circuitry (such as flash memory), magnetic storage (such as hard disks), optical storage (such as CD disks), or the like.

As shown in FIG. 2, each of the function or feature modules 60, 62, 64, 66, 68, 70, 72, 74, 76, 78 is coupled to patient support 52 by electrical and/or mechanical couplings 100, 102, 104, 106, 108, 110, 112, 114, 116, 118 and is coupled to one or more communication links 56 by electrical and/or communication couplings 118, 120, 122, 124, 126 128, 130, 132, 134, 136. Mechanical couplings may include a mounting bracket, hook, strap, adhesive or other suitable mounting structure or fastener. Electrical couplings may include insulated wiring, fiber optics, wireless connection, or other suitable data, logic and/or power conduit. Communication couplings may include a hard-wired or network (wired and/or wireless) connection. Communication link(s) 56 are coupled to controller 54 via link 138. User module 58 may be coupled to controller by links 56 and 140 or link 140 may be directly coupled to controller 54.

In general, each function or feature module is configured to operate or control one or more predetermined features or functions of the bed or mattress. Each module includes a memory such as volatile or non-volatile computer memory, in which a module identifier is stored. The module identifier 80, 82, 84, 86, 88, 90, 92, 94, 96, 98 for each module is unique relative to all of the other modules coupled to the patient support 52, so that each module can be independently identified to the system 50.

Scale module 60 has a memory including programming logic to operate the patient weighing feature of the bed, including accepting user input from user module 58 relating to the "zero" or tare of the scale, or input relating to patient characteristics and the like. User input may be saved in the memory of the scale module 60. Scale module 60 may also have a processor, such as an embedded microprocessor, configured to perform certain operations locally at the module. Scale module 60 includes at least one communication interface for communicating data and/or instructional signals to and from controller 54 and/or user module 58.

Other feature or function modules are configured similarly to scale module 60 in that they have module identifiers and their own memory, software, and processors. Alarms module 62 includes programming logic and data to operate alarms and/or alerts associated with patient support 52, including a bed exit alarm triggerable by a patient exiting the bed or approaching a bed exit (e.g. positioned on the side or edge of the bed), a "siderail down" alert triggerable by lowering of a siderail alone or in combination with attempted activation or deactivation of another bed or mattress function or feature, a head or foot of bed angle alarm triggerable by the head or foot of bed angle going above, below or equaling a defined value or range of values, and nurse call, patient status, and "workflow" features such as may be provided by the Navicare™ patient flow system, the COMLinx®, OnSite™, and/or Vocera systems sold by the Hill-Rom Company, Inc. of Batesville, Ind. Alarms module 62 includes programming logic to automatically determine whether a particular patient support as configured includes any functions or features that have an alarm associated with them, and then provides a user interface to enable a caregiver or other user to configure the settings for the alarms and activate and deactivate the alarms.

Surface module 64 includes programming logic and data to operate certain therapeutic features of a patient support, such as turning assistance, maximum inflate, pressure redistribution, and the like. Rotation module 66 includes programming logic and data to operate a rotation therapy feature of the mattress that is often directed to relieving a patient's respiratory complications. Percussion and vibration module 68 includes programming logic and data to operate a percussion and vibration therapy feature of the mattress that is also often directed to relieving a patient's respiratory complications.

Head angle module 70 includes programming logic and data to monitor the head of bed angle via signals received from a sensor such as head angle sensor 36 and communicate information to alarms module 62. Head angle module 70 may also include logic configured to output data indicative of the head of bed angle or an audible or visual indicator thereof on an output device such as may be provided with user module 58. Similarly, foot angle module 72 includes programming logic and data to monitor the foot of bed angle via signals received from a sensor such as foot angle sensor 38 and communicate information to alarms module 62. Foot angle module 72 may also include logic configured to output data indicative of the foot of bed angle or an audible or visual indicator thereof on an output device such as may be provided with user module 58.

Siderail module 74 includes programming logic and data to monitor the position of a siderail coupled to the patient support 52 and communicate information to alarms module 62. Siderail module 74 may also include logic configured to output data indicative of the siderail status or an audible or visual indicator thereof on an output device such as may be provided with user module 58.

Bed exit module 76 includes programming logic and data to monitor the position of a patient relative to the bed, via signals received from one or more position sensors coupled to the bed or mattress. Bed exit module 76 communicates information to alarms module 62. Bed exit module 76 may also include logic configured to output data indicative of the patient position or an audible or visual indicator thereof on an output device such as may be provided with user module 58.

Upgrade and/or diagnostics module 78 includes programming logic and data to detect when an upgrade, fix, patch, new version or new release of programming logic associated with one of the other modules has become available, and provide audible or visual prompts to a service technician or other authorized person via a user module 58 to perform the upgrade. Alternatively or in addition, module 78 includes software to run diagnostic tests on other modules or components of the bed system, or on the bed system as a whole. Diagnostics software, upgrades, fixes, patches, new versions, new releases, and the like may be transferred or uploaded from a portable device such as a memory stick, which is connected to a communication port of the module 78, or via another suitable file transfer mechanism.

Controller 54 generally controls and coordinates the operation of the function or feature modules 60, 62, 64, 66, 68, 70, 72, 74, 76, 78 and interaction with the patient support 52 and user module 58. For these purposes, controller 54 includes a communication interface 142 operably coupled to communication link 56 via link 138, an embedded processor 146, a memory 144 including programming logic 154 and data 156, and a communication interface 148 to connect the system 50 to an external network 152 such as a telecommunications network.

A power supply or power conduit 150 may provide power directly or indirectly to controller 54. In general, power supply or conduit 150 includes a battery power supply and a connector configured to conduct power received from another source (such as a wall outlet), including power conversion components. Although not shown for simplicity, user module 58 and each of the function or feature modules 60, 62, 64, 66, 68, 70, 72, 74, 76, 78 generally includes a power supply or power conduit as well.

User module 58 is configured to enable a person to interact with, operate, configure and/or control the bed system 50 substantially in real time. For these purposes, user module 58 includes a communication interface 158 operably coupled to communication link 56 via link 140, an embedded processor 160, a memory 166 including programming logic 168, data 170, and a user module identifier 172, an input device 162 and an output device 164. Link 140 may be directly connected to controller 54 as mentioned above.

Input device 162 includes a touch sensor in the form of touchscreen controls. Output device 164 includes a liquid-crystal or similar display. In the illustrated embodiment, output device 164 includes a high pixel density (e.g. more than 640×480 pixel resolution) and high contrast screen and backlighting to improve visibility from various angles, and the touchscreen 162 is layered above the LCD display. In one embodiment, input device 162 and output device 164 are provided together as one device, such as models manufactured by Okaya Electric Industries Co., Ltd., of Tokyo, Japan or the OSD TN84 LCD and touchscreen. Alternatively or in addition, input device 162 may include a microphone, voice or sound recognition device, keypad, or membrane-style controls, and output device 164 may include a speaker, LEDs, or other like indicators.

Figure 3:
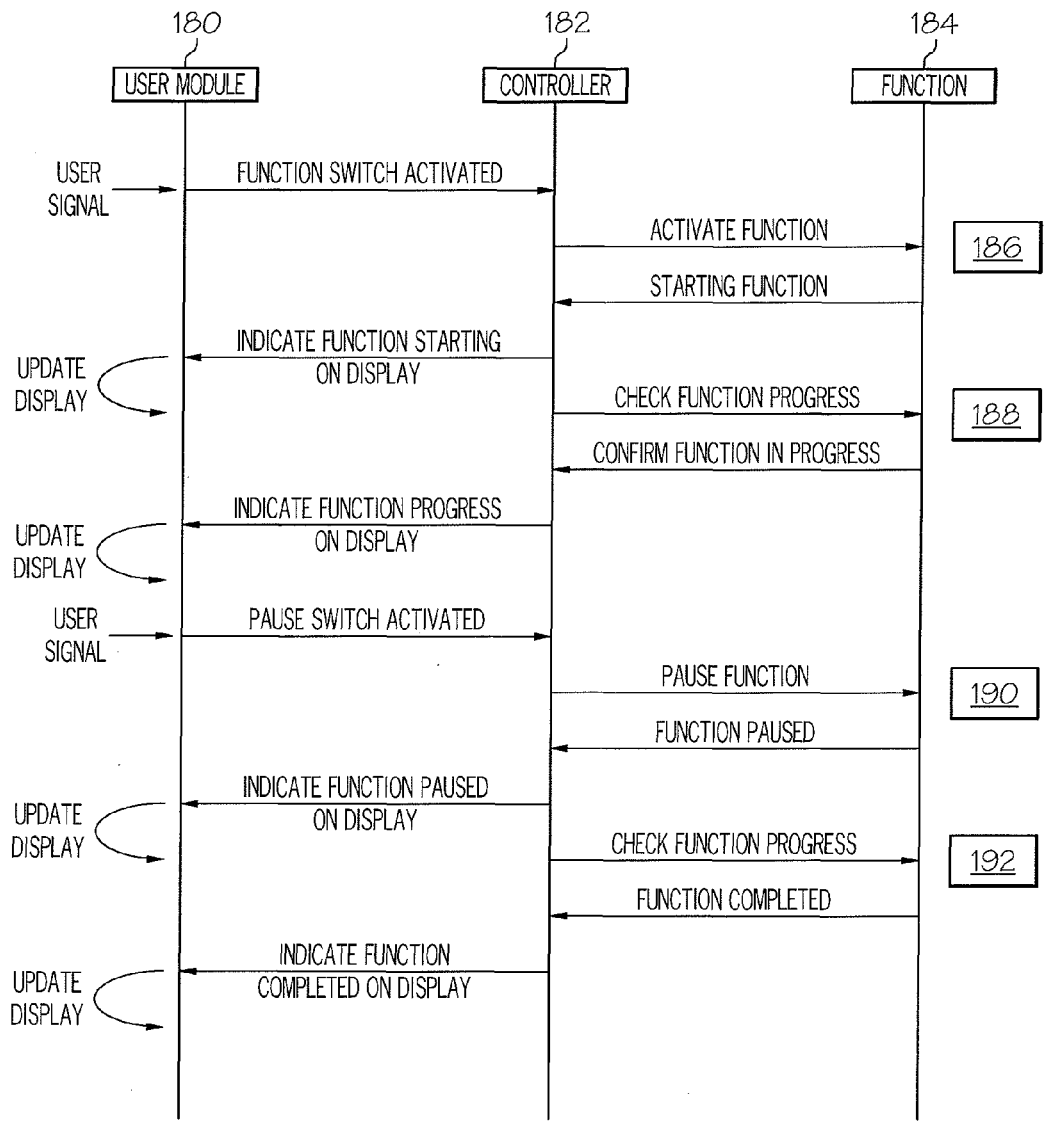
FIG. 3 is a timing diagram illustrating interaction between a user module, a controller, and one or more function modules of a patient support apparatus.

FIG. 3 is a high-level timing diagram showing interaction between a user module 180, a controller 182 and a function or feature module 184. User module 180, controller 182 and function or feature module are components of a patient support system generally configured as described above.

At block 186, user module 180 receives a signal from a user to activate a bed function or feature. The user signal may be the act of pressing a button, making contact with a touch-sensitive area of a user interface, saying a word recognized by the system, or other action taken by a user. User module 180 sends a message to the controller 182 identifying the selected bed function or feature and indicating that the selected function or feature is to be activated. Controller 182 determines the appropriate function module to activate, and sends an "activate function" message including a destination module identifier a function identifier to the designated function module 184. Function module 184 sends a message including its function identifier to controller 182 to indicate that the selected function is being activated. Controller 182 then sends a message to user module 180 including the function identifier to indicate via an output device that the selected function has been activated. User module 180 then generates the appropriate output.

In the illustrated embodiment, the output is a visual indicator such as a textual message or graphical illustration, but it could alternatively or in addition include an audible indicator or a message sent to a remote device (such as through a nurse call system). The graphical illustration may include an animated graphic that is designed to simulate motion or movement of the patient support resulting from activation of the selected function, to convey the information to a caregiver or user without using language.

At block 188, the controller 182 sends a message periodically to the function module 184 to check the progress or status of the selected function, and the function module 184 returns a progress or status message including the function identifier to the controller 182. Upon receiving the progress or status message from the function module 184, controller 182 sends a message to user module 180 to provide an indication of the function's status or progress to the user. User module 180 determines the appropriate indicator to output based on the function identifier and then updates the output device. In the illustrated embodiment, a visual indicator is updated on a display. For example, a "thermometer"-style graphic may be presented, graphically showing the level of completion of the selected function by filling in the amount completed with a contrasting color or shade. Alternatively or in addition, a textual message such as "In Progress" is displayed.

At block 190, user module 180 receives a signal from a user to pause the selected bed function or feature. The user signal may be the act of pressing a button, making contact with a touch-sensitive area of a user interface, saying a word recognized by the system, or other action taken by a user. User module 180 sends a message to the controller 182 indicating that the "pause" feature has been activated by a user. Controller 182 determines the proper function module to receive the pause signal and sends a message to the function module 184 with instructions to at least temporarily suspend performing the selected function. Function module 184 returns a message to controller 182 including the function identifier, when the selected function has been paused, and controller 182 sends a message to the user module 180 including the function identifier to give an indication to the user that the selected function is paused. User module 180 then updates the output device. In the illustrated embodiment, a visual display is updated. For example, a "pause" button is converted to a "resume" button after the function has been paused by replacing the word "pause" with the word "resume." Alternatively or in addition, the color of the button changes from a first color or shade to a second color or shade (such as from red to green).

At block 192, controller 182 checks the progress or status of the selected function by sending a message including a function identifier to function module 184. If the selected function has completed its operation, function module 184 returns a "completed" message to controller 182. Controller 182 then sends a message to user module 180 to instruct it to update its output to indicate that the selected function has completed its operation. User module 180 then updates its output relating to the selected function. For example, the "thermometer" described above may be completely filled in with a contrasting color or shade, or a text message may be updated from "In Progress" to "Completed". Alternatively or in addition, a "stop" button may be converted to a "start" button and the color or shade of the button may change from a first color or shade to a second color or shade (i.e. red to green), to visually indicate without using language that the function is ready to be selected again.

Figure 4:
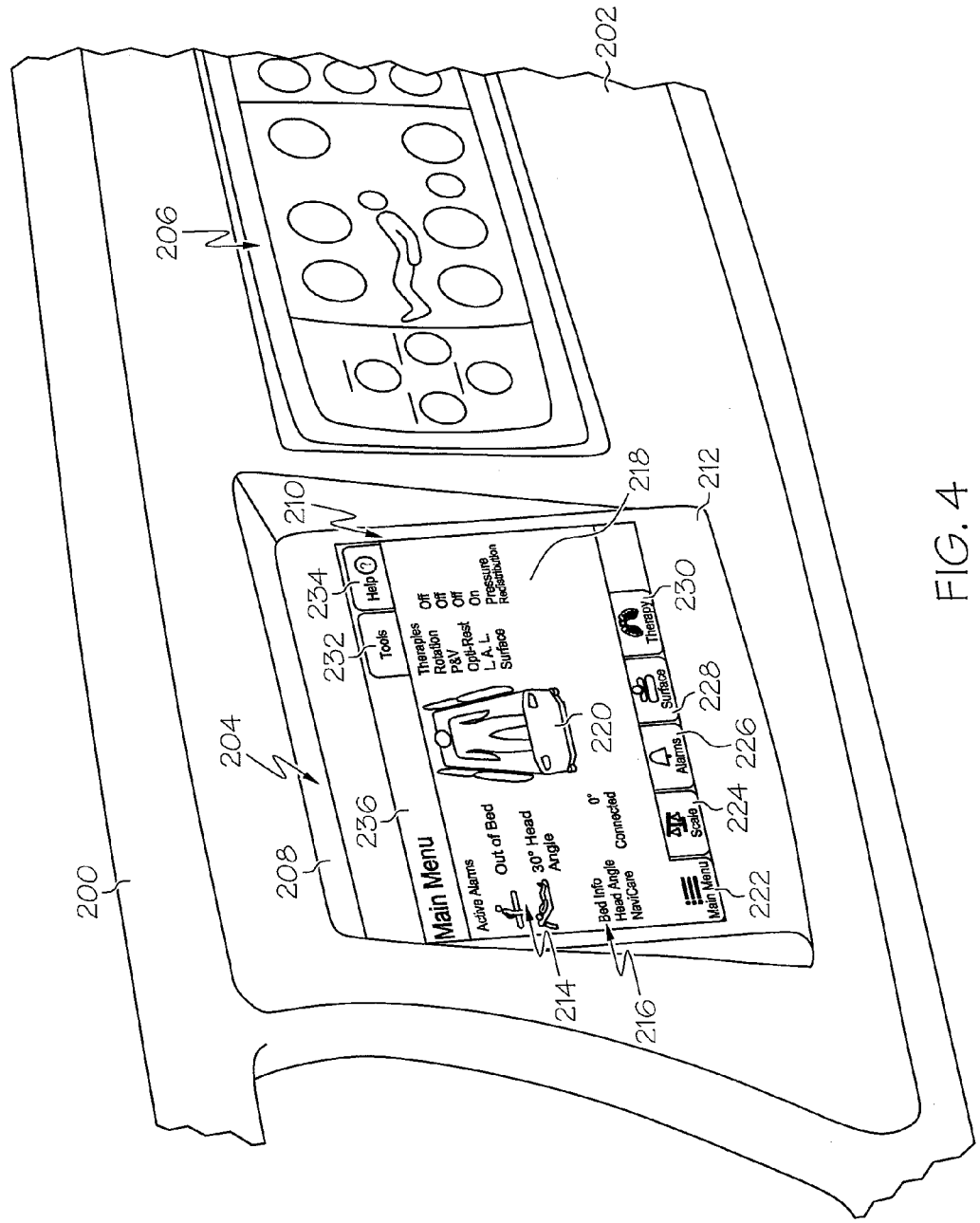
FIG. 4 is perspective view of a user module mounted at an angle in a siderail adjacent a region of the siderail that includes hardpanel controls, where the user module has a graphical user interface including a graphical display region, text display regions, highlighting, and user controls.
Figure 31:
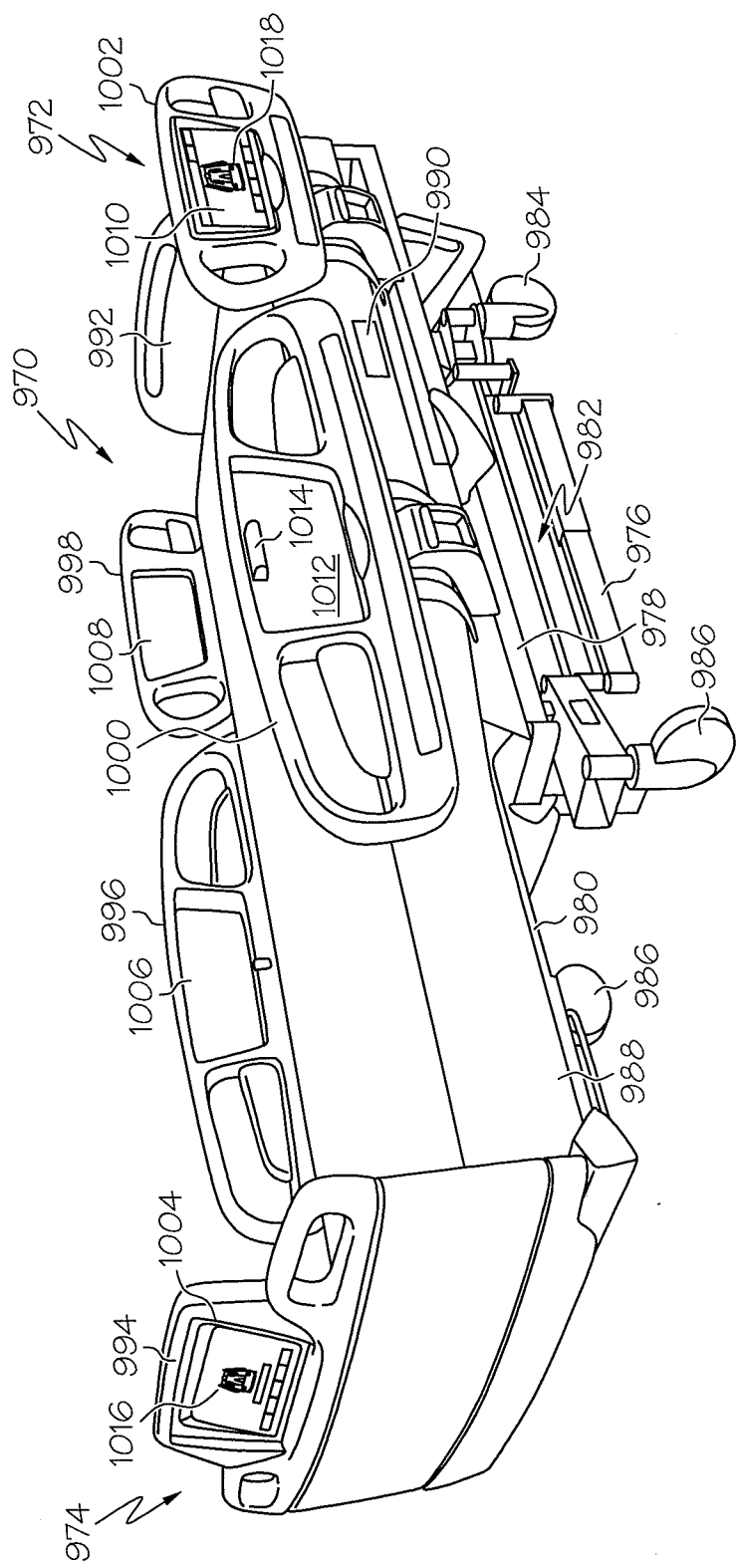
FIG. 31 is a perspective view of a patient support including multiple user modules and docking regions for the user modules on the patient support.

FIG. 4 illustrates a portion of a siderail 200 with a user module 204 mounted at an angle, creating a recess 208 from panel 202. Hardpanel controls are positioned on panel 202 adjacent user module 204. User module 204 includes a display 210 supported by a housing 212. Housing 212 is constructed of molded plastic or similarly suitable material. Housing 212 is coupled to siderail 200. Housing 212 may be molded in siderail 200 such that it is an integral part thereof. In other embodiments, such as shown in FIG. 31, housing 212 may be pivotably coupled to siderail 200 and/or entirely removable from siderail 200, to be used as a portable or handheld device, for example.

Display 210 includes a first dynamic region 214, a second dynamic region 216, a third dynamic region 218, a fourth dynamic region 220, touchscreen controls 222, 224, 226, 228, 230, 232, and 234, and a fifth dynamic region 236.

In the illustrated embodiment, first dynamic region 220 is an informational status area indicating the current status of alarms that have been set or enabled. Region 220 includes a title line ("Active Alarms"). Below the title line, information is displayed if one or more alarms have been set by the caregiver. If no alarms have been activated, the area under the title line appears "blank". If, as shown, the "out of bed" alarm is activated, a graphical icon indicative of a person standing next to a bed and a textual "out of bed" message is displayed in region 220. If, as shown, the "30 degree head angle" alarm is activated, a graphical icon indicative of a person lying on a bed with the head of bed elevated to 30 degrees and a textual "30 degree head angle" message is displayed in region 220. Other active alarms are similarly displayed.

Second dynamic region 220 is an informational status area indicating the current status of the bed. In the illustration, a horizontal text line is provided for each bed status indicator, and for each indicator, a textual description is followed by the current data value for that indicator set off in bold type, contrasting color, or the like. For example, as shown in FIG. 4, the text "Head Angle" is followed by the current actual value of the head of bed angle, displayed in degrees in bold type. Also, as shown, if the bed is connected to an external system or network (such as the NaviCare™ system), the same is indicated in region 220.

Third dynamic region 218 is an informational status area indicating the current surface status or status of available therapies, such as "Rotation," percussion and vibration ("P&V"), "Opti-Rest," airflow or "low air loss" ("L.A.L."), and "Surface" (pressure redistribution). In the illustration, a horizontal text line is provided for each therapy indicator, and for each indicator, a textual description is followed by the current data value for that indicator set off in bold type, contrasting color, or the like. For example, as shown, the text "Rotation" is followed by the current actual status of the rotation therapy ("Off"), displayed in bold type.

Dynamic region 220 includes a graphical representation of a patient positioned on a patient support including a surface, a patient positioned on the surface in the supine position, siderails, and a footboard. Portions of this graphical representation may become animated in response to activation or deactivation of certain functions, as described below. The illustration of region 220 shown in FIG. 4 represents the bed and patient graphic as displayed when neither the rotation nor the percussion and vibration therapies are active.

Touchscreen controls 222, 224, 226, 228, 230 are in the form of function tabs positioned along the lower portion of the display and include both a brief text description of the function and a graphical icon illustrative of the function that may be selected. Controls 232, 234 are generally used less frequently than controls 222, 224, 226, 228, 230 and are therefore positioned in another part of the display as shown. Each control corresponds to a main function or feature of the patient support. The user can quickly switch between functions or features by activating (e.g. by contact) the tab associated with the next desired function or feature. The currently active function tab is set off from the others by a contrasting color or shade. In the illustration, the "main menu" tab 222 is lighter in shade than the other tabs because the "main menu" screen is currently displayed. The title of the currently active screen is also displayed in textual form at region 236.

One or more of hardpanel controls 206 may be configured as a "hotkey" or "hotbutton" to cause a change or result on the touchscreen display 204. For example, to conserve power, display 204 "times out" (backlighting is turned off) after a period of time. A first hardpanel control 206 is configured so that when depressed by a user, the backlighting of display 204 is turned back on to "reactivate" a display. As another example, there are certain bed movement functions that are automatically disabled based on certain conditions of the bed. For example, if the siderails are down, the bed may not be able to be moved into "chair" position and rotation therapy may be disabled when any of the siderails are down.

A second hardpanel control 206 is configured to automatically put the bed into the chair position. However, if the siderails are down, a pop-up window is displayed on the display 204 informing the user that the siderails need to be raised before the bed can go into chair position. In this way, hardpanel controls 206 may act as an input device 162 by being configured to send input to processor 160, and output device 164 may be configured to display output relating to input received from hardpanel controls 206 and processed by processor 160. Alternatively or in addition, with reference to FIG. 2, display 204 may be considered to be a first user module 58 and hardpanel controls 206 may be considered to be second user module 58, and the modules 204, 206 may communicate over a link 56.

FIG. 5 depicts a user interface 250 for a patient weighing function of a patient support. In general, a patient support may be configured to weigh a patient positioned thereon. Illustratively, the patient support may include a weigh frame and a plurality of load beams or cells coupled to the weigh frame. In such event, a scale module 60 is provided. Scale module 60 receives signals from the load cells and determines a weight therefrom. Scale module 60 outputs a signal representative of the weight to a controller or network, to be displayed at the user module, transmitted to a remote device, or other purpose.

Interface 250 includes instructional text 252, a graphical representation of a patient's weight history over time 254, a non-text communicative element 256, selective highlighting 258, a "weigh patient" touchscreen control 260, a "zero scale" touchscreen control 262, an "adjust weight" touchscreen control 264, a "kg/lbs" touchscreen control 266, and a "view history" touchscreen control 268 for viewing the history of a patient's weight. Scale tab 270 is set off in contrasting coloring or shading to indicate that it is active as shown.

The instructional text 252 is dynamically updated according to functions or features selected by the user. The data area 258 is selectively set off with "highlighting," i.e. a perceptively different coloration or shading, such as bright yellow, to direct the user's attention in a non-textual way to the data presented therein. The communicative element 256 is shown as a "down arrow" to indicate in a way that does not involve language interpretation that the patient has lost weight during a period of measurement. The time period of measurement may be pre-selected or user-configurable. In the illustrated embodiment, the time period is shown as 24 hours.

The graphical representation 254 is, in the illustration, a line graph displaying the patient's weight over a period of time. The weigh patient button 260 is set off from the others by selective coloration, i.e. using a perceptively different color or shading to fill in the button. The functions and features of the controls 260, 262, 264, 266, 268 are described below.

It may be desirable to obtain a patient's weight in a variety of treatment and/or therapy circumstances. Certain protocols may require the patient's weight to be obtained before an automated bed function or therapy feature can be activated, such as such as automated pulmonary therapies including rotation and percussion and vibration.

Figure 6:
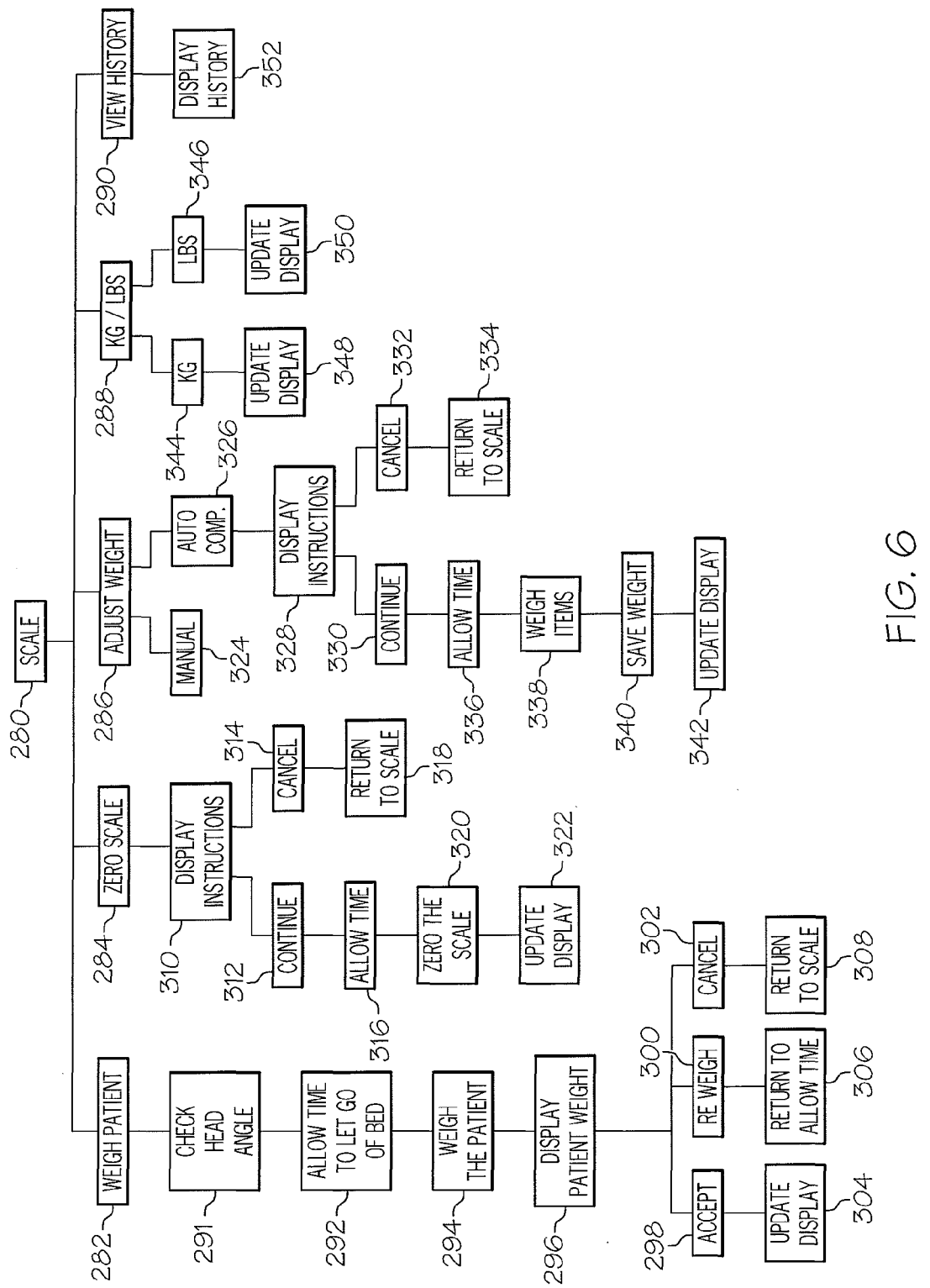
FIG. 6 is a diagram illustrating steps in the operation of the weigh scale features including weighing a patient, zeroing the scale, adjusting the weight, converting the weight from kilograms to pounds, and viewing a patient's weight history.

FIG. 6 shows diagrammatically a progression of steps to perform the functions made accessible to the user by the Scale menu 250, represented by scale block 280 in FIG. 6. Selecting the weigh patient button 260 to obtain a patient's weight is represented by weigh patient block 282.

At block 291, the system checks the head angle of the patient support. If the head angle is already less than or equal to 30 degrees, the system proceeds to function block 292. If the head angle is greater than thirty degrees, the system prompts the user to lower the head angle before proceeding. In some embodiments, an option may be provided to override the head angle check and proceed to weigh the patient even if the head angle is greater than or equal to thirty degrees.

At block 292, the bed system allows the caregiver an amount of time to let go of the bed after selecting the function (i.e., so that contact with the bed does not affect the weight reading).

Also, if the system detects that the head angle is above 30 degrees and/or the deck is not in a flat position, a pop-up window is displayed to inform the user that more accurate results may be obtained if the head section of the bed is lowered below 30 degrees and the deck is in a flat position. The system allows the user time to lower the head section and/or reposition the bed.

Further, percussion and vibration therapy is active, the system will not allow the patient weight to be taken until the therapy is paused or stopped. In addition, if a patient is positioned on the patient support but not weighed after a period of time has elapsed, the system will inform the user by displaying a message and/or graphic on the display and give the user an option to weigh the patient, indicate that the bed is empty, or to set a reminder to be prompted again after a further period of time elapses.

After the time has expired, which may be represented on the display by a "countdown," or the user indicates it is "ok" to weigh the patient, or the system detects that the bed is in an appropriate condition or state to weigh the patient, the system proceeds to weigh the patient at block 294. At block 296 the numerical value of the patient's weight is displayed, at which point the user may choose to accept the weight value at block 298, re-weigh the patient at block 300 or cancel out of the weighing function at block 302. If the patient's weight is accepted, the weight value is saved into memory and the display is updated at block 304. If the re-weigh option is selected, the system returns to function block 292 to repeat the process. If the cancel option is selected, the system returns to the main scale block 280.

Selecting the zero scale button 262 is represented by the zero scale block 284 of FIG. 6. In general, zeroing the bed scale provides a baseline reading against which future weights can be compared. At block 310, instructions for zeroing the scale are displayed. These instructions may include reminding the user that the bed should not be occupied and that standard linens and other items should be placed on the bed before zeroing. After the user indicates "ok" at block 312, the system allows time to let go of the bed at block 316, and then the system proceeds to zero the scale at block 320 and update the display with the zeroed information at block 322. The user may decide to cancel the operation at block 314, in which case the system returns to scale block 280.

Scale module 60 also includes programming logic to detect when the patient support is equipped with a pulmonary therapy module, such as percussion and vibration or rotation therapy modules. As these modules add extra weight to the bed, scale module 60 automatically re-calculates the zero weight value if one or more of these modules is present.

After zeroing the bed scale, it may be desirable to have the patient support automatically adjust the patient's weight to take other items into consideration, such as additional support pillows, blankets, equipment, and the like that may be connected to the patient but which are not part of the patient support. In such case, scale module 60 may be configured to automatically adjust the patient's weight value to account for such items.

Figure 7:
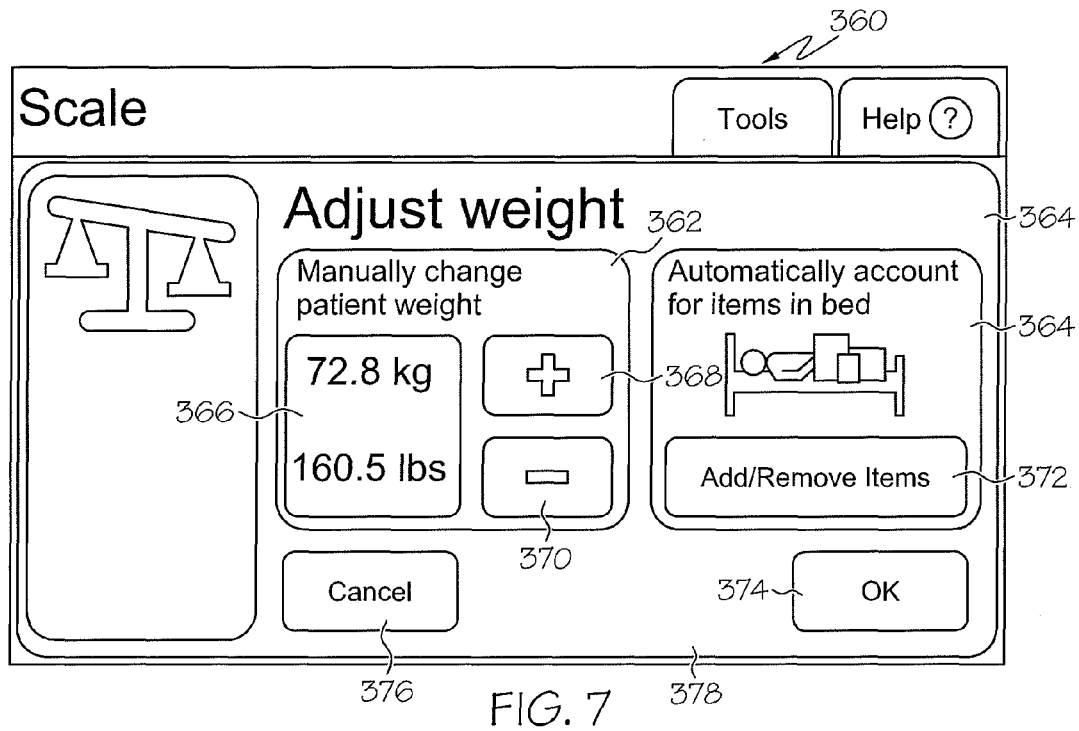
FIG. 7 is a screen shot of a user interface for an adjust weight feature of a patient support, including graphical icons, text, selective highlighting, and user controls relating to an option to manually change a patient's weight and an option to automatically account for items in the patient's bed when weighing the patient.

Selecting the adjust weight button 264 is represented by the adjust weight block 286. As shown in FIG. 7 described below, the user may manually adjust the patient's weight by pressing plus or minus buttons 368, 370, at function block 324 of FIG. 6.

An "automatic compensation" feature is also provided, as shown by region 364 and control 372 of FIG. 7, at function block 326 of FIG. 6. This feature allows the weigh scale to be customized for individual patient needs. When the "add/remove items" button 372 is selected, the system informs the user that it will weigh or re-weigh the patient before additional items can be added or removed. Such items may include therapy devices, IV poles, or other items that an individual patient may normally have with them on the bed and that may affect accurate weighing.

Figure 8:
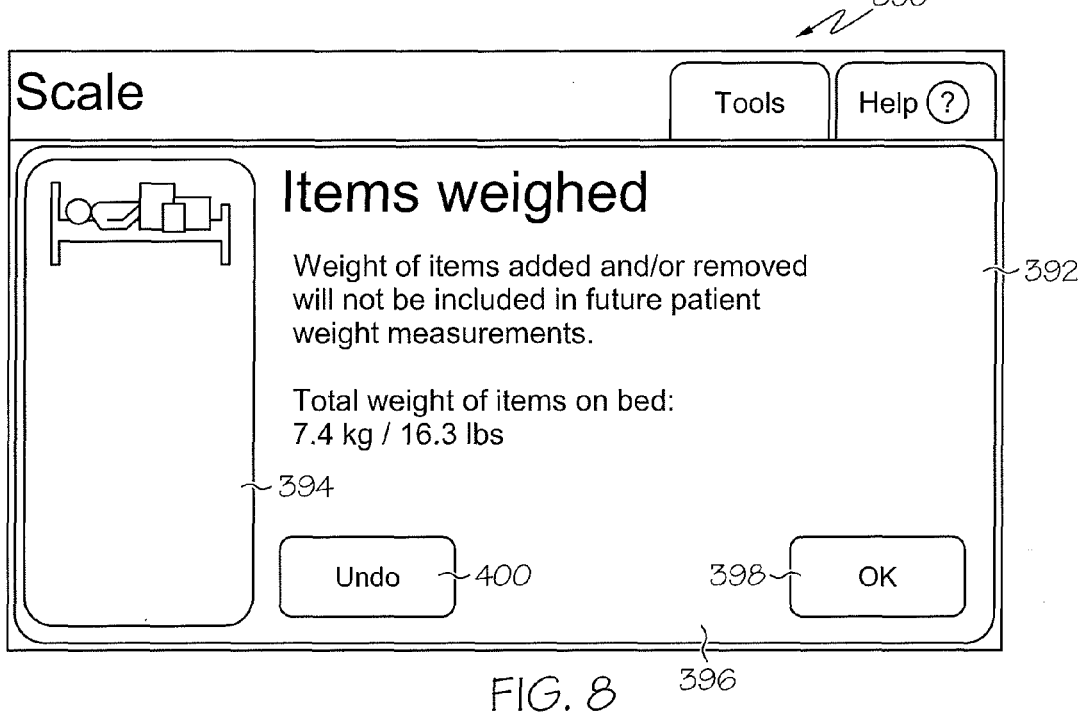
FIG. 8 is a screen shot of a user interface including information relating to the automatic weight adjustment feature, a graphical icon, selective highlighting, and user controls.

Once the patient is weighed, the system prompts the user to add or remove those items to/from the bed and weighs the items at block 338. The system then informs the user of the new weight including the items added or removed as shown in FIG. 8. The user may opt to save the weight at block 340 by pressing button 374 in which case the display is updated to inform the user that such items will be discounted from the patient's weight in the future, thereby enabling a caregiver to obtain an accurate weight of the patient without having to add or remove the patient's items from the bed each time.

The "kg/lbs" function at block 288 allows the user to switch between methods of measurement, selecting either kilograms or pounds. The "view history" function at block 290 allows the user to view a graphical representation of the patient's weight values over time. The patient's weight history is displayed in the form of a bar graph or line graph, similar to FIGS. 28 and 29, described below, at block 352.

Figure 9:
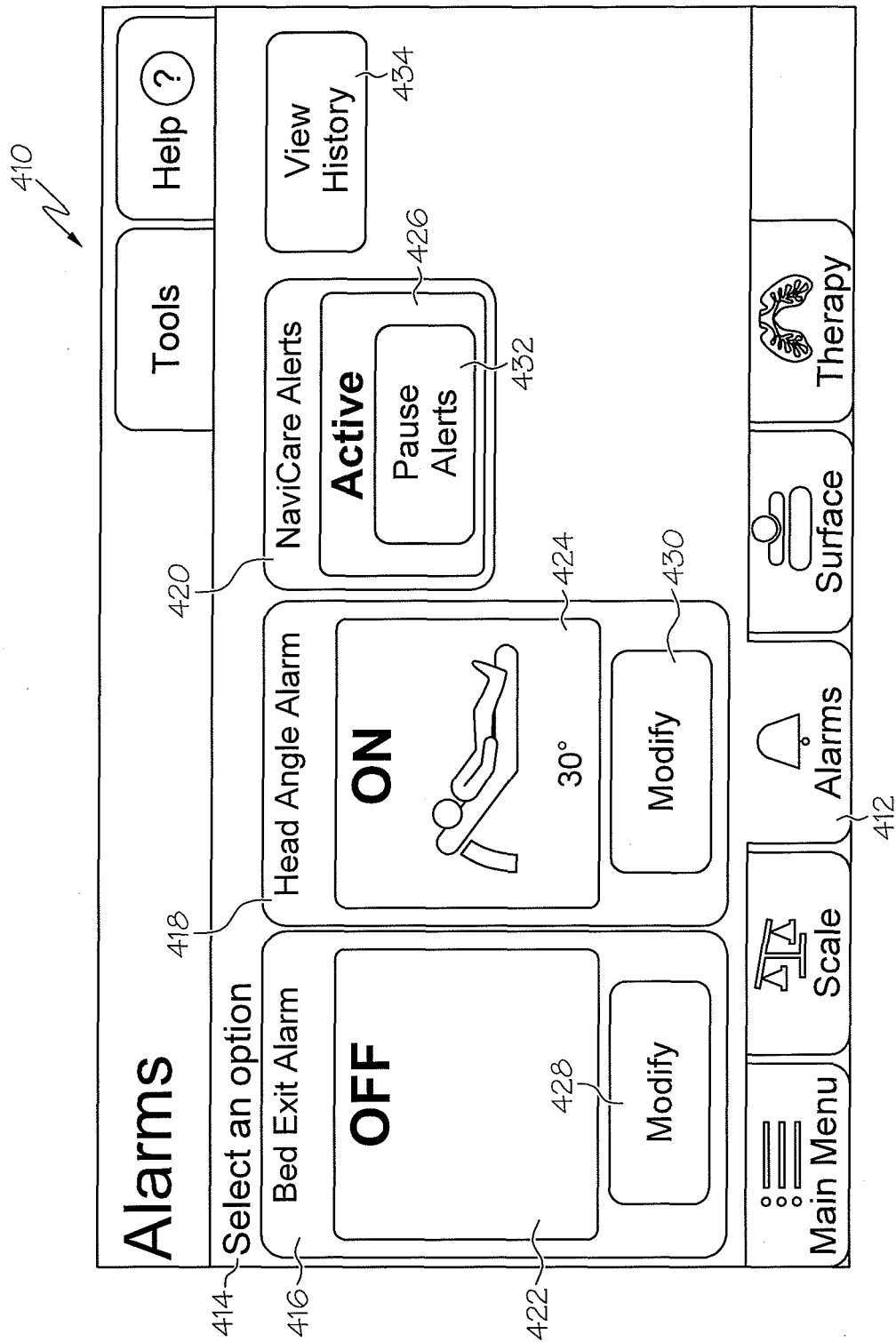
FIG. 9 is a screen shot of a user interface for alarms features of a patient support, including text, graphics, selective highlighting and user controls for a bed exit alarm, a head angle alarm, work flow alerts, and viewing a patient's history of alarms.
Figure 10:
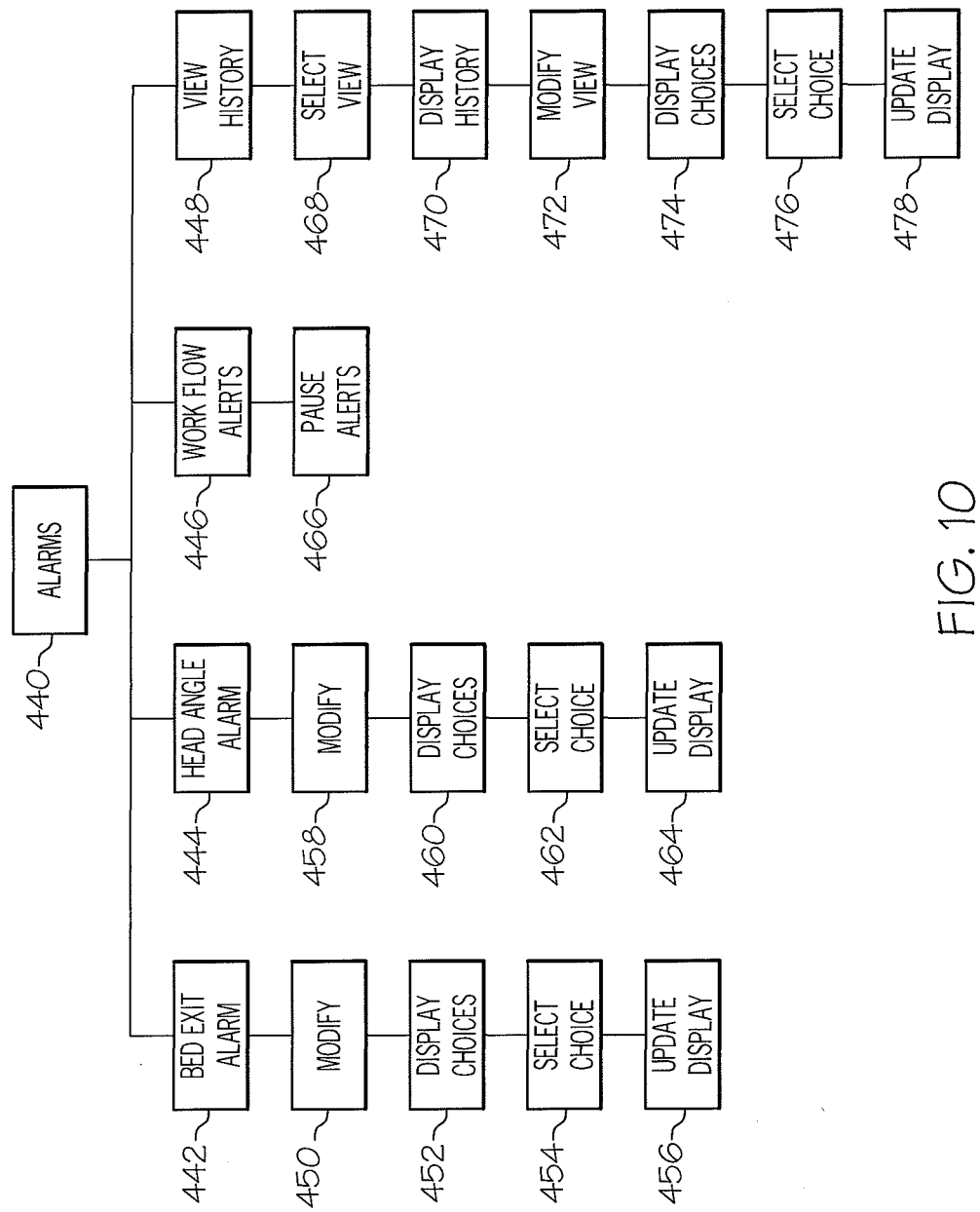
FIG. 10 is a diagram illustrating steps in the operation of the alarms features including a bed exit alarm, a head angle alarm, work flow alerts, and viewing a patient's history of alarms.

FIGS. 9 and 10 relate to alarm features of a patient support. FIG. 9 depicts a main user interface 410 from which a user may select an alarm option to configure. Main alarm screen 410 is represented by function block 440 of FIG. 10. In the illustration of FIG. 9, the alarms function tab 412 is offset by a contrasting color or shade from the other function tabs to indicate nontextually that the alarms screen 410 is active.

In the illustration, alarms that may be configured include a bed exit alarm 412, a head angle alarm 444, and work flow (illustratively: NaviCare™) alerts 446. Additional alarms may be added or may be substituted in place of one of these alarm features by upgrade module 78. Bed exit alarm 412 may be set to activate an alarm or alert if the system detects a patient exiting the bed. The alarm may alternatively or in addition activate an alarm if a patient is sitting up in bed, on the edge of the bed, or already out of the bed. Head angle alarm 444 may be set to detect when the head of bed angle is above or below a certain value or range of values, and generate a notification when the condition is met.

The alarm screen 410 of FIG. 9 includes a brief textual instruction 414, a first display and input region 416, a second display and input region 418, a third display and input region 420, and a "view history" user control. First display and input region 414 is set off from the other areas of screen 410 by highlighting or selective coloration, as are regions 418 and 420. Each of regions 416, 418, 420 includes a data/status region 422, 424, 426 in which current data relating to the alarm feature is displayed.

For example, in the bed exit alarm region 416, the word "off" is displayed when the bed exit alarm has not been activated. If the alarm is activated, the word "on" is displayed, and a graphical representation of a person exiting a bed may also be displayed. In the head angle alarm region 418, the word "on" is displayed when the head angle alarm has been set or enabled and a graphical depiction is also used to communicate that information without use of words. The numerical value of a head angle currently associated with an alarm (e.g., 30 degrees) is also displayed. In region 426, the current status of the work flow alerts (i.e., "active") is displayed in text form but also could be depicted graphically.

Each of regions 414, 418, 420 also includes a touchscreen control 428, 430, 432, respectively, to modify or change parameters associated with the alarm or in the case of region 426, to pause or at least temporarily suspend the alerts. Referring to FIG. 10, activation of the "modify" or "change" function 450, 458 results in discrete choices being displayed for selection by the user (blocks 452, 460). For example, if modify button 430 is activated to configure a head of bed angle alarm, the discrete choices may relate to the numerical value or range of values of the angle associated with the alarm, such as 30 degrees, 45 degrees, less than 30 degrees, greater than 30 degrees, greater than 45 degrees, etc. If modify button 428 is activated to configure a bed exit alarm, the discrete choices may include out of bed, edge of bed, sitting up in bed, and the like.

The NaviCare™ system and other similar systems connect and monitor powered beds, patient supports and surfaces by sending bed and surface data to network applications for caregivers to view and receive alerts at a nurse's station. The work flow alerts feature 420 of the patient support enables a caregiver or other user to pause or at least temporarily suspend the work flow alerts directly at the bedside of the patient. As an example, if the user activates the work flow alerts by pressing alerts button 432, then status information from the patient support will be communicated to the nurse's station over a network through the work flow or bed status system. For instance, if the head of bed angle is lowered below 30 degrees, an alert may be generated and sent to the nurse's station. It may be desirable to a caregiver to be able to temporarily suspend the sending of these types of messages to a nurse's station, for example while a patient is receiving a treatment, diagnostic test, is exiting the bed for therapy or other reasons, or the like. Pressing the pause alerts button 432 may thereby enable a caregiver to eliminate unnecessary nurse calls due to changes in the bed's status that are part of the patient's normal routine, for example. As a result of feature 420, the caregiver does not need to exit the patient's room to turn off or disable the alerts at a nurse's station. Instead, the caregiver can pause the alerts right from the patient's bedside.

Alarms module 62 includes programming logic to automatically detect whether the bed position, status or conditions are appropriate before activating a selected alarm. For example, if the actual head of bed angle is lower than about 30 degrees, alarms module 62 will prompt the user to raise the head section of the bed before the head of bed angle alarm can be set. Alarms module 62 continues to monitor the bed position, status and conditions after an alarm is set and/or while another bed function, feature or therapy is in progress. For instance, an automated rotation therapy may be stopped or at least temporarily suspended if the head of bed angle is above about 40 degrees and/or the foot of bed angle is below about 30 degrees. In addition, if a user desires to start an automated rotation therapy while an automated percussion and vibration therapy is already active, the system will display a pop-up window prompting the user to decide whether to continue and may at least temporarily pause the percussion and vibration therapy. Likewise, if a user desires to start an automated percussion and vibration therapy while an automated rotation therapy is already running, the system will display a pop-up window prompting the user to decide whether to start the percussion and vibration therapy and may at least temporarily pause the rotation therapy.

In these and similar cases, alarms module 62 will issue pop-up windows containing alert messages and/or graphics to communicate with the user. Alarms module 62 includes programming logic configured to color-code messages according to severity or type of message. For example, a message that is printed in a first color (such as blue) or presented against a first background color (e.g. blue) may be primarily informational in nature. A message that is displayed in a second color (such as yellow) or displayed against a second (e.g. yellow) background color may indicate a possible safety issue or indicate a possible bed limitation or unsafe condition relating to the patient support. A message that is printed in a third color (such as orange) or displayed against a third (e.g. orange) background color may indicate a safety issue relating to the patient.

Figure 28:
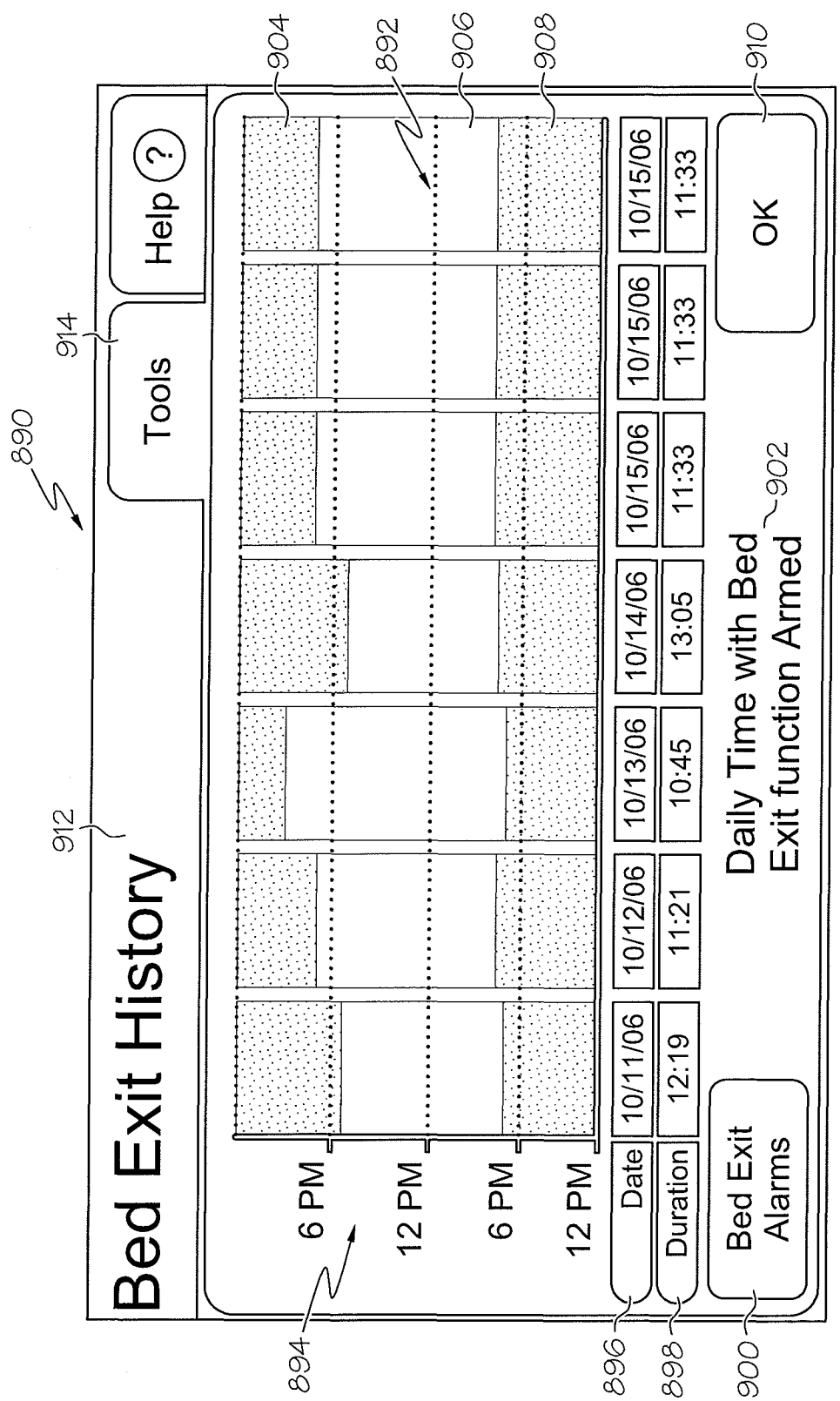
FIG. 28 is a screen shot of a user interface for displaying information relating to a bed exit alarm of a patient support, including text, graphical elements, selective highlighting, and user controls.
Figure 29:
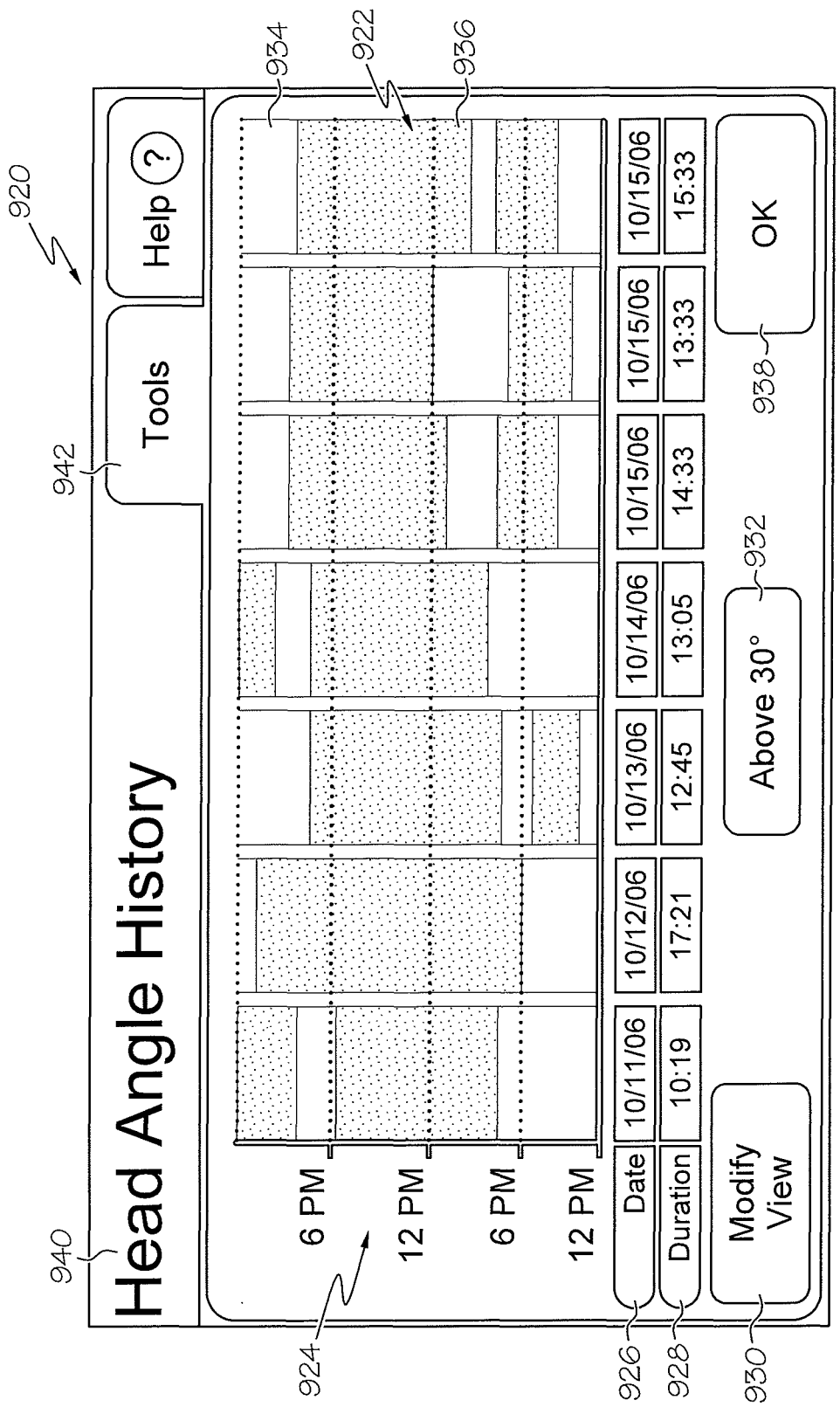
FIG. 29 is a screen shot of a user interface for displaying information relating to a head angle alarm of a patient support, including text, graphical elements, selective highlighting, and user controls.
Figure 30:
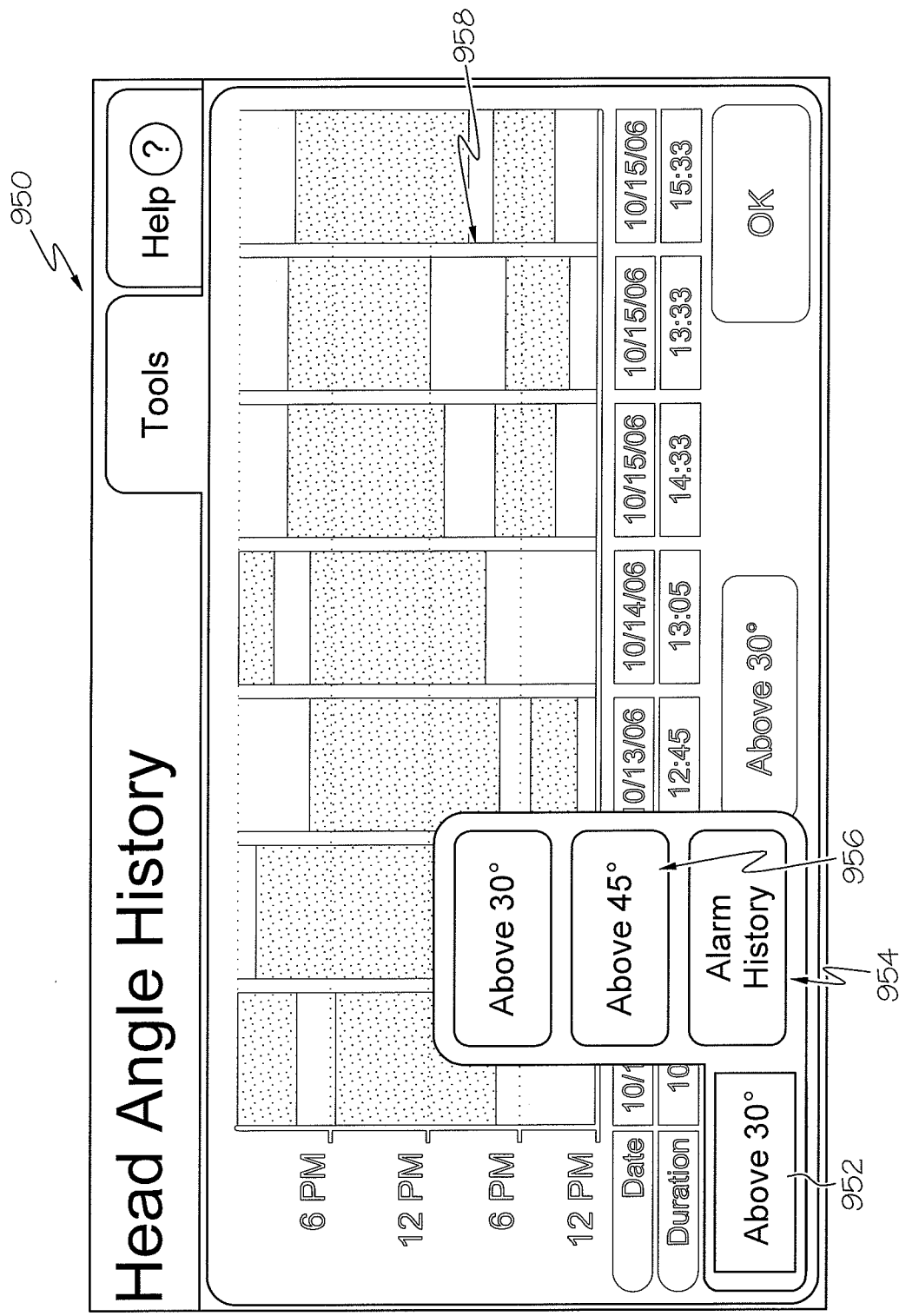
FIG. 30 is a screen shot of a user interface for configuring settings relating to a display of information relating to a head angle alarm, including text, graphical elements, reverse highlighting, and a one touch pop up input region.

Steps associated with the view history button 434 are depicted in FIG. 10 beginning with block 448. Examples of alarm history reports are shown in FIGS. 28-30. The reports may be configured by the user at the select view block 468, in which the date range, time of day, and duration scales may be adjusted (i.e. the "x" axis and "y" axis). The patient's history data is displayed according to the selected view criteria at block 470 in the form of a bar graph or line graph. While viewing the graph of the data, the user may modify the view parameters at block 472, at which point the system displays the choices of parameters that can be modified at block 474, urges the user to make a selection at block 476 and updates the display according to the modified selections at block 478.

FIG. 11 depicts a main screen 490 for configuring surfaces related features and functions of a patient support. As described above, function tab 492 is offset by contrasting color or shading to indicate nonverbally that the surfaces screen is active. Also as described above, a brief instructional text 494 is provided, main function or feature areas or control regions 496, 498, 500, 502 are offset from each other by selective coloration or highlighting, and touchscreen controls 504, 506, 508, 510, 512 are provided in each control region. Text and graphical icons are provided to quickly direct the user's attention to the desired function.

Functions configurable by surface screen 490 are shown in FIG. 12 and include maximum inflation 522, opti-rest 524, turning assistance—patient right 526, turning assistance—patient left 528, seat deflate 530, reminder 532 and low air loss 534.

For example, a graphical representation of a person positioned on a maximum-inflated surface is associated with the max-inflate control region 496 and a downwardly pointing arrow above the seat section is associated with the seat deflate feature 510. In general, the automated max-inflate module 522 may be activated to help facilitate changing a patient's position on the support surface or transfer of the patient to another surface (such as a stretcher or operating room table).

With regard to the turning assistance features 506, 508, the feature is configured with reference to the patient, i.e., "patient right" and "patient left". In general, the automated turning assistance modules 526, 528 may help facilitate linen changes or wound inspection by facilitating rotation of a patient onto his or her side. Graphical representations aid the caregiver in quickly determining which of the controls 506, 508 is associated with each side of the patient. The clear and succinct indication of the point of reference may help reduce potential confusion and resulting mistakes.

Selective coloration may also be used in the user controls. For example, the "start opti-rest" control 512 is filled in with a first suggestive color, i.e., green for "go". If the button 512 is activated, the text changes to "stop opti-rest" and the filling changes to a second suggestive color, i.e. red for "stop". In general, activation of the "opti-rest" module 524 causes the patient support surface to automatically repeat a cycle of varying the pressure underneath a patient's chest, seat and thighs, producing a wave-like motion.

In general, seat-deflate module 530 includes programming logic to selectively deflate the seat section of the patient support surface, to help facilitate side ingress and egress or for other reasons. Low air loss module 534 generally includes programming logic to provide air circulation underneath a patient positioned on the patient support.

The "remind me" button 514 enables configuration of a caregiver reminder feature of the patient support, wherein a caregiver may schedule the patient support system to issue a reminder to the caregiver to activate or deactivate a therapy or other bed or mattress function or feature. For example, a reminder may be configured to remind the user to repeat a therapy function (such as weighting a patient, performing turning assistance, or performing an automated pulmonary therapy) after a period of time that may be pre-defined or selected on the fly by the user, or to remind the user to repeat, start or stop a function, feature or therapy before or after a certain amount of time has elapsed (as may be desirable in the case of percussion and vibration therapy). Such a reminder may be sent by the bed through a network to a wireless communication device (e.g., PDA, Vocera badge, wireless telephone handset or the like, carryable by a caregiver, as described in U.S. Patent Application Publication No. 2006-0049936 A1, incorporated herein by this reference).

Figure 13:
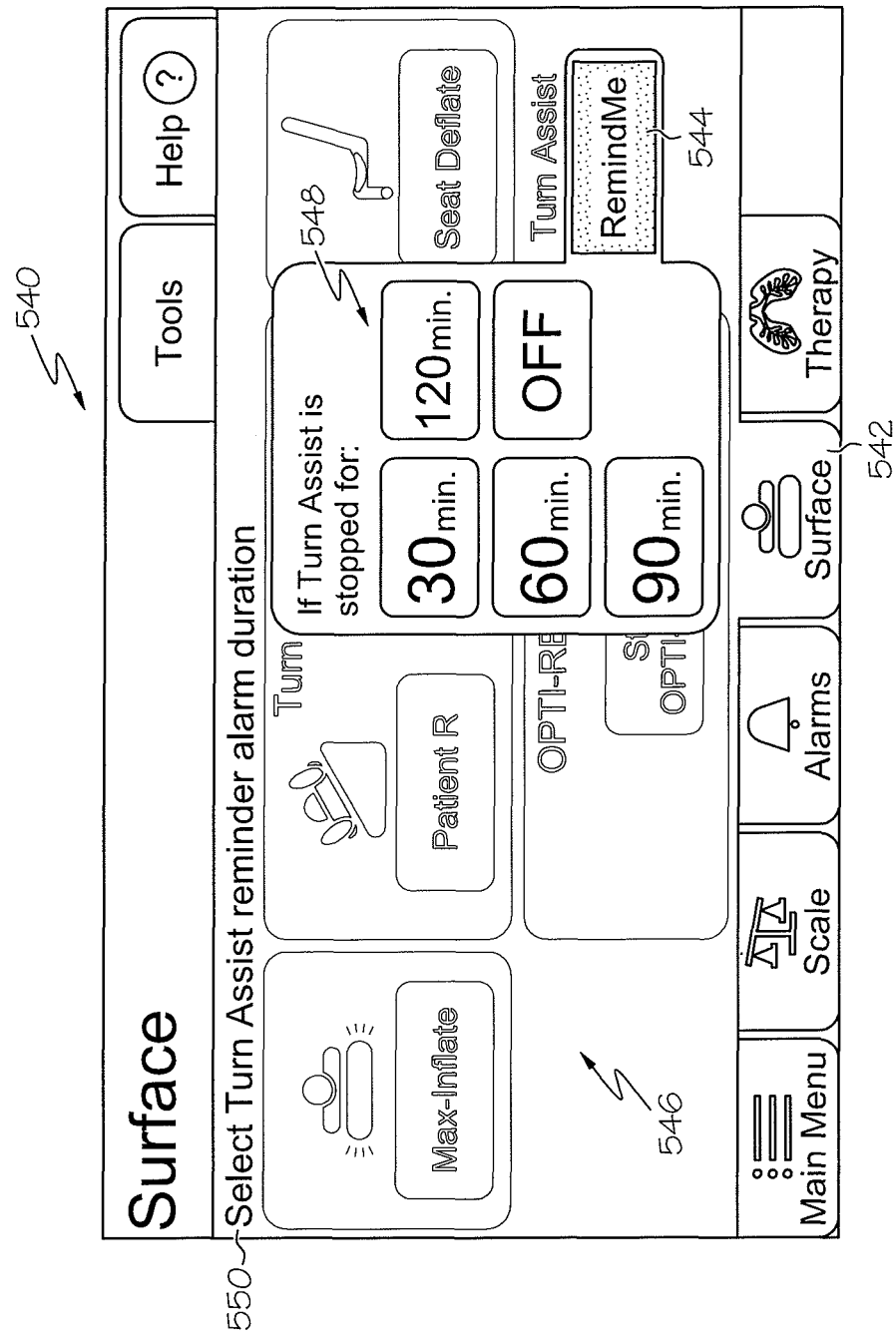
FIG. 13 is a screen shot of a user interface for activating a reminder feature of a patient support including text, graphical icons, user controls, reverse highlighting, selective coloration, and a "one-touch" pop-up input region.

FIG. 13 shows a screen 540 for configuring a reminder to the caregiver if the turning assistance operation has been stopped for a defined period of time. Such a reminder may be desirable to remind the caregiver that it is now time to activate turning assistance again. A brief textual instruction 550 relating to the active function 544 is provided and may change as the active function changes.

Screen 540 shows locked-out functions, i.e., functions that are not currently available to be configured, in reverse highlighting or "grayed out" mode 546. The remind me button 544 is activated and is shown filled in with a contrasting color in comparison to FIG. 11. A pop-up area 548 includes "one touch" selection buttons that allow the user to quickly select the period of time after which the reminder should be generated by only requiring a single action of the user: pressing or contacting one of the available buttons. Pressing in the grayed out area outside of region 548 does not result in any action or response by the patient support system. In addition, only one of the selection buttons in region 548 can be activated at a time. The screen 540 is thereby designed to reduce the risk of error due to confusion or unintentional or accidental button pressing by the user.

Similar screens are used to facilitate user configuration of other types of reminders. Reminders may be set in a like manner for rotation, percussion and vibration, turning assistance, and/or other therapies, features or functions of the patient support. A visual display of the time remaining until the next reminder may be presented, as shown by countdown area 672 of FIG. 16. If the reminder feature is in progress, and a user then starts a therapy, then the reminder countdown will automatically be stopped while the therapy is in progress, and the clock will reset and restart the countdown after the therapy is stopped or completed. When the reminder clock finishes its countdown and issues the reminder, the user may have the option to reset the reminder clock.

In the illustrated embodiment, a user can select a discrete amount of time to elapse after completion of a therapy after which a reminder will issue. For rotation therapy, the available reminder time choices may include 10, 20, 30 and 40 minutes. For percussion and vibration therapy, the reminder time choices may include 1, 2, 4, 5, and 6 minutes. For turn assist, the reminder time choices may include 30, 60, 90, and 120 minutes. After the desired reminder time is selected, the countdown clock 672 is displayed.

Figure 14:
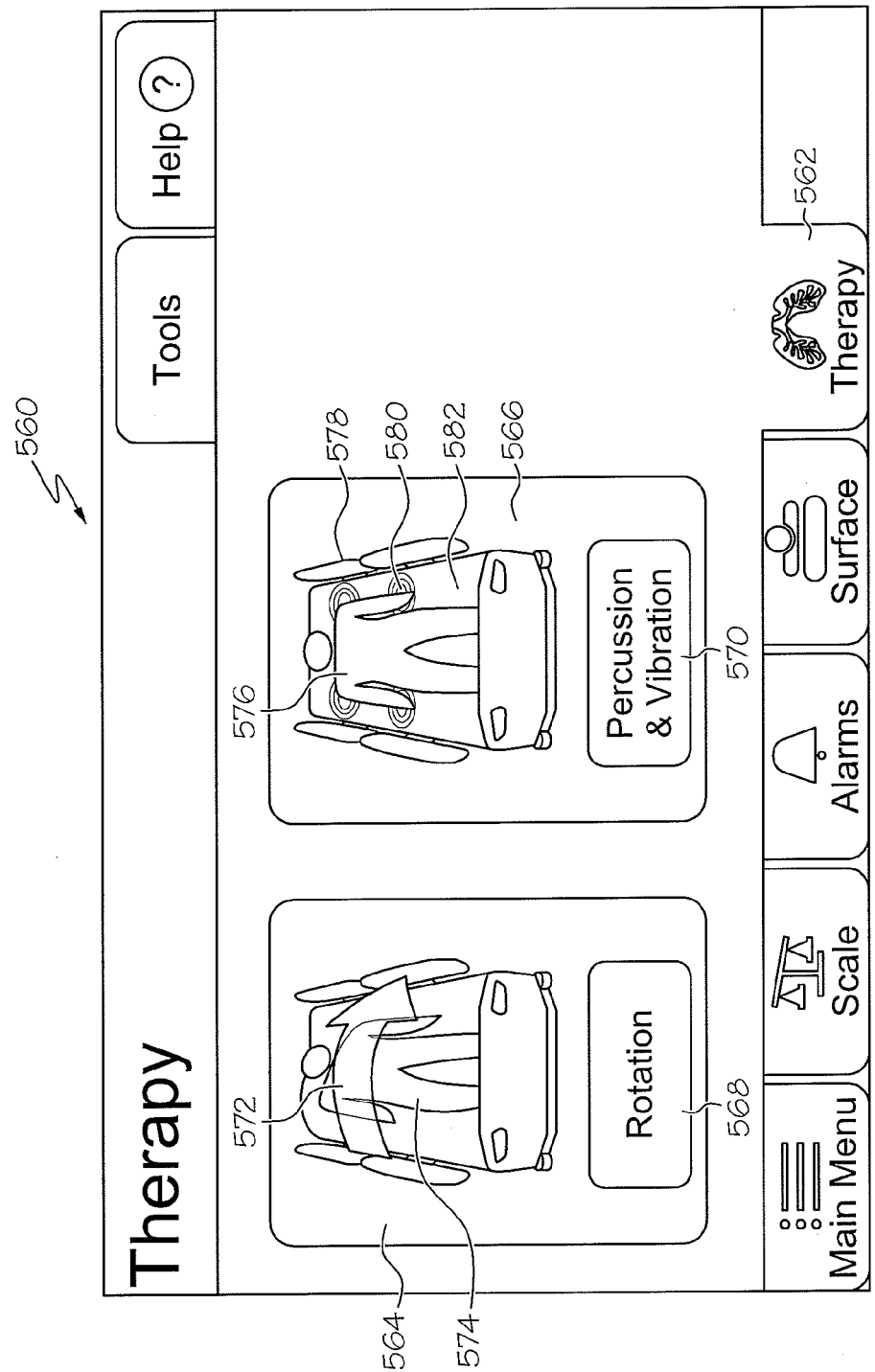
FIG. 14 is a screen shot of a user interface for therapy features of a patient support, including graphical elements, text, user controls, and highlighting for rotation and percussion and vibration features.
Figure 15:
FIG. 15 is a diagram illustrating steps in the operation of therapy features for rotation and percussion and vibration.

FIGS. 14 and 15 relate to operation of therapy functions of a patient support. FIG. 14 illustrates a user interface for selecting a therapy function and FIG. 15 is a diagram of steps performed in the operation of the functions. Main therapy screen 560 is similar to other main screens described above, in that the therapy function tab 562 is displayed in a contrasting color relative to the other function tabs to visually indicate that the therapy screen is active, and additionally, the "Therapy" title appears at the top of the screen. Screen 560 includes a first control region 564 and a second control region 566. Additional control regions may be added in area 584 or control regions 564, 566 may be replaced by other control regions, as new or upgraded therapies are loaded or added to the system, for example by upgrade module 78. Each of the control regions is set off from the others by selective highlighting, shading or coloration for ease of use.

Control region 564 includes textual and graphical elements to communicate to the user that the region is associated with rotation therapy. Textual elements include the button 568 titled "rotation". Graphical elements include an arrow 572 extending laterally across a graphical depiction of a patient 574 positioned on a patient support. The tail of arrow 572 is curved or arced to suggest movement in the direction of the arrow head. When the patient is rotated in the opposite direction, the direction of the curved arrow is reversed.

Control region 566 includes the function description "percussion and vibration" label on the user control 570 and graphical elements including a patient body 576 supinely positioned on a support surface 582, siderails 578 in the "up" position, and percussion and vibration elements 580 located on the surface 582 adjacent the shoulders and hands of the body 576. In general, elements 580 have the appearance of concentric circular ripples.

Figure 16:
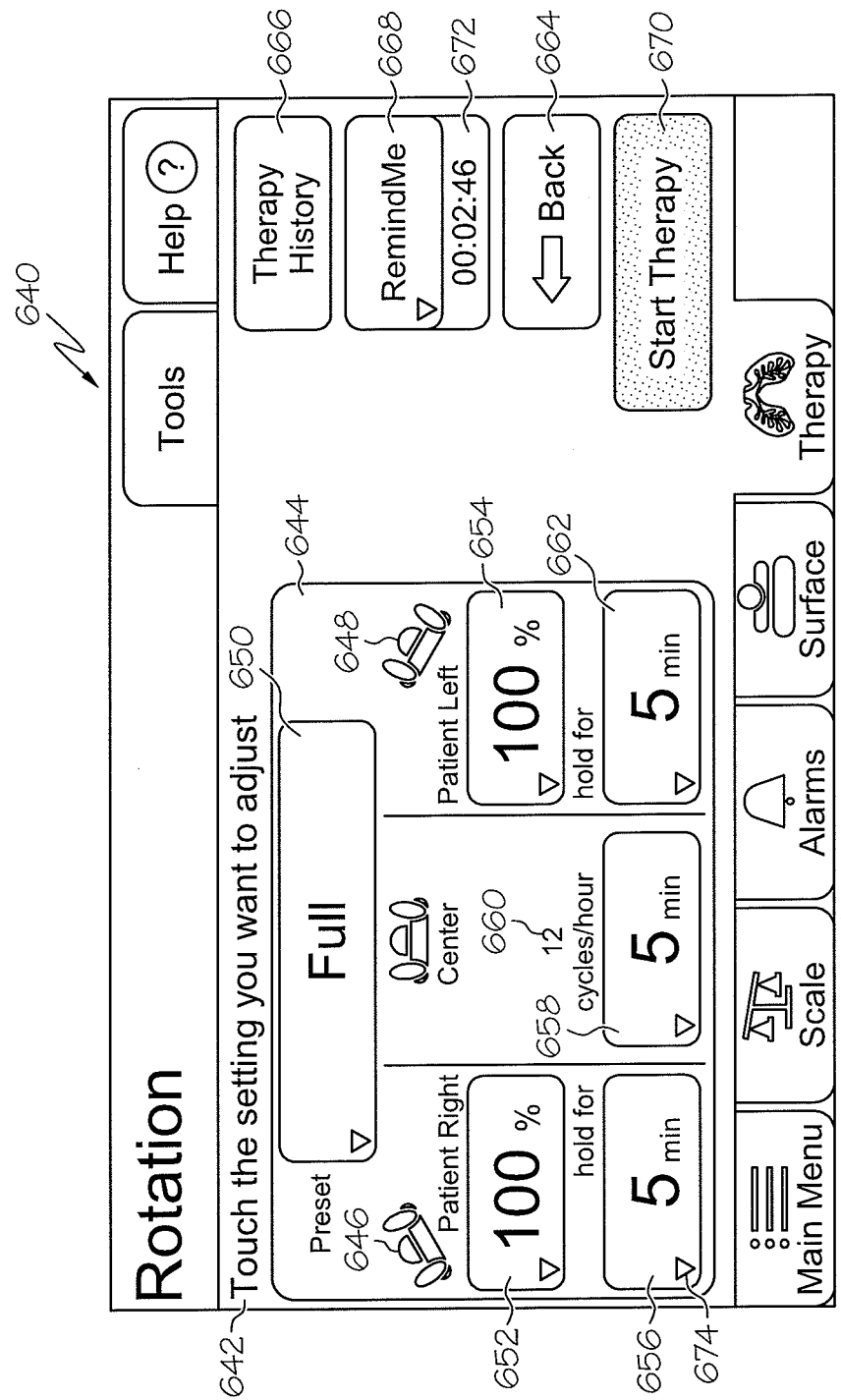
FIG. 16 is a screen shot of a user interface for a rotation feature of a patient support including text, instructions, data, graphical icons, user controls, selective highlighting and selective coloration.

Buttons 568, 570 are touchscreen controls in the illustrated embodiment. Button 568 is represented in FIG. 15 as rotation function block 592. When button 568 is activated, a main rotation screen 640, such as shown in FIG. 16, is displayed. Screen 640 provides options to the user including selecting or configuring rotation settings 596, configuring or activating a reminder 598, and viewing rotation history 600.

Referring to FIG. 16, the configurable rotation settings are set off from the rest of the display screen 640 by highlighting, shading or coloration of control region 644 relative to the rest of the display screen 640. Control region 644 includes a plurality of touchscreen controls 650, 652, 654, 656, 658, 662. These controls are designed as "one touch" controls as described above, such that after a control is selected for configuring, only one touch is required by the caregiver to select the appropriate value for the control.

Figure 17:
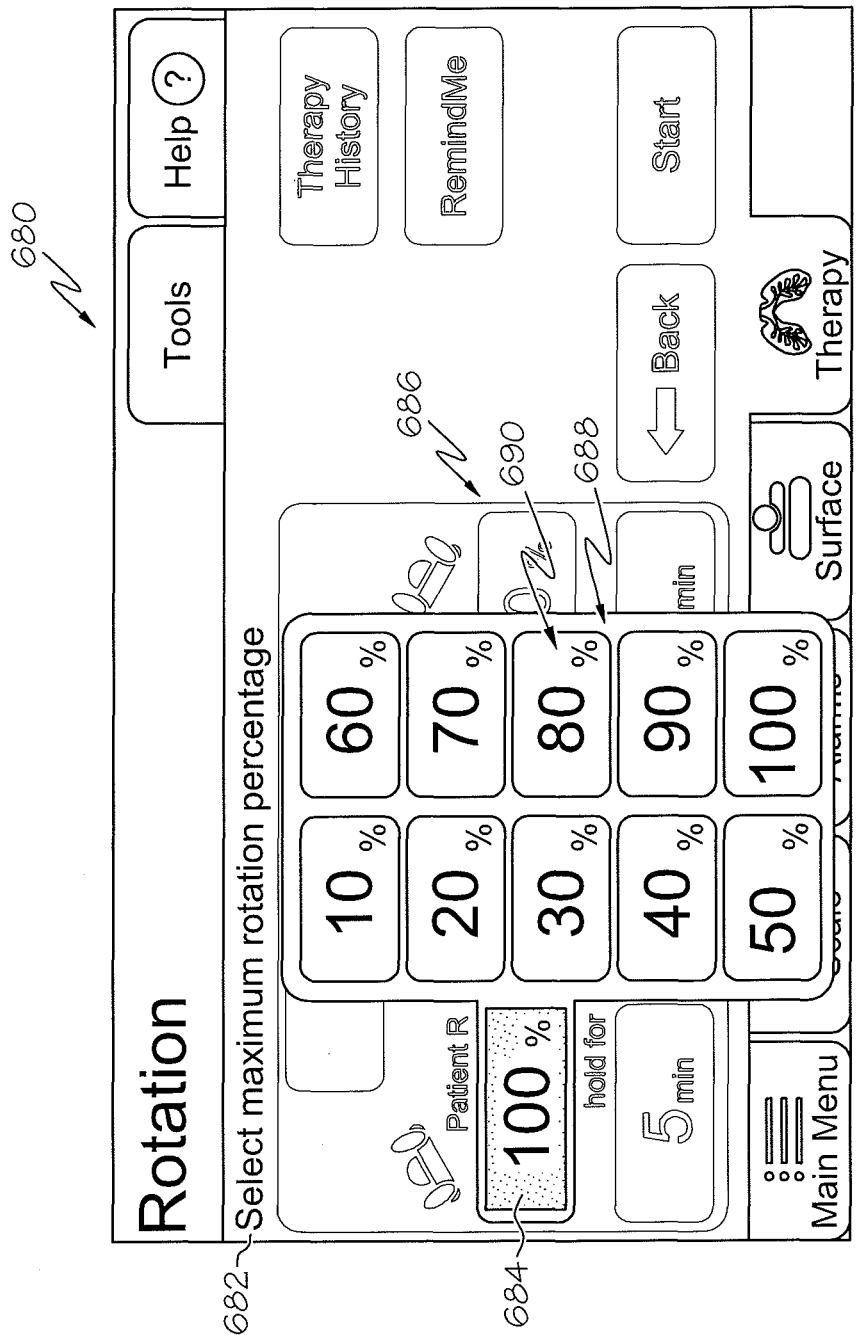
FIG. 17 is a screen shot of a user interface for configuring rotation settings including text, instructions, graphical elements, user controls, reverse highlighting, selective coloration, and a one touch pop-up input region.

This is illustrated in FIG. 17, wherein the "patient right" button 684 is indicated by selective coloration as being selected. Selection of button 684 results in pop-up area 688 being displayed. The user may select only one of the available buttons 690 at a time. Once a button 690 is selected, the pop-up disappears and the selected button value is displayed at button 684 (i.e., if the user selects "80%", the value "80%" would replace the "100%" previously displayed at button 684). These and other similarly configured buttons on the user module effectively act as both an input device and output device, because the new value selected by the user is subsequently displayed on the selection button itself. This type of "one touch" rotation selection allows for faster adjustments by a caregiver than prior art systems in which a caregiver must press and hold a button (pr press the button multiple times) while the rotation amount scrolls numerically up or down, or in which a dial is turned or lever moved or a graphical icon is moved via touching and dragging from the prior setting to the new setting.

In FIG. 16, a user may select a preset condition via touchscreen control 650. The preset conditions include predefined rotation settings, for example: "minimum" at 8 cycles per hour (cyc/hr), 50% turn; "moderate" at 10 cyc/hr, 70% turn; or "full" at 12 cyc/hr, 100% turn. Alternatively, the user may select "custom" via control 650, in which case buttons 652, 654, 656, 658, 662 become enabled, thereby allowing the user to more specifically configure the rotation settings. Turn percentage buttons 652, 654 enable the user to select an amount of turn to the right or left. Right pause 656, center pause 658, and left pause 662 enable the user to select an mount of time to pause or hold the patient in the right side-lying, centered, and left side-lying positions before proceeding to the next position. A graphical indicator, such as triangle 674, positioned on a control button, may be used to indicate that the element is configurable. For example, pressing a button that has an indicator 674 results in a pop-up display of selectable choices. If a "preset" configuration is selected, the "custom" controls are disabled or grayed out.

While a rotation setting is being configured, other functions available on screen 680 are disabled. This is indicated to the user by reverse highlighting or "gray" shading as shown at region 686 of screen 680.

Region 644 of FIG. 16 also includes graphic elements 646, 648, which are displayed from the patient's reference point. For example, element 646 appears tilted toward the left side of the user interface from the perspective of a person viewing the screen 640, but corresponds to how a patient rotated to the patient's right side would appear from the perspective of a caregiver located at the foot end of the bed. Element 648 is similarly configured to represent rotation to the patient's left side.

Region 644 also includes a numerical value 660, which represents the number of cycles per hour that correspond to the number of minutes of rotation selected by the caregiver at button 658. When the user selects a new setting at button 658, the numerical value 660 is automatically calculated and updated.

Figure 19:
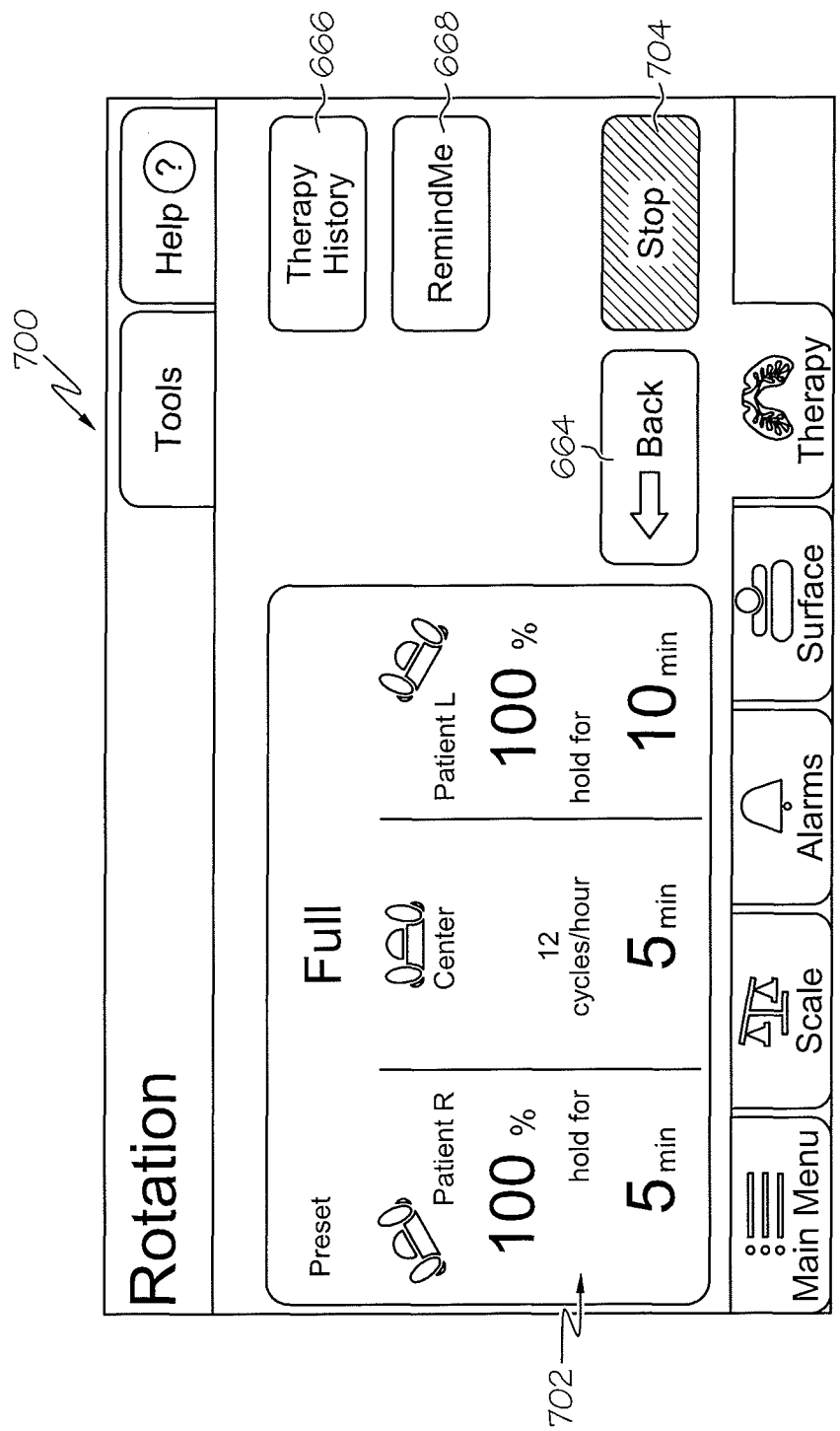
FIG. 19 is a screen shot of a user interface for displaying information relating to a rotation feature while the rotation feature is in operation, including text, numerical data, graphical icons, user controls and selective coloration.

Screen 640 also includes a textual instruction 642 that is updated as the user selects different functions on the screen, a back button 664 to return the user to the previously selected function, a therapy history button 666 corresponding to function block 600 to enable the user to view a history of rotation therapy applied to the patient, and a reminder button 668 corresponding to function block 598 of FIG. 15. Also included on screen 640 is a "start" button 670, which, when activated, starts the operation of the rotation therapy according to the user selected parameters. Prior to activation, button 670 is filled in with a first suggestive color (e.g., green for "go"). When the rotation therapy is in progress, button 670 converts to a "stop" button filled in with a second suggestive color (e.g., red for "stop"), as shown in FIG. 19.

Referring to FIG. 15, once the user configures the rotation settings at block 596, the system automatically checks whether the siderails are up or down (e.g., via siderail module 74) at block 602. If any of the siderails are down, the user will be prompted via an appropriate message on the display screen to raise them before rotation therapy can start. The system also automatically checks whether the seat deflate feature is active, at function block 603. If seat deflate is active, the user will be prompted to deactivate the seat deflate feature before rotation therapy can start.

Figure 18:
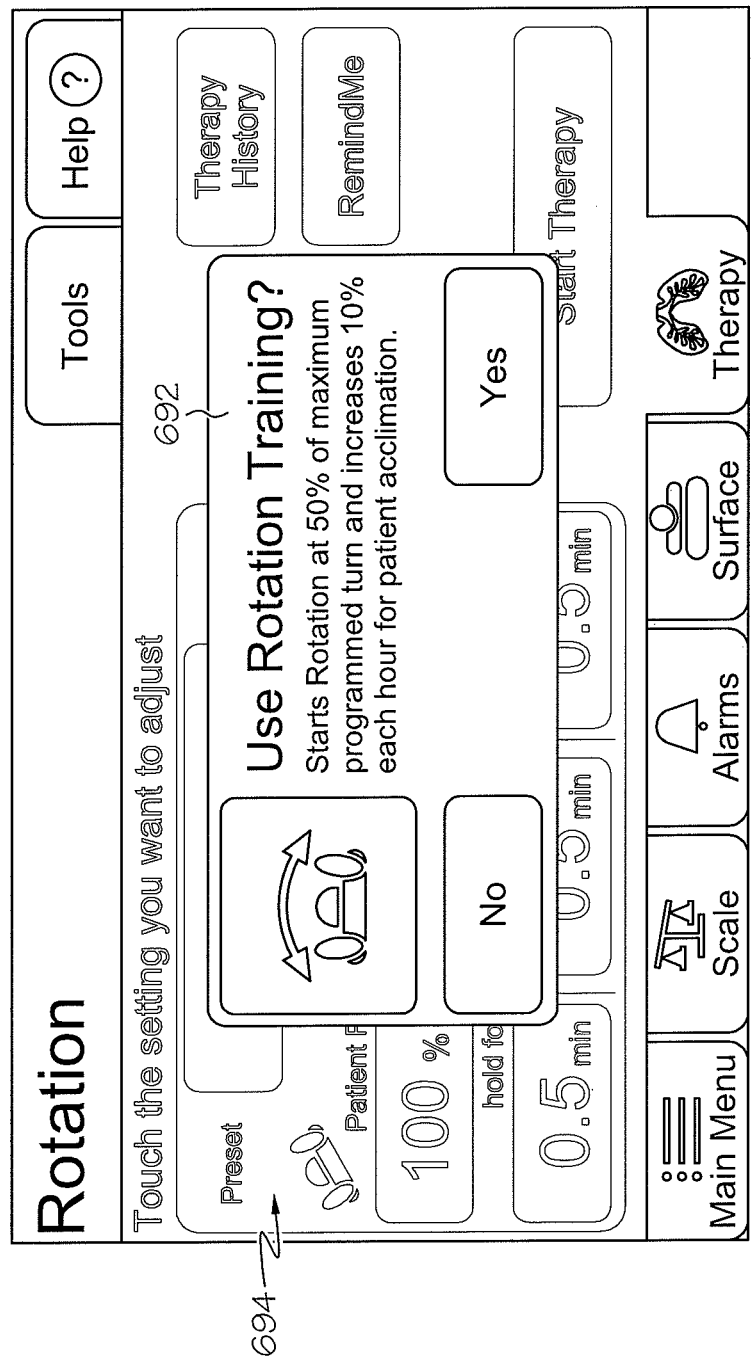
FIG. 18 is a screen shot of a user interface for selecting a rotation training feature of a patient support, including text, instructions, graphical elements, user controls, reverse highlighting, selective coloration, and a pop-up region.

The user may then be prompted to decide whether to use rotation training as shown in FIG. 18. Rotation "training" may be used to gradually introduce the patient to the rotation therapy. In the illustrated embodiment, rotation will begin at half the maximum turn degree and gradually increase over time to acclimate the patient.

In general, rotation therapy may be at least temporarily suspended or paused when any siderail is lowered, when head of bed angle is raised higher than about 40 degrees, when foot of bead angle is lowered more than about 30 degrees, when the patient support is in or moving into or attempted to be moved into the chair position, if percussion and vibration, max-inflate, or turning assistance is activated, or if CPR is activated, or for other reasons.

When the rotation parameters are set, rotation therapy is started as indicated at block 604. The user display is updated as shown in FIG. 19 once the rotation therapy is in progress. Rotation status display screen 700 displays the current rotation settings in region 702, which is set off from the rest of screen 700 by highlighting, shading or coloration, and button 704 is modified to enable the user to stop the therapy as described above.

Figure 20:
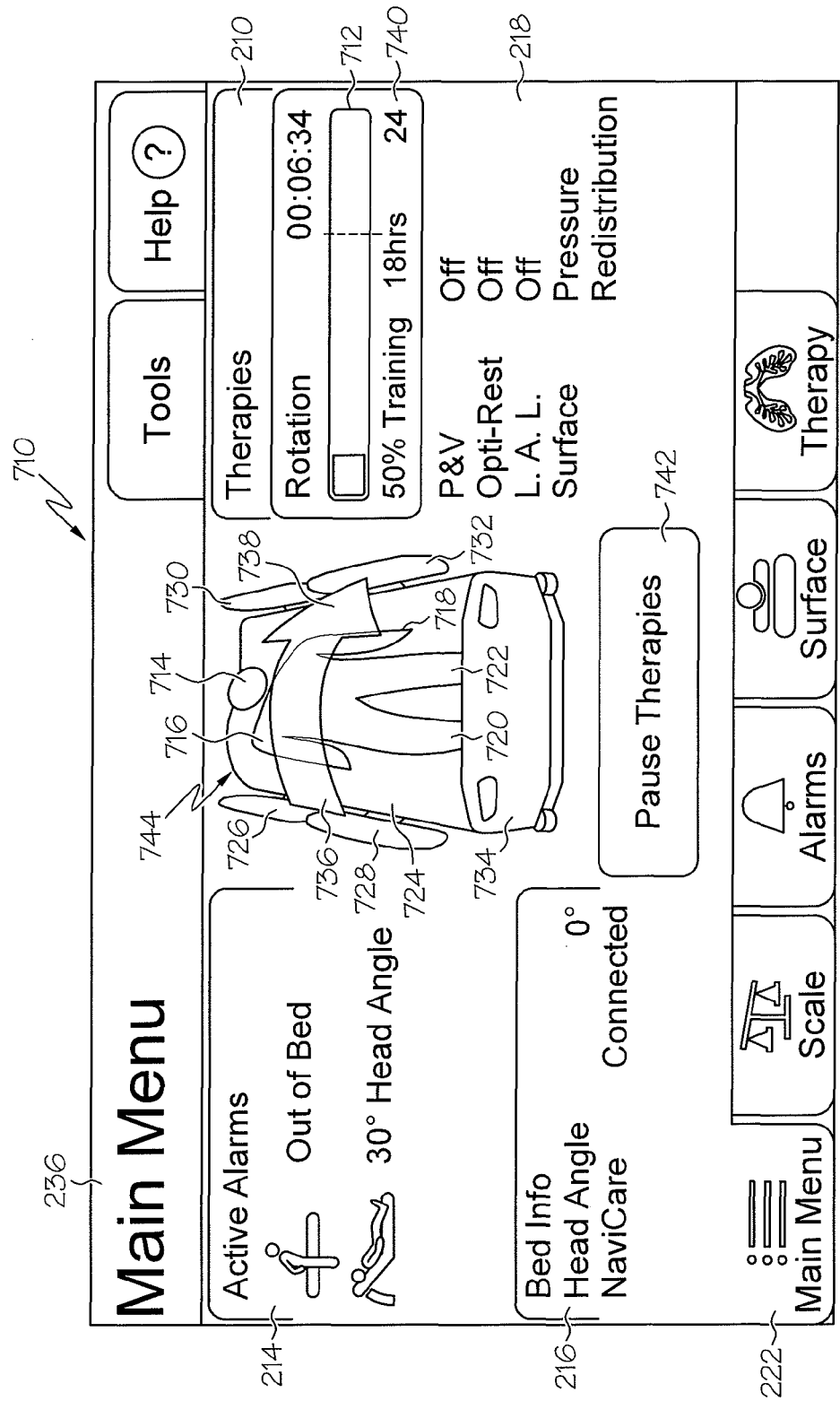
FIG. 20 is a screen shot of a user interface for a main menu displayed while a therapy is in operation, including text, static graphical elements, animated graphical elements, data, user controls, selective highlighting, and selective coloration, where current data relating to alarms, bed status, bed connectivity, therapy status is all displayed on a single screen.

FIG. 20 illustrates a main menu screen as updated at block 606, while rotation therapy is in operation. Screen 710 is similar to the main menu screens previously described, except that portions of the patient and bed graphic 744 are animated to simulate rotational movement of the support surface and patient that occurs when rotation therapy is in operation. Also, a thermometer-style status bar 712 indicates the amount of progress completed for the rotation therapy. Status bar 712 is set off from other parts of the screen 710 by selective coloration, highlighting or shading 740. In addition, a "pause" button 742 is provided to allow the user to at least temporarily suspend the therapy in progress. The button is generally made conspicuous (e.g., larger size, centrally located) for easy access by the caregiver.

Graphic 744 includes animated graphical elements that dynamically change the display to simulate rotation of the surface and patient when rotation therapy is activated. In particular, the surface 724 is shown as rising on one side of the patient thereby "elevating" the corresponding shoulder 716 and leg 720 of the patient, in the graphical depiction. The graphical depiction of the surface and patient continue to dynamically change in an animated fashion as a side of the support surface and patient graphical elements rises and rotates. For instance, the patient's head 714, arm 718 and leg 722 become animated to indicate rotation in the reverse direction.

Arrow graphical element 736 is also animated to indicate motion in the direction of the arrow head 738. Coloring or shading of the arrow body is configured to convey a sense of motion in the direction of the arrow head 738 as well. For instance, the arrow tail is filled with a lighter shade and the arrow is gradually darkened toward the arrow head 738. These animated features communicate patient support therapy information to caregivers in a manner that is easy to view, simple to understand, and not hindered by any language barriers or translation issues.

Figure 21:
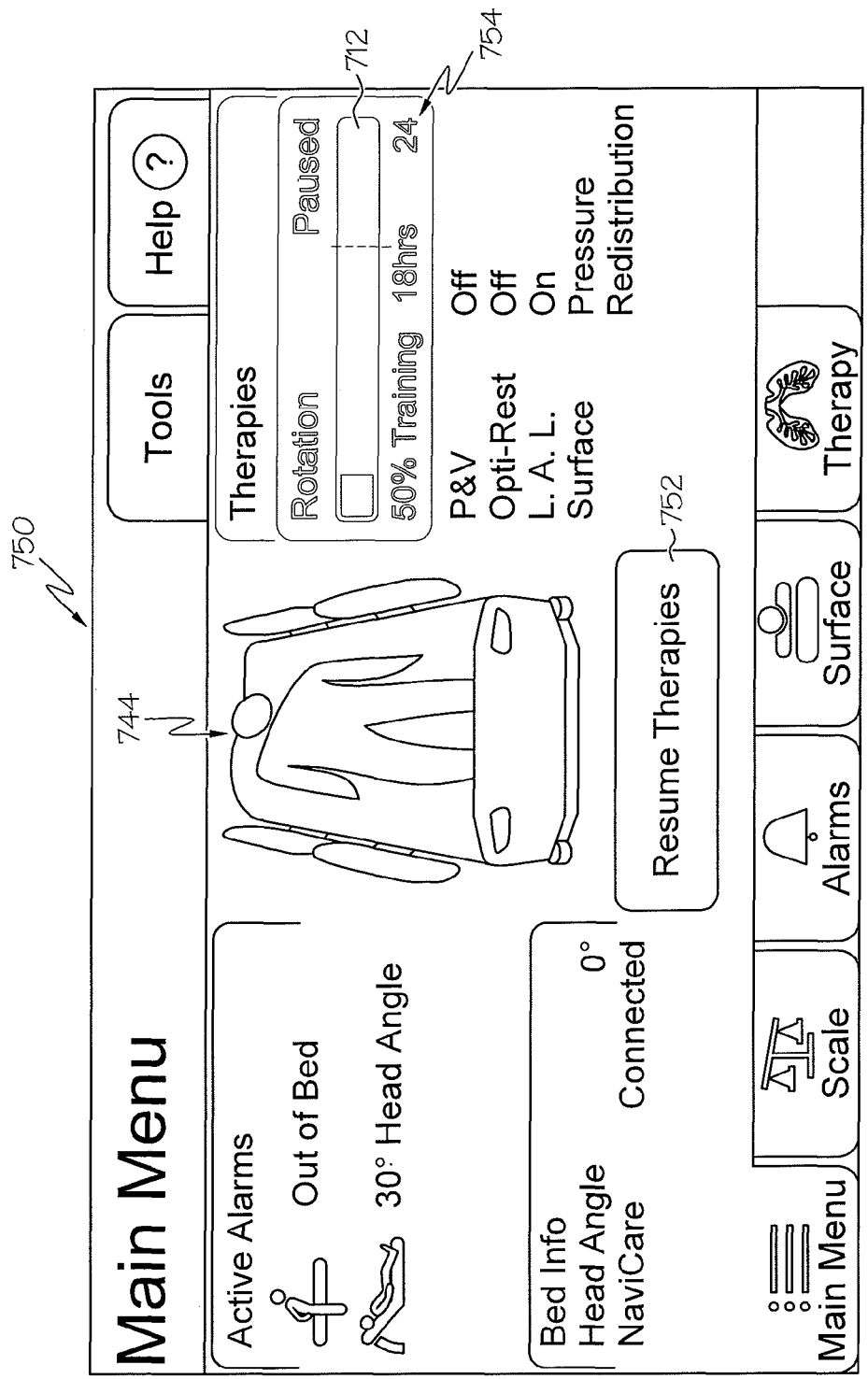
FIG. 21 is a screen shot of a user interface for a main menu displayed while a therapy is paused, including text, static graphical elements, animated graphical elements, data, user controls, selective highlighting, reverse highlighting, and selective coloration, where current data relating to alarms, bed status, bed connectivity, therapy status is all displayed on a single screen.

While in rotation therapy, the user may pause the therapy by pressing button 742. In general, when a therapy is paused, another bed function may be activated, such as another therapy, the weigh scale, or other function or feature of the bed or mattress. If pause button 742 is activated, the animation of graphical element 744 also pauses and "moving arrow" 736, 738 is not displayed during the pause, as shown in FIG. 21. Also shown in screen 750 is that the status thermometer 712 is shown in reverse highlighting or "grayed out" mode 754 when the therapy is paused. A textual indicator that the therapy is "paused" is also provided. In addition, button 752 is converted from a "pause" button to a "resume" button.

Alternatively or in addition to the animated graphics, the user interface may display a visual message such as "In Progress" to indicate that a therapy is in progress.

In general, the system will also automatically temporarily pause an in-progress rotation therapy if the user activates a percussion and vibration therapy while rotation therapy is running, and then will resume the rotation therapy so that both rotation and percussion and vibration therapies can be in operation at the same time. If a percussion and vibration therapy is in progress, however, a new rotation therapy may be started without pausing the percussion and vibration therapy. In general, multiple therapies, such as rotation, percussion and vibration, and surface therapies, may be requested. When multiple therapies are in operation at the same time, each therapy type may be paused or stopped without affecting the other ongoing therapies.

Figure 22:
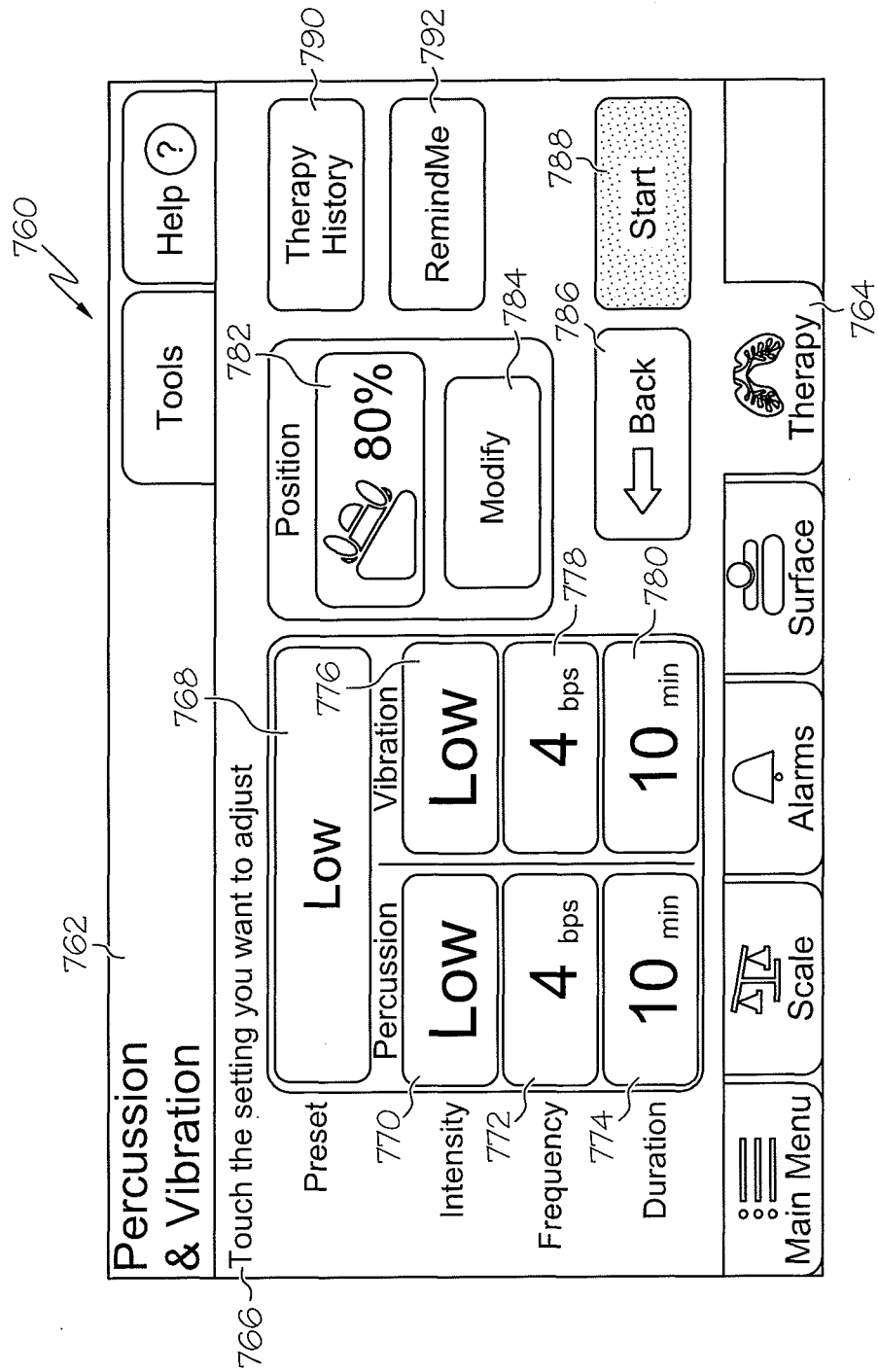
FIG. 22 is a screen shot of a user interface for configuring settings for a percussion and vibration feature of a patient support, including text, instructions, numerical data, user controls, graphical elements, selective highlighting, and selective coloration.
Figure 23:
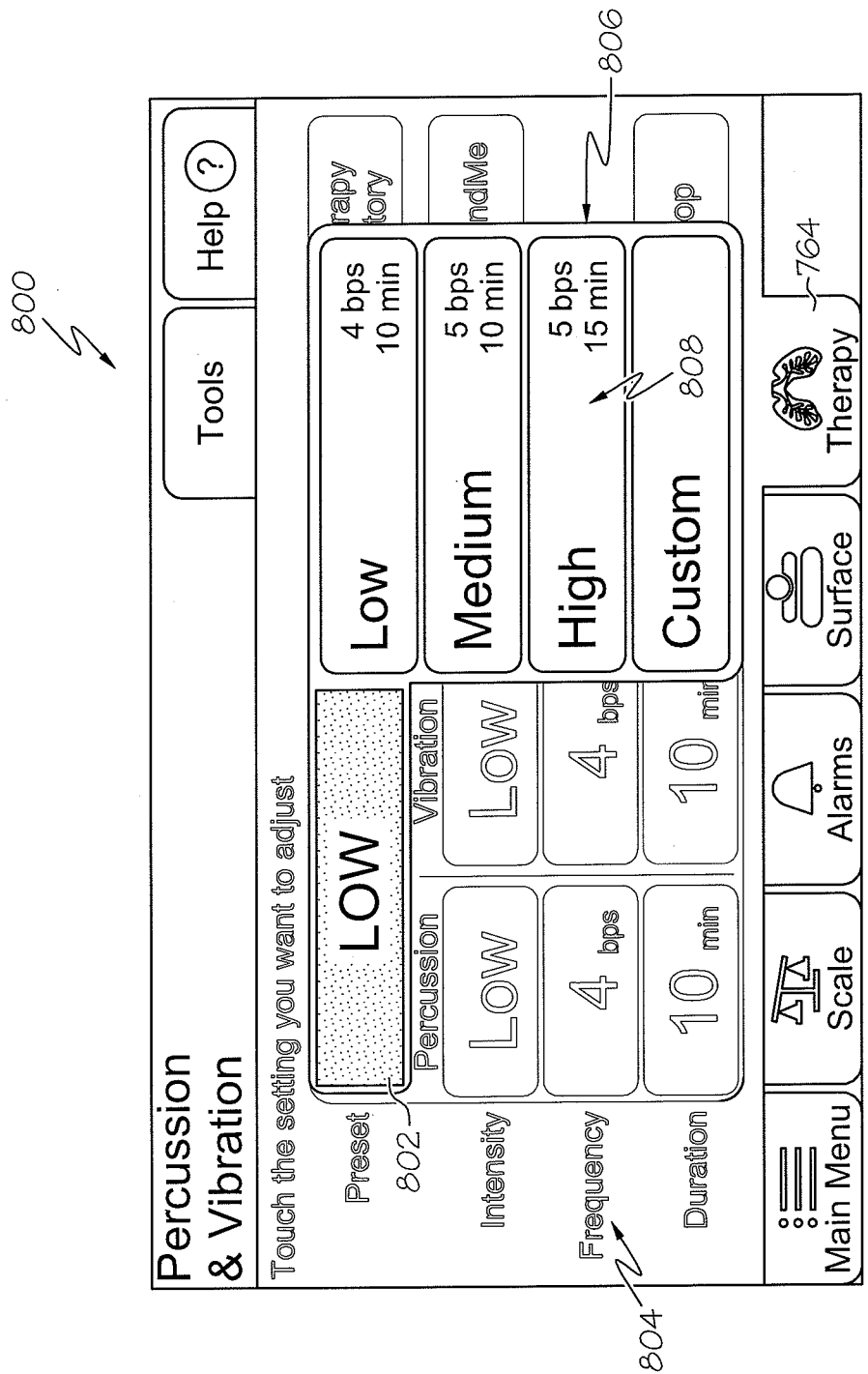
FIG. 23 is another screen shot of a user interface for configuring settings for a percussion and vibration feature, including text, instructions, graphical elements, user controls, reverse highlighting, selective coloration, and a one touch pop-up input region.
Figure 24:
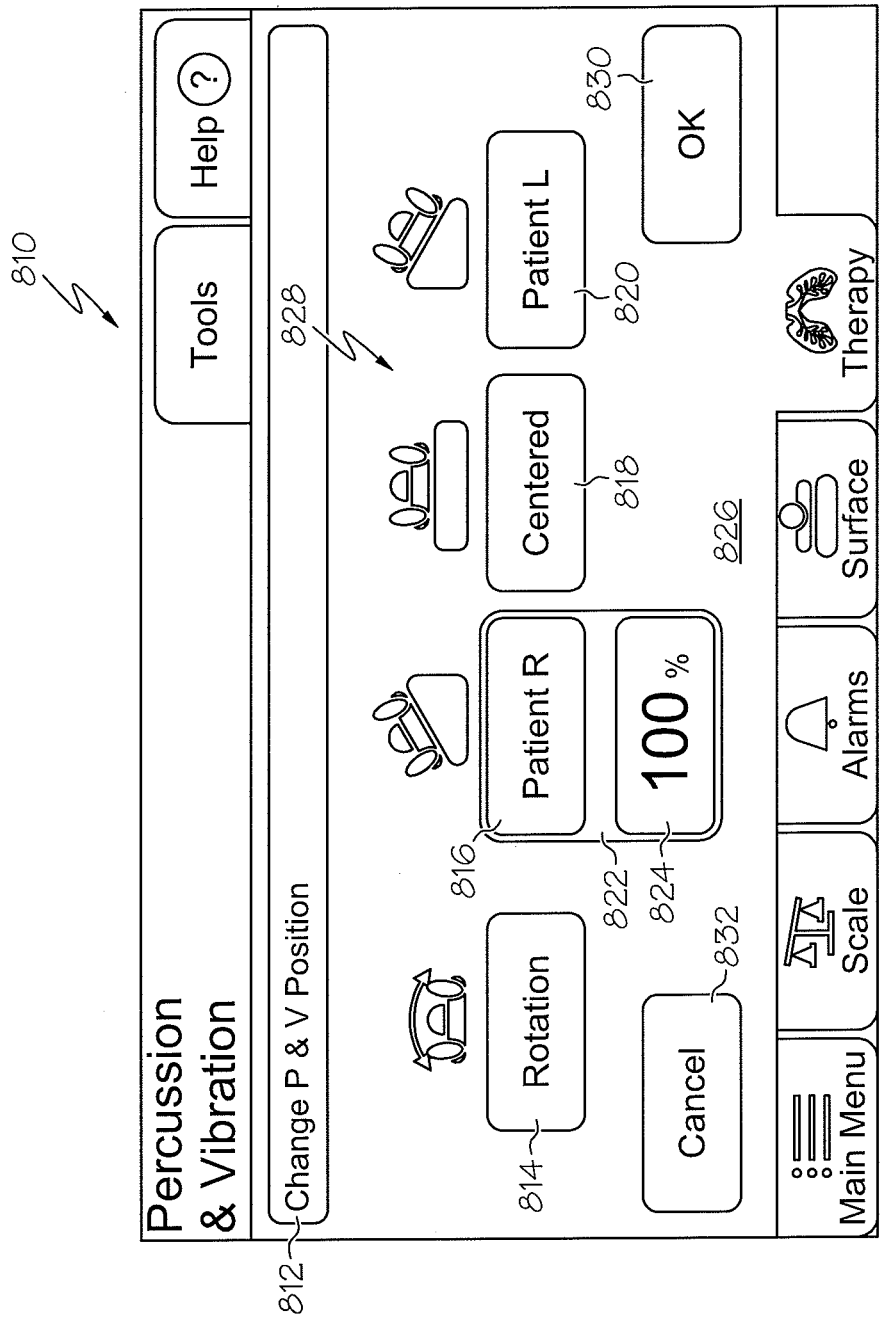
FIG. 24 is another screen shot of a user interface for configuring settings for a percussion and vibration feature including text, graphical elements, user controls, and selective highlighting.
Figure 25:
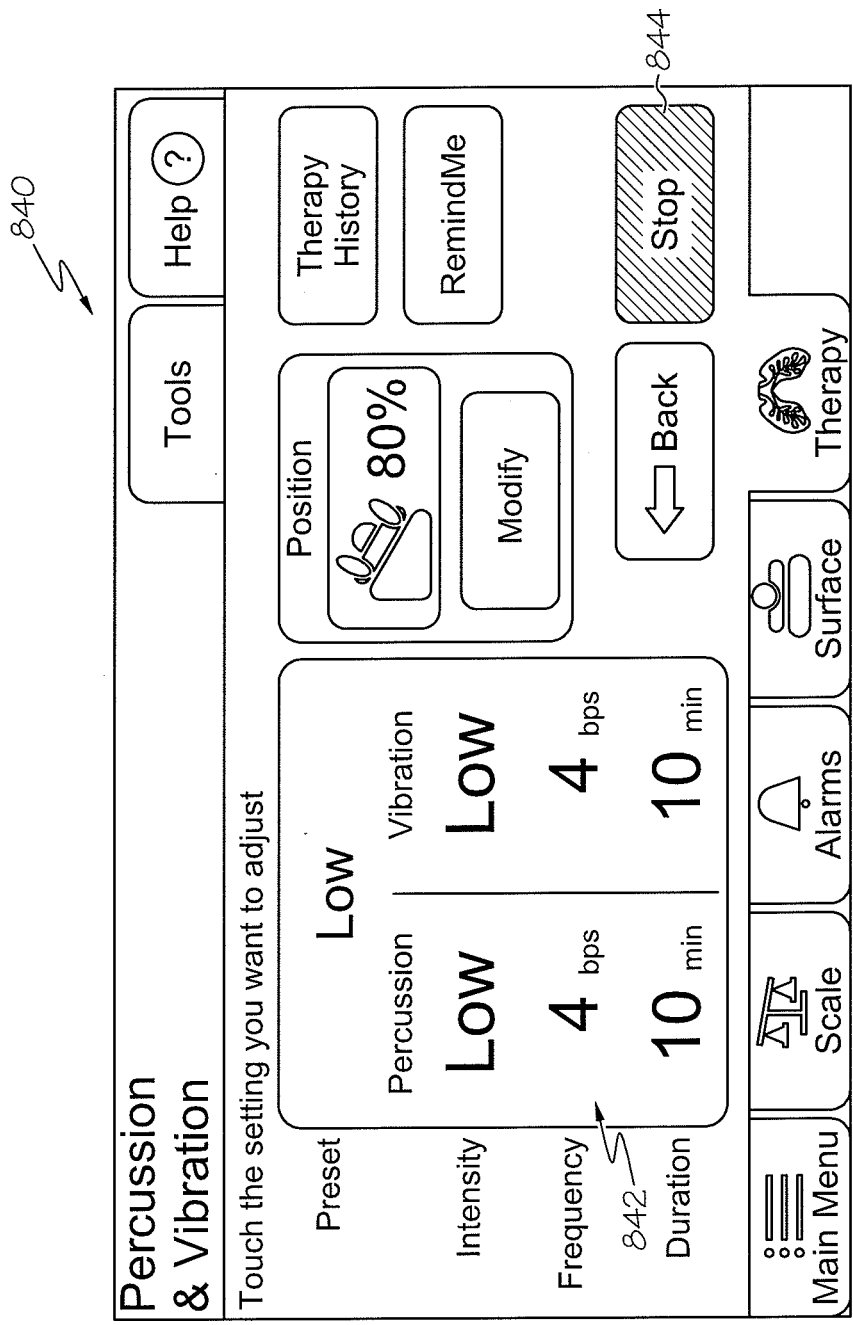
FIG. 25 is a screen shot of a user interface for displaying information relating to a percussion and vibration feature while the rotation feature is in operation, including text, numerical data, graphical icons, user controls and selective coloration.

FIGS. 22-26 relate to an automated percussion and vibration therapy of a patient support, and FIG. 15 illustrates steps performed in configuring a percussion and vibration therapy. Screen 760 of FIG. 22 is displayed when a percussion and vibration therapy is not already in progress. The user may configure the settings for percussion and vibration therapy via controls 768, 770, 772, 774, 776, 778, 789, 784, 786, 788, 792. These controls are "one touch" controls as shown in FIGS. 23 and 24 and described above with reference to the rotation therapy configuration screens.

As shown in FIG. 22, an option is presented to the user to select a predetermined percussion and vibration therapy setting using touchscreen control 768. Activating control 768 enables the user to select from a plurality of discrete preset choices, such as "low" at 4 bps (beats per second) and duration of 10 minutes; "medium" at 5 bps and 10 minutes duration; "high" at 5 bps and 15 minutes duration. To use the customized settings, "custom" is selected at control 768, in which case touchscreen controls 770, 776, 772, 778, 774, 780 become enabled. If "preset" configuration is selected, the "custom" controls are disabled or grayed out.

Intensity may be customized for percussion and vibration by using controls 770, 776. Discrete choices for each control 770, 776, such as "low", "medium", and "high" are displayed and one of the choices may be selected by the user for each control 770, 776. For percussion frequency button 772, the discrete choices include 1 to 5 beats per second, for example. For vibration frequency button 778, the discrete choices include 5 to 25 beats per second, in 5 bps increments, for example. For duration buttons 774, 780, the choices include a range of values between and including 1 to 30 minutes, for example. In one embodiment, a minimum duration of about 3 minutes is required for therapy history statistics to be captured.

Patient position for percussion and vibration therapy is selectable by activating modify control 784. Discrete choices for position control 782 include patient's right side 816, patient's left side 820, centered 818, or rotation 814, as shown in FIG. 24. If right side 816 or left side 820 is selected, then the amount of turning (i.e. percentage) is selected for automated turning assistance to that side. If rotation is selected, then the rotation settings are configured as described above with reference to FIG. 16. If the user selects OK at control 830, then the position selected is displayed at control 782 of FIG. 22.

The user may initiate operation of the therapy via control 788. Prior to starting the percussion and vibration therapy, the patient support system checks the siderails at function block 620 and checks the head of bed angle at function block 622. If one or more of the siderails is down or the head of bed angle is above an acceptable range (e.g. above 40 degrees), the system prompts the user via an appropriate message on the display screen to make the appropriate adjustments to the patient support before the therapy can be started.

Figure 26:
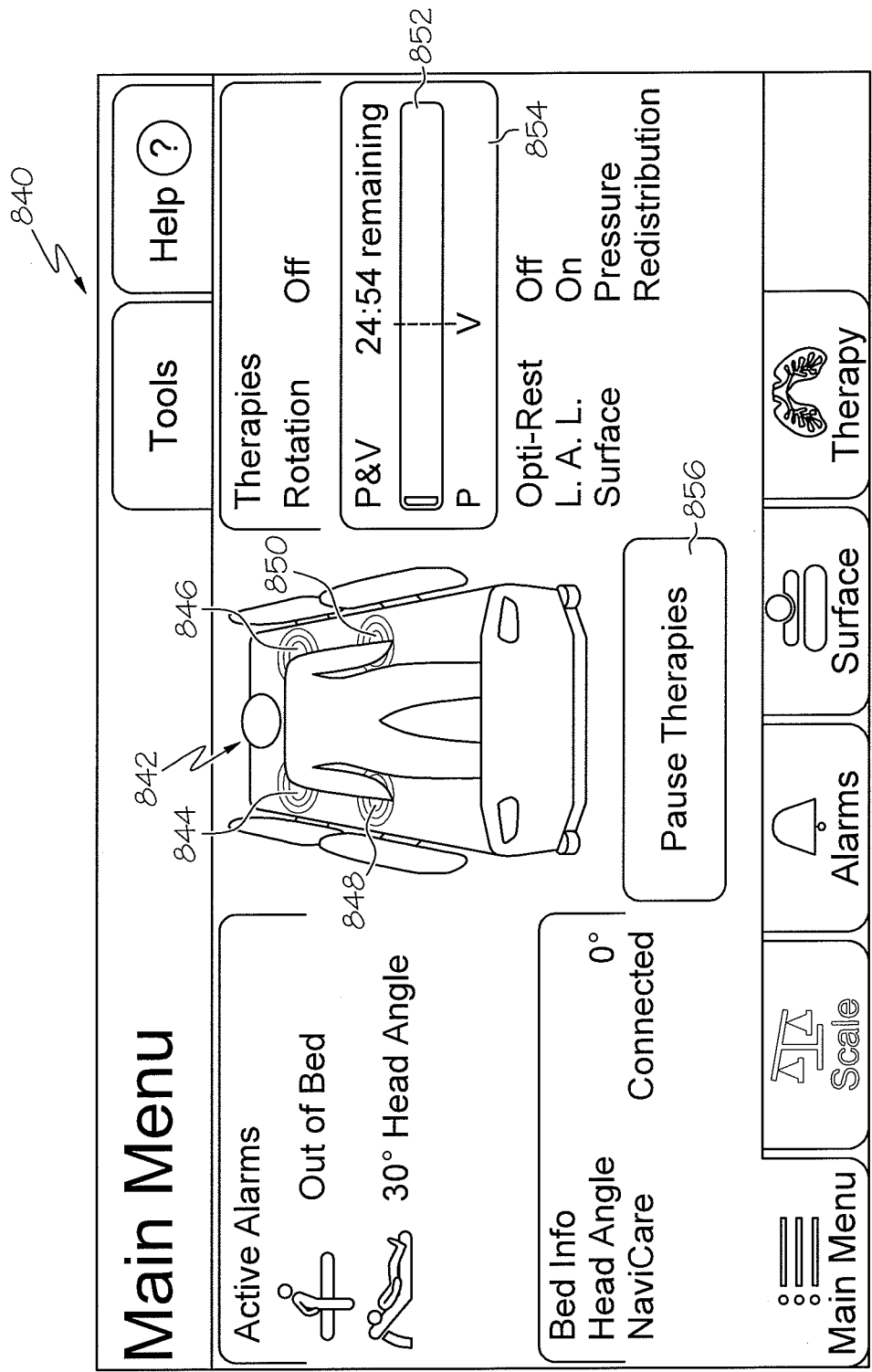
FIG. 26 is a screen shot of a user interface for a main menu displayed while a therapy is running, including text, static graphical elements, animated graphical elements, data, user controls, selective highlighting, and selective coloration, where current data relating to alarms, bed status, bed connectivity, and therapy status is all displayed on a single screen.

When the percussion and vibration therapy is started, the user interface display is updated at function block 626 to activate the animated features of the graphical user interface, as shown in FIG. 26. When percussion and vibration therapy is running, the portions of graphical element 842 of screen 840 become animated to simulate the percussion and vibration motion experienced by the patient positioned on the patient support. This is accomplished by providing animated elements 844, 846, 848, 850. These elements are "active" concentric circular ripples that appear as though they are vibrating through the use of animation. A thermometer-like status bar 852 is also provided in a highlighted region 854 to communicate the status of the therapy to the user. A pause button 856 is also provided and operates in like fashion to similar buttons described above.

If both rotation therapy and percussion and vibration therapy are in operation at the same time, then the rotation therapy animations (i.e., "turning" patient and "moving" arrow) and the percussion and vibration animations (i.e., "vibrating" ripples) are active.

Figure 27:
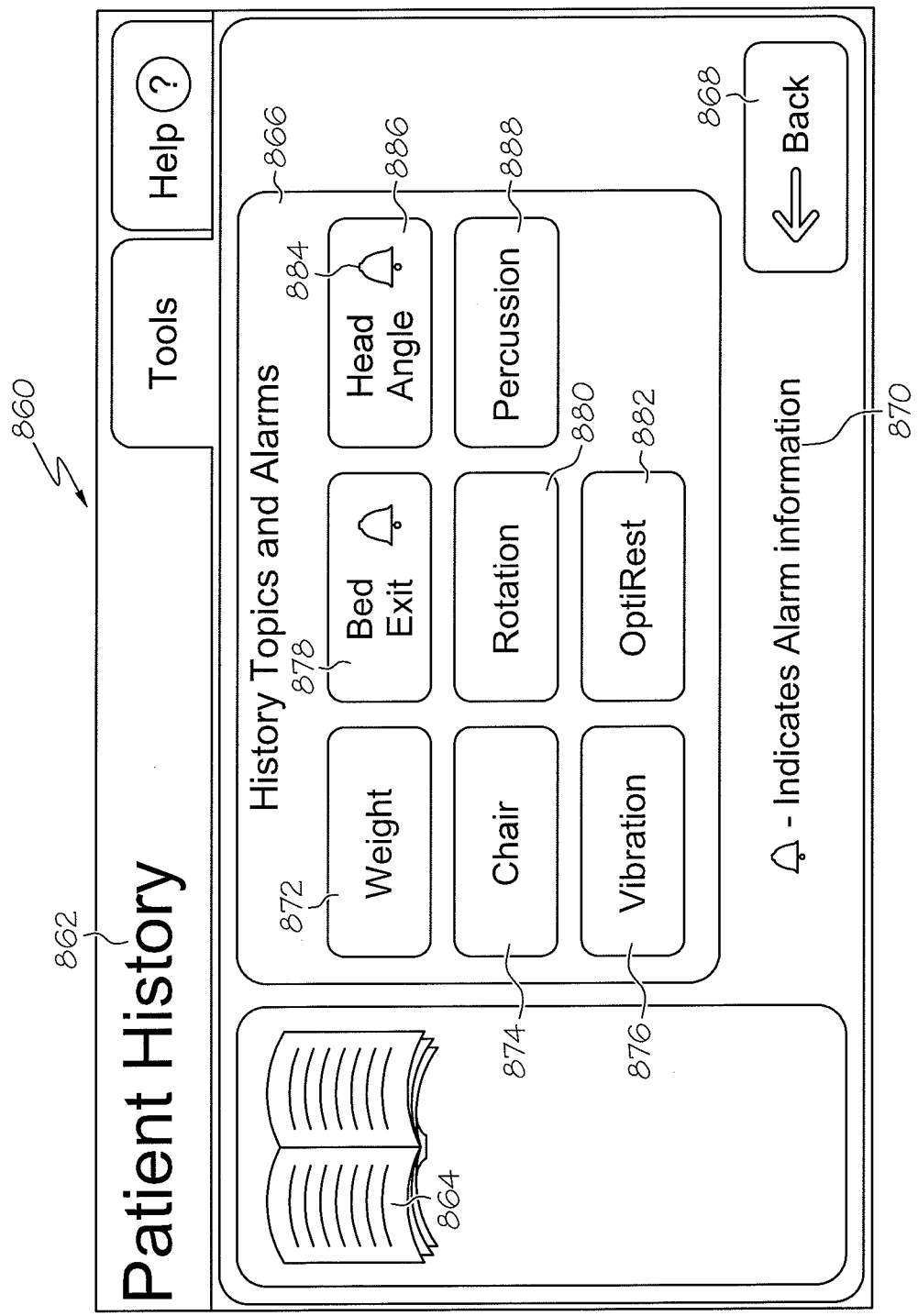
FIG. 27 is a screen shot of a user interface for patient history features of a patient support, including graphical elements, text, user controls and selective highlighting.

FIG. 27 illustrates a patient history reports screen 860, which gives the user access to historical data about the patient, the patient support, and features, functions, and therapies provided by the patient support. Available historical data includes data relating to the patient's weight 872, the length of time the patient support is in the chair position 874, the history of vibration therapy performed 876, the history of active bed exit alarms 878, the history of rotation therapy performed 880, the history of "opti-rest" or pressure redistribution or other surface therapies performed 882, the history of active head of bed angle alarms 886, and the history of percussion and vibration therapy performed 888. A graphical icon 884 sets off the alarm history features from the other available options for easy identification by the user as indicated by legend 870. A graphical element 864 is used in conjunction with the textual screen title 862 to orient the user with the screen.

FIGS. 28-30 illustrate historical data graphs for bed exit alarm history and head of bed angle history as described above. Selective coloration is used to indicate to the user the time periods of active alarms, as shown. For example, in FIG. 28, the relatively darker areas of the graph 904, 908 indicate time periods in which the bed exit alarm is enabled or set, while the relative lighter shaded areas 892 indicate time periods in which the bed exit alarm is turned off. In FIG. 29, the darker shaded areas 936 indicate time periods when the head of bed angle alarm is enabled or set. In other embodiments, such historical information may be provided in a tabular form or another graphical form, or other suitable format as may be considered desirable by the user.

In general, the user may customize the "x" and "y" axes of the graphs of FIGS. 28-30. For example, the "y" axis 894, 924 indicates the time period during the day and may be extended up to 24 hours or shortened to a shorter period within the day. The "x" axis 896, 926 shows the days in the date range monitored. The "duration" 898, 928 is an automatically calculated value representing the amount of time the particular alarm was enabled or set for each day shown in the graph. For example, referring to FIG. 28, on Oct. 11, 2006 the bed exit alarm was set for a total of 12 hours and 19 minutes on that day. The duration feature enables a caregiver to quickly spot days that may have been out of the ordinary in terms of the duration of alarms set. The caregiver can then go directly to the bed exit alarm configuration screen (e.g. FIG. 9) to reconfigure the alarm settings, via control 900.

In the head angle history graph of FIGS. 29 and 30, touchscreen control 930 enables the user to change the current view, while control 932 displays the current view (e.g., times and durations of monitoring the head of bed angle and the head of bed angle was above 30 degrees). Pressing the modify view button 930 presents discrete choices 956, such as above 30 degrees, above 45 degrees, and the like, at control 954. Control 954 also provides the user with an option to view the alarm history, i.e., the history of occurrences of the head of bed angle actually having been triggered or activated by the head of bed angle going below the preset alarm condition. An alarm history graphical report representing the history of activated alarms may then be viewed.

FIG. 31 illustrates an embodiment of a patient support 970 including multiple user modules 1016, 1018 and multiple user module mounting regions 1002, 1004, 1006, 1008, 1012. Patient support 970 has a head end 972 and a foot end 974, a base 976, frame 978 supported above the base 976 by a lift mechanism 982, a deck 980, wheels or casters 984, 986, a mattress 988, a head of bed angle sensor 990 coupled to mattress 988, and perimeter barriers 992, 994, 996, 998, 1000, 1002. User module docking regions 1004, 1006, 1008, 1010, 1012 are provided in the barriers as shown. A user module mounting bracket such as element 1014 may be provided to fixedly, pivotably, or releasably secure a user module within or to a mounting region. User interfaces 1016, 1018 are generally configured with graphical, textual, and touchscreen elements as described above.

In such embodiments, any one of the multiple user modules may be used to operate the patient support or features thereof. Each of the user interfaces of the multiple user modules are synchronized to provide the same display and data substantially at the same time. In one embodiment, if a user on the right side of the patient support pushes a button while the user on the left side is doing something, the system treats each button activation in sequential order. This makes the workflow "interruptible" by any user module.

Two users can also work together to complete an operation such as weighing a patient. For example, a first user presses the scale control of a user interface of a first user module to activate the patient weighing feature. The first user then holds IV lines or other items or equipment away from the bed surface, while a second user presses the "weigh patient" button and reads or records the patient's weight.

Figure 32:
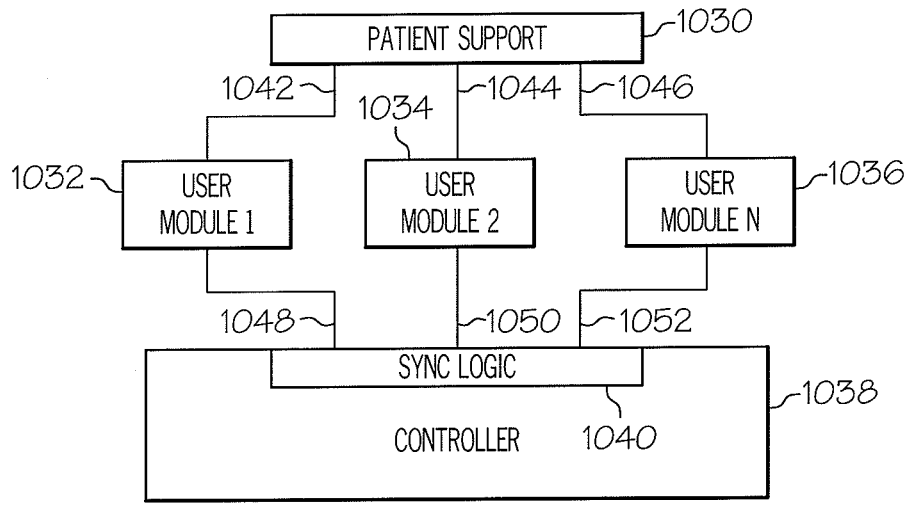
FIG. 32 is a simplified block diagram of components of a system including a patient support, a controller and multiple user modules.

FIG. 32 is a simplified block diagram of one embodiment of a multiple user module system including a patient support 1030, a controller 1038, and a plurality of user modules 1032, 1034, 1036, which are operably coupled to patient support by mechanical and/or electrical links 1042, 1044, 1046 and are electrically coupled controller 1038 via links 1048, 1050, 1052, respectively. Controller 1038 includes synchronization logic 1040 stored in a memory and executable by a processor to synchronize the activities and the displays of the multiple user modules so that when an action is taken at one user module, the displays of the other user modules are automatically updated. Controller 1038 receives input signals from a first user module 1032, a second user module 1034, and a third user module 1036, or any number of user modules. Such signals are time-stamped and controller 1038 applies synchronization logic to process the signals in sequential order and update the output to the displays as needed.

Figure 33:
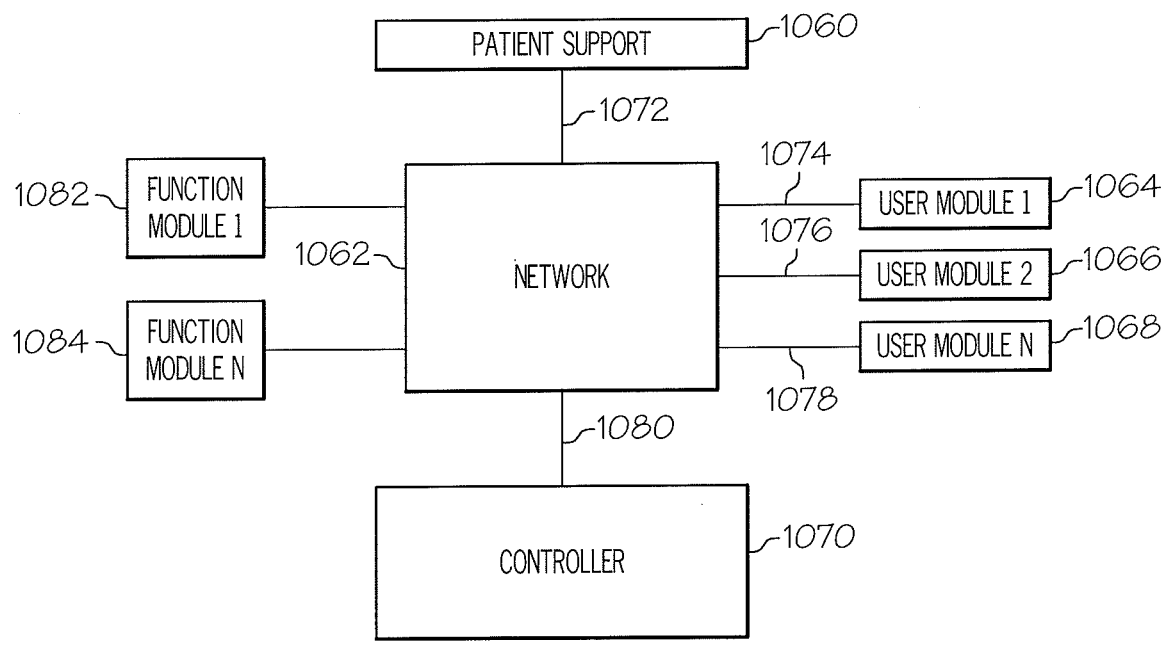
FIG. 33 is simplified block diagram of components of another system including a patient support, a controller, multiple user modules, and a network connecting the controller, the user modules and the patient support.

FIG. 33 is a simplified block diagram of another embodiment of a multiple user interface system including a patient support 1060, a network 1062, a plurality of user modules 1064, 1066, 1068, and a controller 1070. Each of patient support 1060, controller 1070, and user modules 1064, 1066, 1068 are operably coupled to communication network 1062 by communication links 1072, 1074, 1076, 1078, 1080.

In this embodiment, the user modules receive input signals from the user via a touchscreen control or other input device. The input signals are converted by programming logic stored at the module to a network-readable format and sent over the network 1062. The other user modules and the controller 1070 receive the network message. The other user modules acknowledge the message and update their displays as needed. Controller 1070 monitors the network, forwards the message to the appropriate function module 1082, 1084 to perform the requested bed or mattress function, checks for acknowledgement messages confirming that the function has been performed, converts acknowledgement messages to network-readable messages and sends the acknowledgement messages to the user modules over the network. The user modules each receive the acknowledgment messages and update their displays as appropriate. The user modules may each send a reply message to the controller so that the controller knows that each user module has been updated.

The network 1062 may include peer-to-peer connections (for example, as between the user modules and the controller or between the function modules and the controller), master/slave connections, or a combination of peer-to-peer and master-slave connections. An example of a master/slave configuration is a function module that receives input that originates from an analog device, such as a load cell, angle sensor, pressure sensor, position sensor, or the like. For example, a scale module for obtaining patient weight is connected to load cell modules in a master/slave configuration where the load cell modules are the "slaves" because they only communicate with the scale function module.

Figure 34:
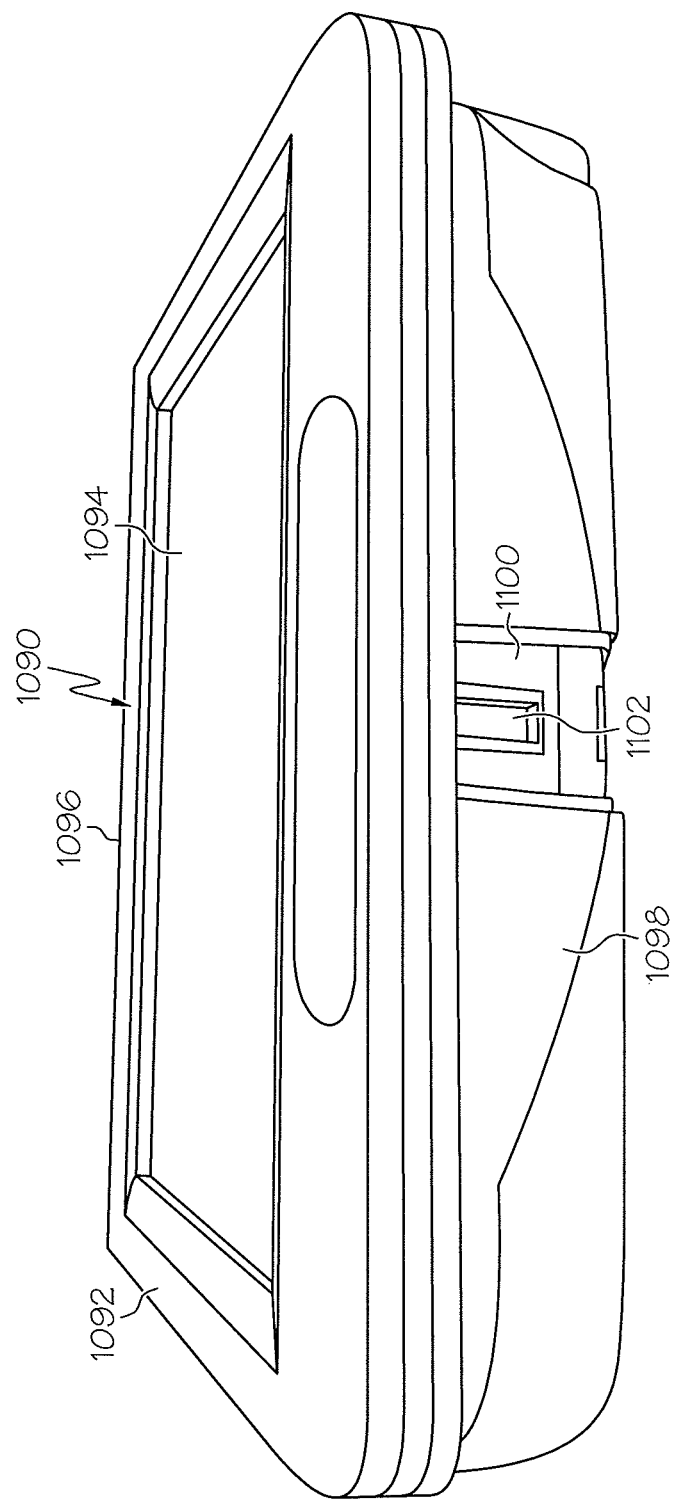
FIG. 34 is a bottom perspective view of a user module including a data and logic connectivity port.

FIG. 34 is a bottom-end perspective view of an exemplary user module 1090. User module 1090 includes a housing 1092 having a top end 1096 and a bottom end 1098. A data/communication port 1100 is located in the bottom end 1098 (although it could be located elsewhere on the user module). Data/communication port 1100 may include a standardized electrical connector 1102, such as a Universal Serial Bus (USB) port, memory card slot, memory stick reader, or similar connector. Connector 1102 enables a peripheral device, storage media, remote computer, or other computing devices, such as portable memory card readers, laptops, or printers, to be connected to the user module 1090 at port 1100.

A memory card (such as SD, MMC, CompactFlash, or the like) or portable memory card reader or other computing device may be directly inserted into or connected to the port 1100 at connector 1102. User module 1090 includes programming logic configured to recognize the existence of a connection at connector 1102, indicate the connection on the display, and display prompts to enable a service technician or other authorized person to perform functions at the user module relating to the connected device or media. For example, software fixes, upgrades or new releases to the user module or modules may be performed, or software fixes, upgrades, or new releases for a bed or mattress function module may be received at the port 1100 and then transmitted to the appropriate function module by the user module over a bed or mattress network. In addition, if a new user module or function module is added to the bed or mattress system, or an existing module is being replaced, software configured for the new module may be uploaded to the system via port 1100.

Figure 35:
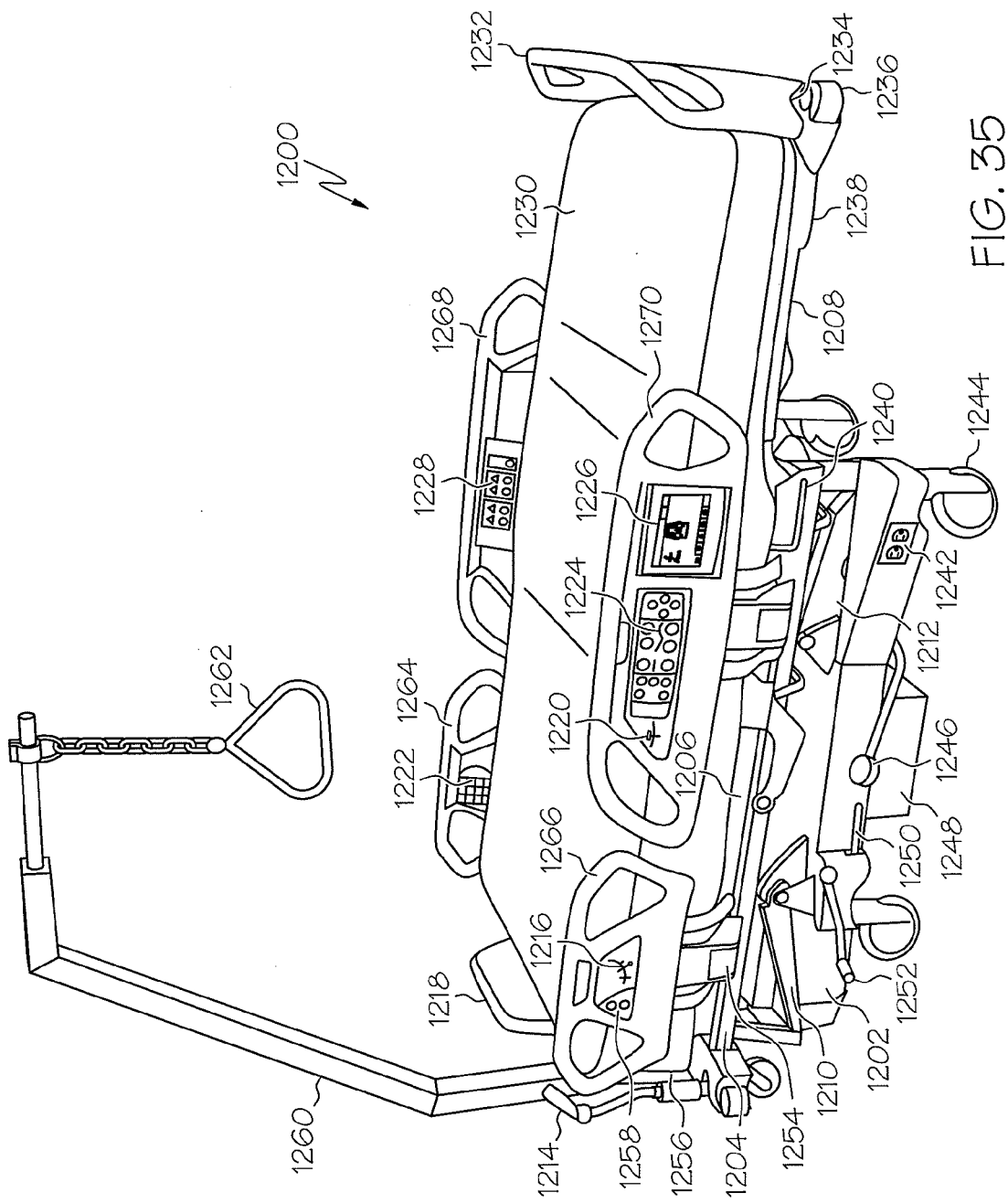
FIG. 35 is a simplified perspective view of an embodiment of a patient support apparatus including siderail-mounted user modules, including a dynamic display, touch-sensitive controls, and a plurality of hardpanel controls located adjacent to the dynamic display.
Figure 36A:
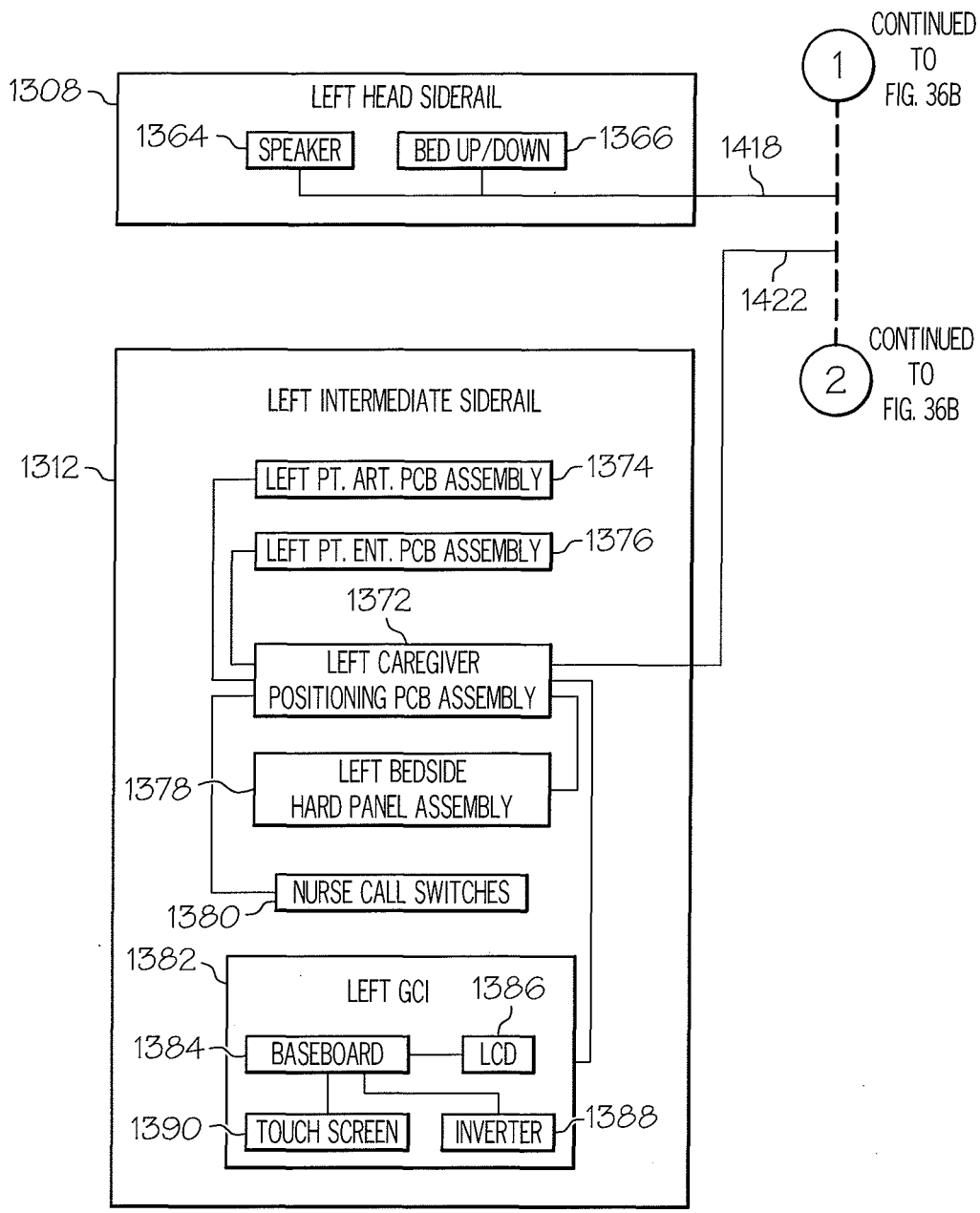
FIGS. 36A-36D are a simplified schematic of an electrical system for the patient support apparatus of FIG. 35.
Figure 36B:
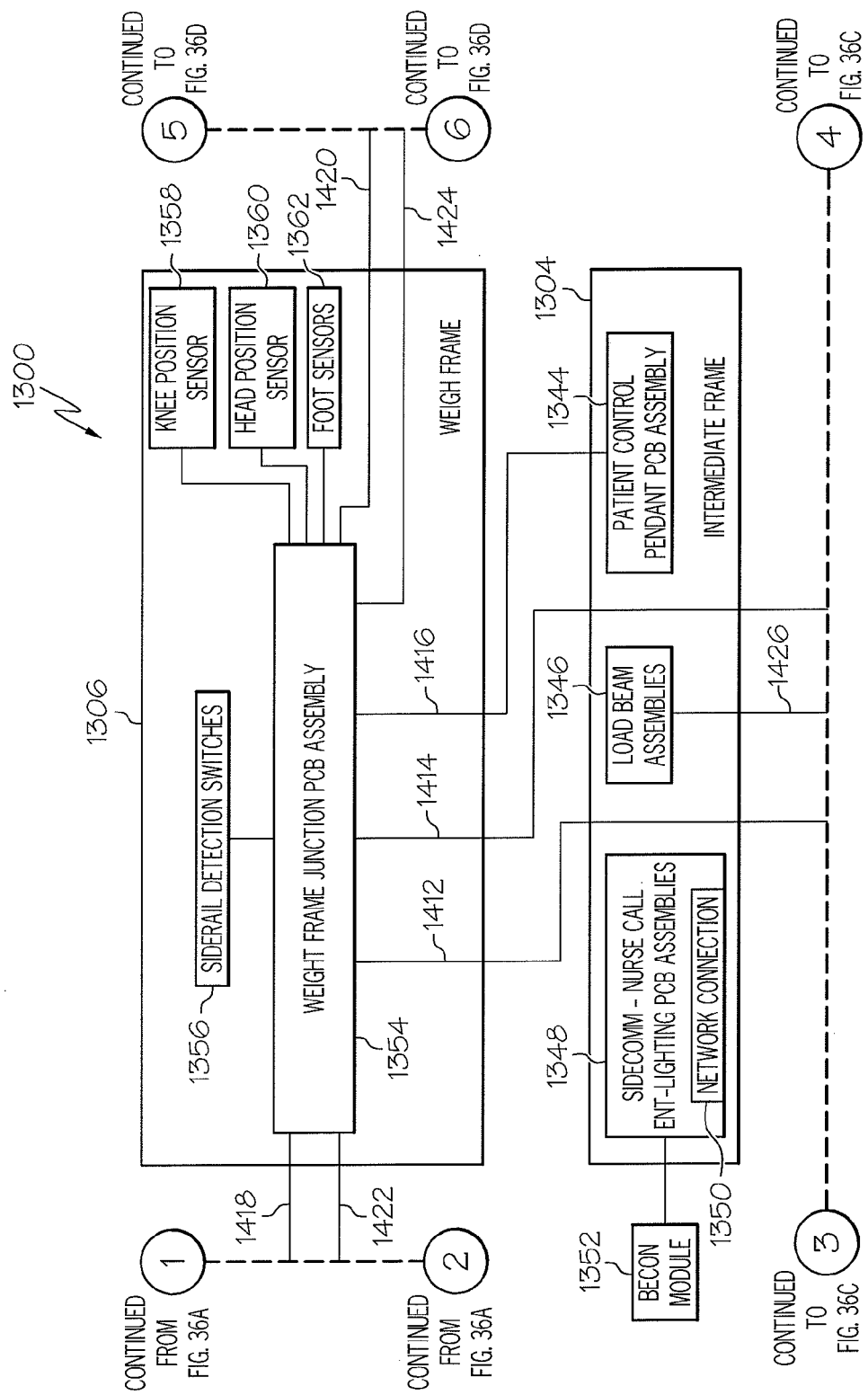
Figure 36C:
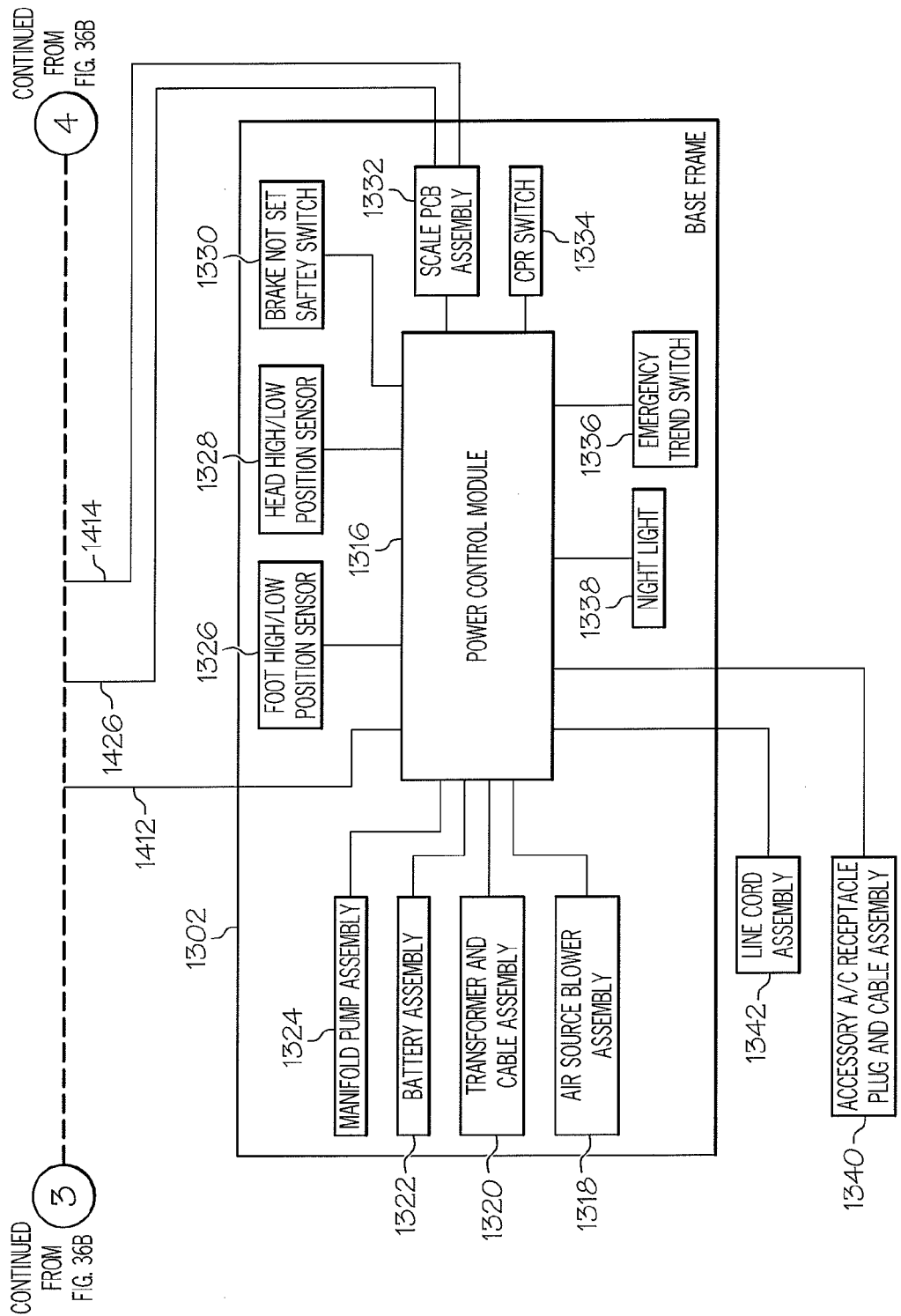
Figure 36D:
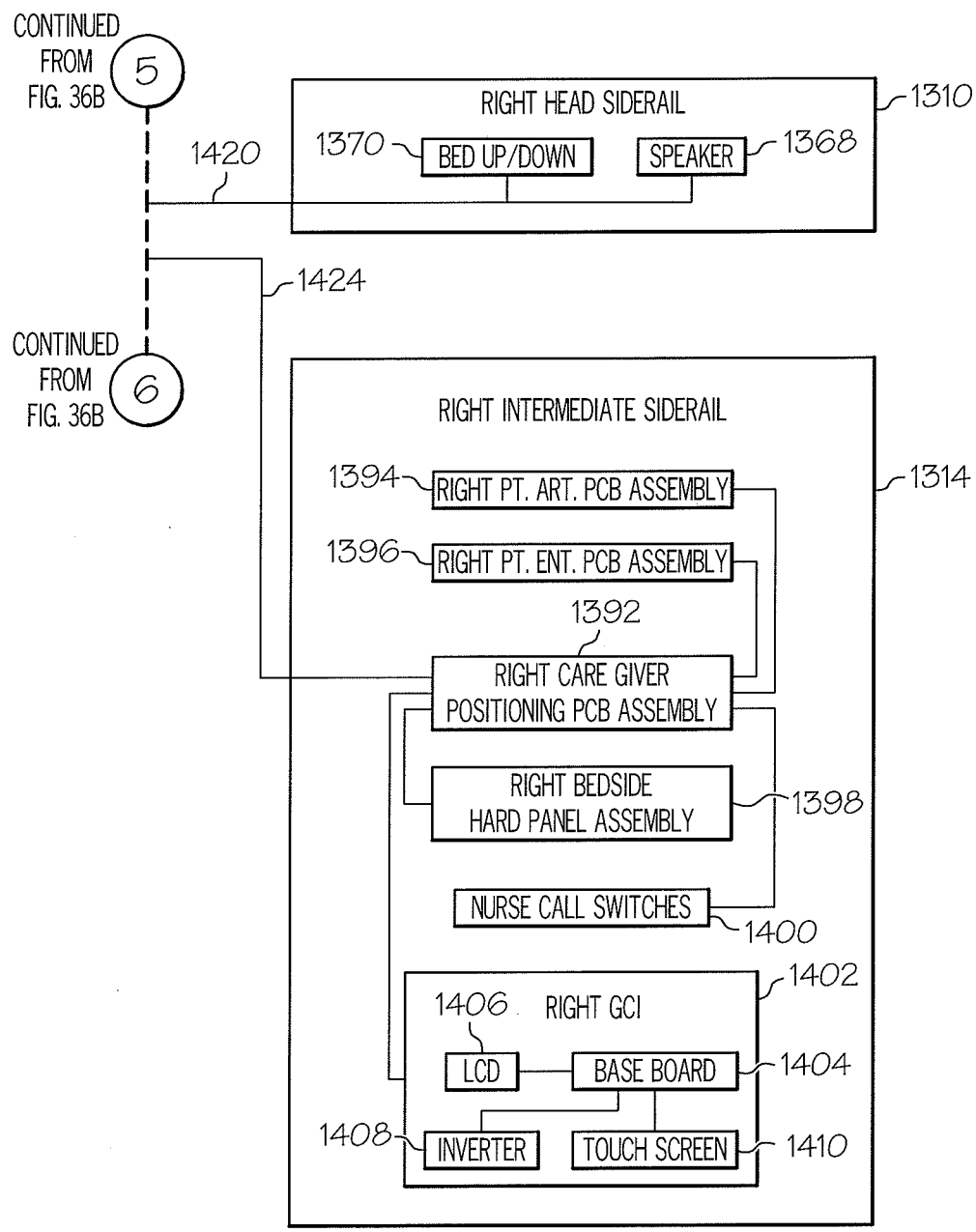

FIG. 35 illustrates an embodiment of a patient support apparatus 1200, which is a powered hospital bed configurable to assume a plurality of different positions, including a horizontal or flat position (shown), a chair position, positions intermediate the horizontal and chair positions, Trendelenburg and reverse Trendelenburg and hi-low positions. Bed 1200 has a bed frame including a base 1202, an intermediate frame 1204, a weigh frame 1206 and a deck 1208. Deck 1208 includes an articulatable head section and an articulatable foot section. Intermediate frame 1204 is supported above base 1202 by lift or articulation arms 1210, 121, and thereby has an adjustable height. Frame 1204 has a retractable and extendable foot section 1238, which includes an automated mechanism for shortening and lengthening the foot section 1238. The length of foot section 1238 may be adjustable to customize the length of the sleep surface for a patient. Alternatively or in addition, the length may be automatically adjusted to facilitate moving bed 1200 into and out of a chair position, i.e., automatically shortened as bed 1200 moves into a chair position and automatically lengthened as bed 1200 moves from the chair position into one of the bed positions.

A support surface 1230 is supported by deck 1208. In the illustrated embodiment, surface 1230 includes a plurality of inflatable bladders, however, surface 1230 may include other types of support members such as foam, three-dimensional material, and the like, and may include additional elements to be configured as a treatment surface (e.g. including pressure reduction and/or low airloss features) or therapy surface (e.g. including pulmonary features such as rotation or percussion and vibration). Additionally, surface 1230 may be usable with patients weighing up to or over 500 pounds. Further, surface 1230 generally has resilient, retractable/extendable, or length-adjustable members (such as specially cut foam or deflatable bladders) in the foot section to cooperate with the length-adjustable foot section 1238.

Head end siderails 1264, 1266 are positioned adjacent the lateral sides of the head section. Intermediate siderails 1268, 170 are also positioned adjacent the lateral sides of the bed and are longitudinally spaced from head end siderails 1264, 1266 as shown. A removable headboard 1218 and removable footboard 1232 are positioned adjacent the head end and foot end, respectively, of bed 1200.

Bed 1200 also includes one or more transport handles 1214, which are configured to enable bed 1200 to be maneuvered or transported manually or with the assistance of a powered transport system 1248, such as the IntelliDrive® transport system sold by the Hill-Rom Company.

Each of siderails 1264, 1266, 1268, 1270 includes an outer panel facing outwardly away from the surface 1230 and an inner panel facing inwardly toward the surface 1230, wherein the inner panel may generally be configured to be accessible to a person positioned on the surface 1230 and the outer panel may be generally configured to be accessible to a user or caregiver not located on the surface 1230.

A head of bed angle indicator 1216 provides a visual cue indicative of the current angle of the head section of bed 1200.

Indicator 1216 is located on an outer panel of head section siderail 1266 in the illustrated embodiment. Similarly, a Trendelenburg angle indicator 1220 provides a visual cue indicative of the current Trendelenburg angle of the bed 1200. Indicator 1220 is located on an outer panel of intermediate siderail 1270 in the illustrated embodiment.

A speaker 1222 is located on the inner panel of head end siderail 1264 in the illustrated embodiment. Speaker 1222 is operably connected to a nurse call system and/or to a patient entertainment system. A patient control panel 1228 is located on the inner panel of intermediate siderail 1268 in the illustrated embodiment and includes buttons, switches, or controls to enable the patient to adjust a position, function or feature of the bed 1200, such as to raise the head section or call a nurse.

Outer panel of head end siderail 1266 also includes a bed hi-low control 1258, which includes buttons or switches to raise and lower the frame 1204 relative to the base 1202. Outer panel of intermediate siderail 1270 also includes siderail controls 1224 and a graphical user interface or graphical caregiver interface (GCI) 1226. In general, siderail controls 1224 include hardpanel electromechanical switches while GCI 1226 includes a dynamic display with touchscreen controls as described above. GCI 1226 is may be pivotably coupled to siderail 1270 as previously described.

In the illustrated embodiment, the inner and outer panels of head end siderails 1264, 1266 are substantially identical and are provided with the same features and functions, and the inner and outer panels of intermediate siderails 1268, 1270 are substantially identical and are provided with the same features and functions, so that a patient or caregiver can access the controls from either side of the bed; however, this need not be the case.

Other features of bed 1200 may include equipment electrical sockets 1234, one or more bumpers or wall guards 1236, drainage bag holders 1240, one or more accessory outlets 1242, casters 1244 (single or dual wheel), foot pedal 1246, emergency Trend or CPR lever 1246, brake and steering system 1252, siderail release mechanisms 1254 (on each siderail), one or more IV poles 1256, and/or patient helper 1260, which includes a trapeze 1262. Additional details of the above-described features and functions of bed 1200 are further described in U.S. Provisional Patent Application Ser. No. 60/982,300, filed Oct. 24, 2007, incorporated herein by reference.

A simplified schematic of an electrical system for bed 1200 is shown in FIGS. 36A-36D. Electrical system 1300 includes base frame components and circuitry 1302, intermediate frame components and circuitry 1304, weigh frame components and circuitry 1306, left and right head siderail components and circuitry 1308, 1310, and left and right intermediate siderail components and circuitry 1312, 1314. Base frame components and circuitry 1302 are coupled to base frame 1202, intermediate frame components and circuitry 1304 are coupled to intermediate frame 1204, weigh frame components and circuitry 1306 are coupled to weigh frame 1206, left and right head siderail components and circuitry 1308, 1310 are coupled to left and right head siderails 1264, 1266, respectively, and left and right intermediate siderail components and circuitry 1312, 1314 are coupled to left and right intermediate siderails 1268, 1270, respectively. In general, the electrical components and circuitry may be embedded in, adhered to, or otherwise mounted in or fastened to a physical component or member of the corresponding frame or barrier member in such a way as to be permanently fixed relative to the frame or barrier member, or may be removable or replaceable relative to the frame or barrier member.

Base frame components and circuitry 1302 includes a power control module 1316, which is electrically connected to a plurality of printed circuit board assemblies and cables, including air source/blower assembly 1318, transformer assembly 1320, battery assembly 1322, manifold and pump assembly 1324, foot hi-low position sensor assembly 1326, head hi-low position sensor assembly 1328, brake safety switch assembly 1330, scale assembly 1332, CPR switch assembly 1334, emergency trend switch assembly 1336, night light assembly 1338, accessory A/C plug and cable assembly 1340, and electrical line cord assembly 1342.

Intermediate frame components and circuitry 1304 includes a plurality of printed circuit board assemblies and cables including a patient control pendant assembly 1344, a plurality of load beam assemblies (four, in the illustrated embodiment) 1346, and sidecomm, nurse call, entertainment, and lighting assemblies 1348. The sidecomm assembly 1348 is coupled to a becon module 1352 and the nurse call assembly is coupled to a network connection 1350 (such as Ethernet) to communicate with an external network.

Weigh frame components and circuitry 1306 includes a plurality of printed circuit board assemblies and cables including a weigh frame junction assembly 1354, siderail detection switch assemblies 1356 (one for each siderail, illustratively), knee position sensor assembly 1358, head position sensor assembly 1360 and foot position sensors 1362.

Left and right head siderail components and circuitry 1308, 1310 include, respectively, a plurality of printed circuit board assemblies and cables including speaker assemblies 1364, 1368 and bed up/down assemblies 1366, 1370.

Left and right intermediate siderail components and circuitry 1312, 1314 include, respectively, left and right caregiver positioning assemblies 1372, 1392. Left and right patient articulation assemblies 1374, 1394, left and right patient entertainment assemblies 1376, 1396, left and right bedside hardpanel assemblies 1378, 1398, left and right nurse call switch assemblies 1380, 1400, and left and right GCIs 1382, 1402, are coupled to left and right intermediate siderail components and circuitry 1312, 1314, respectively. Each GCI assembly 1382, 1402 includes a baseboard 1284, 1404, an LCD 1386, 1406, a touchscreen 1390, 1410, and an inverter 1388, 1408. Each GCI assembly 1382, 1402 displays and operates a graphical user interface including enhanced, highlighted, selectively colored or shaded, and/or animated portions as described above.

Power control module 1316 of the base frame components 1302 is electrically coupled to weigh frame junction assembly 1354 via link 1412. Scale assembly 1332 is electrically coupled to load beam assemblies 1346 of intermediate frame components 1304 via link 1426 and to weigh frame junction assembly 1354 of weigh frame components 1306 via link 1414. Pendant assembly 1344 is electrically coupled to weigh frame junction assembly 1354 by link 1416.

Left and right head siderail components 1308, 1310 are electrically coupled to weigh frame junction assembly 1354 by links 1418, 1420, respectively. Left and right caregiver positioning assemblies 1372, 1392 are electrically coupled to weigh frame junction assembly 1354 by links 1422, 1424, respectively.

In general, electrical couplings as shown in FIG. 36 are usable to communicate power, and/or data, instructions, or commands in digital form, among the various components and assemblies of bed 1200, by insulated wiring, cables, wireless transmission or other type of suitable communication link or electrical or power conduit. The various electrical components and circuitry may be interconnected by a network, such as a CAN or Echelon configuration. Additional details relating to these electrical components and circuitry are provided in U.S. Provisional Patent Application Ser. No. 60/982,300, filed Oct. 24, 2007, incorporated herein by reference.

The drawings are provided to facilitate understanding of the disclosure, and may depict a limited number of elements for ease of explanation. No limits on the number or types of user modules, function modules or other components, features or functionality that may be provided by or connected to any of the disclosed apparatus and systems are intended to be implied by the drawings. Also, in general, features, functional blocks or user interface elements shown but not specifically described herein operate in a like fashion to other similar function blocks or elements as described herein.

The present disclosure describes patentable subject matter with reference to certain illustrative embodiments. Variations, alternatives, and modifications to the illustrated embodiments may be included in the scope of protection available for the patentable subject matter.

The invention claimed is:

1. A user module for a patient support, the user module comprising
   a communication interface configured to communicate signals from the user module to a patient support having at least one automated function and being configured to support a patient in at least a substantially horizontal position and to communicate signals from the patient support to the user module,
   an input device configured to receive a signal indicative of a selection made by a user relating to an automated function of the patient support, and
   an output device including a visual display configured to display a first graphical depiction of a person positioned on a patient support in response to a selection made by a user relating to a first therapy function of the patient support, the first therapy function relating to percussion, vibration or rotation therapy provided to the person positioned on the patient support, and to display a second graphical depiction of a person positioned on a patient support in response to a selection made by a user relating to a second therapy function of the patient support, the second therapy function relating to percussion, vibration or rotation therapy provided to the person positioned on the patient support, wherein the first graphical depiction includes a first animated element indicative of movement of the person associated with operation of the first function of the patient support and the second graphical depiction includes a second animated element indicative of movement of the person associated with operation of the second function of the patient support, and to display a one-touch selection button that requires only a single action of the user to configure a reminder feature relating to the first therapy function or the second therapy function, wherein the reminder feature counts down a period of time after the therapy function is stopped and issues a reminder after the countdown is finished.

2. The user module of claim 1, wherein the output device is further configured to display the first animated element and the second animated element at the same time.

3. The user module of claim 2, wherein the first animated element includes an arrow and a portion of the graphical depiction of a person positioned on a patient support.

4. The user module of claim 3, wherein the second animated element includes concentric circles and a portion of the graphical depiction of a person positioned on a patient support.

5. The user module of claim 4, wherein the output device is further configured to substantially simultaneously display current data relating to at least one alarm feature of the patient support, current data relating to at least one therapy function of the patient support, and a graphical representation of a patient support including an animated portion indicative of a status of an automated function of the patient support.

6. The user module of claim 1, wherein the output device is configured to display a first region including a first selectable option and a second region spaced from the first region, the second region includes a second selectable option, the first selectable option is displayed in a first color and the second selectable option is displayed in a second color contrasting with the first color.

7. The user module of claim 6, wherein the second selectable option is displayed in the second color prior to selection by a user of the second selectable option and the second selectable option is displayed in a third color contrasting with the second color and the first color after selection by a user of the second selectable option.

8. The user module of claim 7, wherein the second color is green and the third color is red.

9. The user module of claim 8, wherein the output device is further configured to display in a data region current data relating to a function of the patient support or a characteristic of a patient positionable on the patient support, and the data region is defined relative to the rest of the display by yellow highlighting.

10. The user module of claim 1, further comprising a user control to configure a setting of the patient support, the user control including a touch sensor associated with a graphical depiction of the user control displayed on the visual display, wherein the depiction of the user control includes a first numerical value representative of the current configuration of the setting, the user control is configured to enable a user to select a second numerical value indicative of a second configuration for the setting by applying one touch to the touch sensor, and the depiction of the user control automatically changes to replace the first numerical value with the second numerical value on the user control when the second numerical value is selected by the user.

11. A patient support apparatus comprising
a frame having first and second longitudinally spaced ends and first and second laterally spaced sides,
a housing positionable adjacent one of the sides or ends of the frame, and
a user module according to claim 1, the user module being supported by the housing, wherein the visual display comprises at least one touchscreen control associated with a region of the visual display, and
at least one electromechanical switch supported by the housing, wherein activation of at least one of the switches activates the visual display of the user interface.

12. The patient support apparatus of claim 11, wherein the housing has a front panel, the user module is supported by the front panel, and an electromechanical switch is spaced from the user module on the front panel and electrically coupled to the user module.

13. The patient support apparatus of claim 12, wherein activation of the electromechanical switch causes a pop-up window to appear on the visual display.

14. The patient support apparatus of claim 13, wherein the user module and the electromechanical switch are coupled to a siderail of the patient support.

15. The patient support apparatus of claim 13, wherein the user interface and the electromechanical switch are coupled to a footboard of the patient support.

16. A patient support apparatus comprising
a bed having first and second longitudinally spaced ends, first and second laterally spaced sides and at least one computer-controllable function,
a controller operably coupled to the bed to control at least one bed function,
a plurality of user modules operably coupled to the controller, each user module configured to display output relating to a bed function and receive input from a user relating to a bed function, at least one of the user modules configured according to claim 1, and
a memory including instructions executable to process first input received by a first user module and second input received by a second user module and automatically update the displays of the user modules.

17. The patient support apparatus of claim 16, wherein at least one of the user modules includes a user interface including a touchscreen control.

18. The patient support apparatus of claim 17, wherein the touchscreen control is activatable by a user to configure a setting for a bed therapy function for which a single value is selectable from a plurality of values, the plurality of values are displayed on the user module, and the touchscreen control is configured to enable the user to select a value from the plurality of values by contacting the touchscreen control only one time.

19. The patient support apparatus of claim 16, wherein the executable instructions include instructions to display the same output on all of the user modules at the same time.

20. The patient support apparatus of claim 16, wherein the second user module display is updated in response to the first input and the first user module display is updated in response to the second input.

21. A user module for a patient support, the user module comprising:
a communication interface configured to communicate signals from the user module to a patient support and to communicate signals from the patient support to the user module;
an input device configured to receive a signal indicative of a selection; and
an output device comprising a visual display to display a graphical depiction in response to a selection relating to a therapy function of the patient support, the therapy function relating to a percussion, a vibration, or a rotation therapy, wherein the graphical depiction includes an animated element indicative of movement of a person associated with operation of the therapy function of the patient support, and to display a one-touch selection button to configure a reminder feature relating to the therapy function, wherein the reminder feature counts down a period of time after the therapy function is stopped.

22. The user module of claim 21, wherein the graphical depiction comprises a depiction of a person positioned on a patient support.

23. The user module of claim 21, wherein the selection is made by a person using the user module.

24. The user module of claim 21, wherein the selection button requires only a single action of the user to configure the reminder feature.

25. The user module of claim 21, wherein the reminder feature issues a reminder after the countdown is finished.

\* \* \* \* \*